United States Patent
Seo et al.

(10) Patent No.: US 7,334,472 B2
(45) Date of Patent: Feb. 26, 2008

(54) APPARATUS AND METHOD FOR MEASURING QUANTITY OF PHYSICAL EXERCISE USING ACCELERATION SENSOR

(75) Inventors: Jeong-Wook Seo, Daegu (KR); Wei-Jin Park, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 332 days.

(21) Appl. No.: 11/187,857

(22) Filed: Jul. 25, 2005

(65) Prior Publication Data

US 2006/0020177 A1    Jan. 26, 2006

(30) Foreign Application Priority Data

Jul. 24, 2004 (KR) .............. 10-2004-0058088
Oct. 22, 2004 (KR) .............. 10-2004-0085051

(51) Int. Cl.
*A61B 5/22* (2006.01)
(52) U.S. Cl. .............................. 73/379.01
(58) Field of Classification Search ......... 73/379.01, 73/379.02; 702/160, 141; 482/3
See application file for complete search history.

(56) References Cited

U.S. PATENT DOCUMENTS

| | | | |
|---|---|---|---|
| 4,962,469 A | 10/1990 | Ono et al. | |
| 5,263,491 A | 11/1993 | Thornton et al. | |
| 6,217,523 B1 | 4/2001 | Amano et al. | |
| 6,254,513 B1* | 7/2001 | Takenaka et al. | 482/3 |
| 2005/0240375 A1* | 10/2005 | Sugai | 702/160 |
| 2006/0100817 A1* | 5/2006 | You et al. | 702/141 |

FOREIGN PATENT DOCUMENTS

| | | |
|---|---|---|
| EP | 1 134 555 | 9/2001 |
| EP | 1 256 316 | 11/2002 |

(Continued)

OTHER PUBLICATIONS

Seon-Woo Lee et al. "Recognition of Walking Behaviors for Pedestrian Navigation," *Proceedings of the 2001 IEEE International Conference on Control Applications*, pp. 1152-1155, Sep. 5-7, 2001, Mexico City, Mexico.

(Continued)

*Primary Examiner*—Jewel Thompson
(74) *Attorney, Agent, or Firm*—Roylance, Abrams, Berdo & Goodman, L.L.P.

(57) ABSTRACT

Disclosed are a method for measuring quantity of exercise and an apparatus comprising an acceleration sensor for generating acceleration information by measuring the quantity of exercise according to user movement, sensor control unit for supplying power to the acceleration sensor and sampling the acceleration information generated from the acceleration sensor, a dynamic energy measurement unit for converting the sampled acceleration information into dynamic energy, comparing a local maximum value with a predetermined threshold value if an ascending gradient of the dynamic energy has the local maximum value exceeding a predetermined value and determining a user step if the local maximum value exceeds the predetermined threshold value, a calorie consumption measurement unit for calculating calorie consumption by analyzing an energy level of dynamic energy determined as a user step, a memory for storing information, and a display section for displaying information related to the number of steps and calorie consumption.

72 Claims, 60 Drawing Sheets

FOREIGN PATENT DOCUMENTS

| | | |
|---|---|---|
| EP | 1 422 677 | 5/2004 |
| JP | 2001-143048 | 5/2001 |
| JP | 2004-120688 A | 4/2004 |
| KR | 10-2001-0045717 A | 6/2001 |
| WO | WO 01-52718 | 7/2001 |
| WO | WO 2004-052203 | 6/2004 |

OTHER PUBLICATIONS

Da Silva, F.W. et al., "Motion Cyclification by Time×Frequency Warping," *Computer Graphics and Image Processing 1999*, Proceedings XII Brazilian Symposium on Campinas, Brazil, Oct. 17-20, 1999, Los Alamitos, CA, US *IEEE Computer. Soc.*, U.S., Oct. 17, 1999, pp. 49-58, XP010358895 ISBN: 0-7695-0481-7.

\* cited by examiner

Δ: 0.00V
@: -100mV
Δ: 200ms
@: 100ms ch1 FREQUENCY
38.49Hz ch1+PULSE WIDTH
3.400ms ch1+PULSE WIDTH
22.58ms

13 JUNE 2005
18:14:21

Δ: 20.0mV
@: -120mV
Δ: 113ms
@: 50.4ms ch1 FREQUENCY
76.96Hz ch1+PULSE WIDTH
3.440ms ch1+PULSE WIDTH
9.900ms

13 JUNE 2005
18:13:26

APPARATUS AND METHOD FOR MEASURING QUANTITY OF PHYSICAL EXERCISE USING ACCELERATION SENSOR

PRIORITY

This application claims the benefit under 35 U.S.C. §119(a) of an application entitled "Apparatus And Method For Measuring Quantity Of Physical Exercise Using Acceleration Sensor" filed in the Korean Intellectual Property Office on Jul. 24, 2004 and Oct. 22, 2004 and assigned Serial Nos. 2004-58088 and 2004-85051, respectively, the entire contents of each are incorporated herein by reference.

BACKGROUND OF THE INVENTION

1. Field of the Invention

The present invention relates to an apparatus and a method for measuring quantity of exercise. More particularly, the present invention relates to an apparatus and a method for measuring quantity of exercise by using an acceleration sensor.

2. Description of the Related Art

As is generally known in the art, pedometers are appliances used for measuring the quantity of exercise of a person. Pedometers are portable appliances capable of counting the number of steps and measuring calorie consumption by detecting the quantity of exercise of a person. Such pedometers are classified into mechanical pedometers and electronic pedometers.

The mechanical pedometer counts the number of steps by measuring the number of vertical vibrations of a pendulum accommodated in the mechanical pedometer when the person walks or runs. However, the mechanical pedometer may not precisely measure the number of vertical vibrations of the pendulum according to the steps of the person if it is carried in a pocket of clothing or hung around the neck of the user. In addition, if the position of the mechanical pedometer is not vertical to the ground, the vertical vibration of the pendulum installed in the mechanical pedometer may not match the steps of the person, so a measurement error may occur.

The mechanical and electronic pedometers simply measure calorie consumption in proportion to the number of steps. However, the person may consume a higher amount of calories in proportion to the exercise intensity. That is, the person may consume a higher amount of calories when running than when walking slowly. Thus, the mechanical and electronic pedometers may not precisely detect the calorie consumption in proportion to the quantity of exercise.

Since the pedometer is a portable appliance, the pedometer is equipped with a battery to measure and display the quantity of exercise of the person. In addition, the pedometer must continuously check the motion of the person, so it is necessary to continuously maintain the pedometer in a power-on state, which causes high power consumption.

In general, the pedometer measures and displays the daily quantity of exercise, so the pedometer cannot manage the number of steps and the calorie consumption accumulated for a long period of time. That is, the pedometer has a compact size, so it is difficult to maintain the small size of the pedometer in order for the pedometer to accumulate and manage all of the daily quantity of exercise, weekly quantity of exercise, and monthly quantity of exercise as required by the user.

SUMMARY OF THE INVENTION

Accordingly, the present invention has been made to solve the above-mentioned problems occurring in the prior art, and an object of the present invention is to provide an apparatus and a method for precisely measuring the quantity of exercise of a user by using an acceleration sensor.

Another object of the present invention is to provide an apparatus and a method capable of measuring and displaying the calorie consumption according to the weight and quantity of exercise of a user.

Still another object of the present invention is to provide an apparatus and a method capable of reducing the power consumption of a dynamic energy measurement apparatus by discontinuously controlling the dynamic energy measurement apparatus.

Still yet another object of the present invention is to provide an apparatus and a method capable of accumulating the quantity of exercise of a user during a predetermined period of time selected by a user and displaying the quantity of exercise using figures or graphs.

Still yet another object of the present invention is to provide an apparatus and a method capable of enabling a portable terminal equipped with a dynamic energy measurement apparatus to control an operation of the dynamic energy measurement apparatus.

Still yet another object of the present invention is to provide an apparatus and a method capable of enabling a pedometer and a portable terminal equipped with the pedometer to process information related to the quantity of exercise according to the steps of a user while eliminating the exercise information caused by an external impact applied to the pedometer and the portable terminal equipped with the pedometer.

Still yet another object of the present invention is to provide an apparatus and a method capable of enabling a pedometer and a portable terminal equipped with the pedometer to check the type of exercise of the user and to variably control the quantity of exercise according to the type of exercise of the user.

Still yet another object of the present invention is to provide an apparatus and a method capable of enabling a pedometer and a portable terminal equipped with the pedometer to check the type of exercise of the user and to variably control the sampling interval for measuring the quantity of exercise according to the type of exercise of the user, thereby precisely measuring the quantity of exercise of the user.

Still yet another object of the present invention is to provide an apparatus and a method capable of enabling a pedometer and a portable terminal equipped with the pedometer to check the type of exercise of the user and to precisely measure the user's calorie consumption according to the type of exercise performed by the user.

Still yet another object of the present invention is to provide an apparatus and a method capable of enabling a pedometer and a portable terminal equipped with the pedometer to check the type of exercise of the user and the attachment position of the pedometer in order to precisely measure the user's calorie consumption according to the type of exercise performed by the user and the attachment position of the pedometer.

Still yet another object of the present invention is to provide an apparatus and a method capable of enabling a pedometer and a portable terminal equipped with the pedometer to process information related to the quantity of exercise of a user based on the number of steps of a user while eliminating exercise information caused by external sound or other vibrations.

Still yet another object of the present invention is to provide an apparatus and a method capable of enabling a pedometer and a portable terminal equipped with the pedometer to reduce the power consumption by changing the sampling frequencies if a step of a user is not detected for a predetermined period of time.

Still yet another object of the present invention is to provide an apparatus and a method capable of preventing a pedometer installed in a portable terminal from malfunctioning by temporarily stopping the operation of the pedometer when the pedometer malfunctions.

BRIEF DESCRIPTION OF THE DRAWINGS

The above and other objects, features and advantages of the present invention will be more apparent from the following detailed description taken in conjunction with the accompanying drawings, in which.

Throughout the drawings, it should be understood that like reference numbers refer to like features, structures, steps, operations and elements.

DETAILED DESCRIPTION OF EXEMPLARY EMBODIMENT

Figure 1:
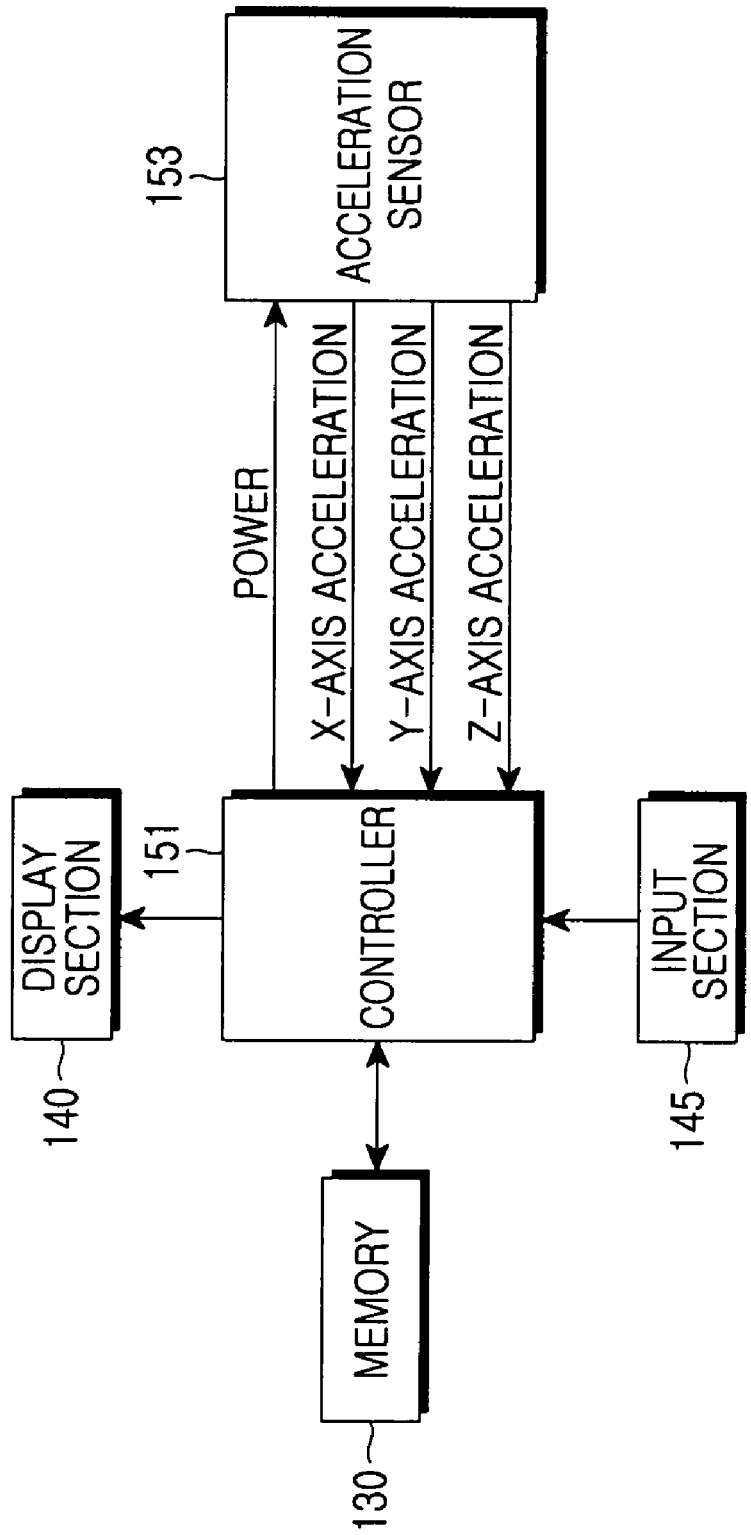
FIG. 1 is a block view illustrating a structure of a pedometer according to an embodiment of the present invention.

Hereinafter, embodiments of the present invention will be described with reference to the accompanying drawings. The same reference numerals will be designated for the same elements throughout the drawings.

Specific details, such as the weight and height of a user, exercise time and calorie values, will be used in the following description for illustrative purpose only. It will be understood by those skilled in the art that the present invention can be embodied without the specific values or by modifying the specific values.

The present invention relates to the measurement for the quantity of exercise performed by a user. In particular, embodiments of the present invention relate to the measurement for the quantity of exercise performed by a user by using an acceleration sensor. The acceleration sensor can simultaneously detect static acceleration of an object, which is generated due to the acceleration of gravity, and dynamic acceleration of an object, which is generated when the object moves against the ground. It is possible to measure an inclination degree of the object, the force applied to the object, and the movement of the object by using acceleration information.

A pedometer or a calorie meter may analyze and utilize such acceleration information. For instance, the pedometer or the calorie meter can count the number of steps or can measure the calories consumed based on the acceleration data of a user detected by the acceleration sensor. In this case, since the acceleration sensor generates three-dimensional acceleration information, the motion of the user can be detected three-dimensionally, so the movement of the user can be precisely detected. In addition, since the quantity of exercise performed by the user can be precisely detected, it is possible to precisely calculate the calories consumed by a user based on the quantity of exercise. Thus, the embodiments of the present invention provide an apparatus and a method capable of precisely measuring the quantity of exercise and the calorie consumed by a user by using the acceleration sensor.

In the following description, an apparatus for measuring the quantity of exercise is called a "pedometer". The pedometer can be used as an independent appliance or can be installed in a portable terminal. According to an exemplary embodiment of the present invention, the pedometer is installed in the portable terminal. That is, the portable terminal according to an embodiment of the present invention comprises the pedometer having an acceleration sensor so that the pedometer measures the quantity of exercise of the user when the user carrying the portable terminal is exercising. The information of the user detected by the pedometer is accumulated in a memory of the portable terminal and the quantity of exercise of the user is displayed in a display section of the portable terminal. If the pedometer is provided with a memory and a display section, the pedometer can be used as an independent appliance without being installed in the portable terminal.

Hereinafter, embodiments of the present invention will be described in more detail with reference to accompanying drawings.

FIG. 1 is a block view illustrating a structure of a pedometer according to an embodiment of the present invention.

Referring to FIG. 1, the pedometer comprises a controller 151 for controlling an operation of the pedometer. An input section 145 is provided to allow a user to input various parameters into the controller 151, such as user information (for example, the weight and height of a user), an operation mode, a pedometer reset, a request for changing a position of the pedometer and a request for displaying an exercise record. The memory 130 stores parameters for controlling an acceleration sensor 153 and measured exercise information under the control of the controller 151. A display section 140 displays the measured quantity of exercise and control information under the control of the controller 151. The acceleration sensor 153 receives power during a predetermined period of time and generates acceleration information by measuring the quantity of exercise under the control of the controller 151.

The acceleration sensor 153 intermittently receives operational power under the control of the controller 151. Upon receiving the operational power, the acceleration sensor 153 measures the acceleration information according to the position of the portable terminal and outputs data thereof to the controller 151; The acceleration sensor 153 is a three-dimensional acceleration sensor capable of generating three-dimensional signals for each of X, Y and Z-axes.

The acceleration sensor 153 may detect acceleration, velocity and displacement of an object based on the three-dimensional acceleration information. In addition, the acceleration sensor 153 may detect the movement of the object based on the three-dimensional acceleration information. At this time, the three-dimensional acceleration information preferably includes the acceleration of gravity and relative acceleration of the object. The inclination degree of the object with respect to the ground can be detected based on the acceleration of gravity of the object, which consists of low-frequency components. The relative acceleration consists of high-frequency components, which can be created when the object moves. Thus, the components of the above two accelerations can be obtained through a frequency analysis and the components represent information related to a rotational angle and the direction of movement of the object. If a three-dimensional acceleration module is attached to a person, the three-dimensional acceleration module can act as a pedometer. In addition, the three-dimensional acceleration module can be utilized as a speedometer if it is attached to a vehicle. Table 1 shows the types of data that can be obtained in the frequency band of acceleration information.

TABLE 1

| Acceleration frequency component | Data output information | Data application |
|---|---|---|
| 0 Hz to 20 Hz | Acceleration of gravity according to gradient of sensor with respect to ground | Mobile input unit Game device input unit |
| 5 Hz to 100 Hz | Movement pattern of persons or animals | Measurement of steps and calories Movement of finger tip |
| 100 Hz to 200 Hz | Movement pattern of objects moving at high speed | Vehicle shock-proof system Analysis for movement pattern of flying object |
| Above 200 Hz | Noise | |

The pedometer can be realized by using the acceleration sensor 153 capable of generating acceleration information as shown in Table 1. According to an embodiment of the present invention, the Atmega8L commercially available from Atmel company, which is located in San Jose, Calif., United States can be used as the controller 151 and the HAAM-301A sensor commercially available from Hokuriku Electric Industry Co.,Ltd. (HDK), which is located in Toyama City, Japan, can be used as the acceleration sensor 153. The HAAM301A is a three-dimensional sensor capable of generating acceleration information in the form of analog signals. The output level of the HAAM301A is shown in Equation 1.

$$Vout(x) = 200 \text{ mV}/g \times a(x) + \frac{1}{2}Vcc_{sensor}$$

$$Vout(y) = 200 \text{ mV}/g \times a(y) + \frac{1}{2}Vcc_{sensor}$$

$$Vout(z) = 200 \text{ mV}/g \times a(z) + \frac{1}{2}Vcc_{sensor}$$

Equation 1

Wherein Vout: acceleration outputted from three-dimensional acceleration sensor;

g: acceleration of gravity (9.8 m/s$^2$);

a: acceleration applied to acceleration sensor; and

Vcc: power of acceleration sensor.

If the acceleration sensor 153 is installed in the portable terminal, the acceleration sensor 153 generates three-dimensional acceleration information as shown in Equation 1 when the portable terminal is inclined. At this time, the acceleration sensor 153 generates various three-dimensional acceleration information depending on the inclination degree of the portable terminal.

FIGS. 2A to 2F are views illustrating output information of the acceleration sensor 153 based on the inclination degree of the portable terminal equipped with the acceleration sensor 153 according to an embodiment of the present invention.

Figure 2A:
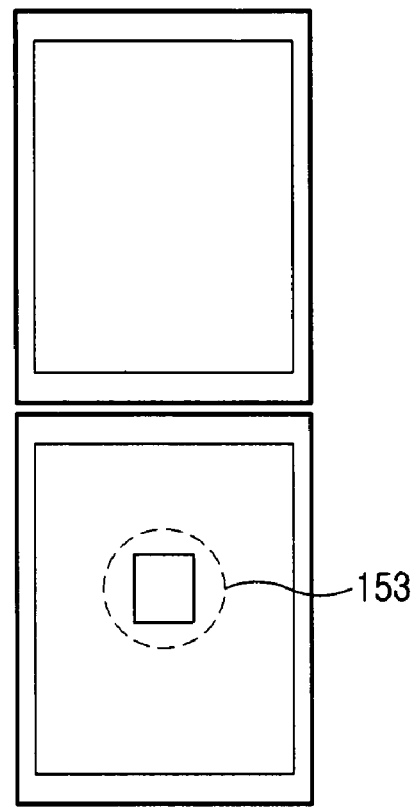
FIGS. 2A to 2F are views illustrating output characteristics of an acceleration sensor based on the positions of a portable terminal according to an embodiment of the present invention.
Figure 2B:
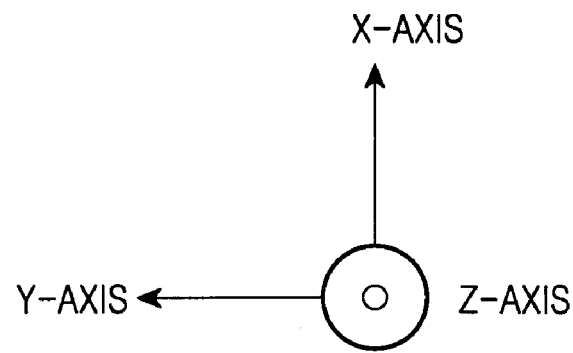
Figure 2C:
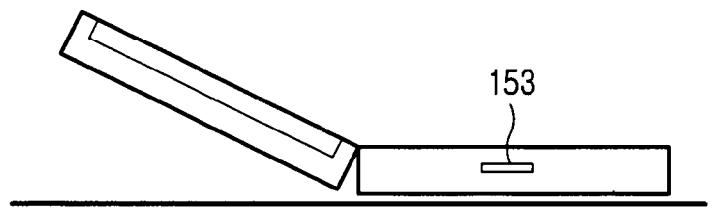
Figure 2D:
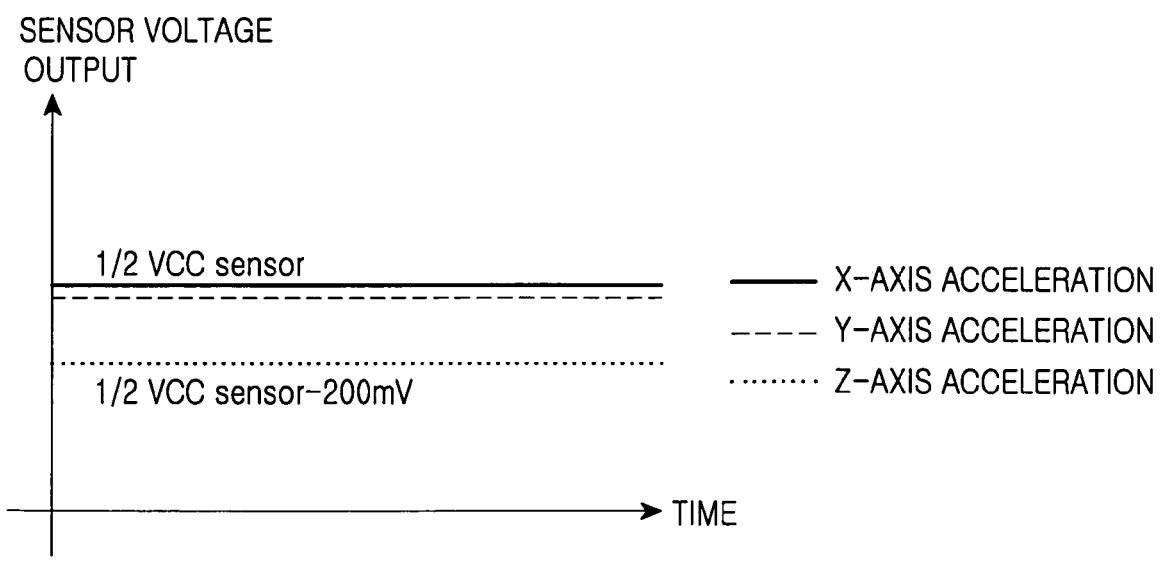
Figure 2E:
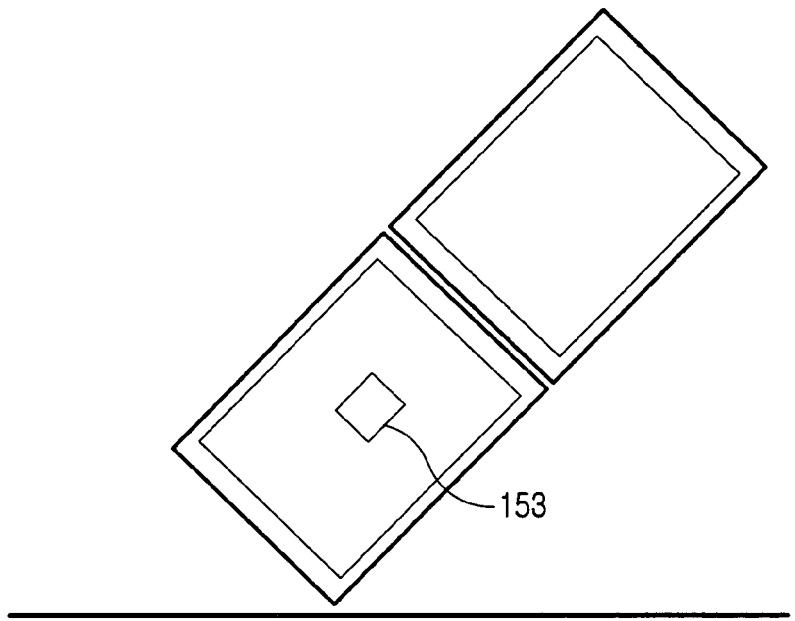
Figure 2F:
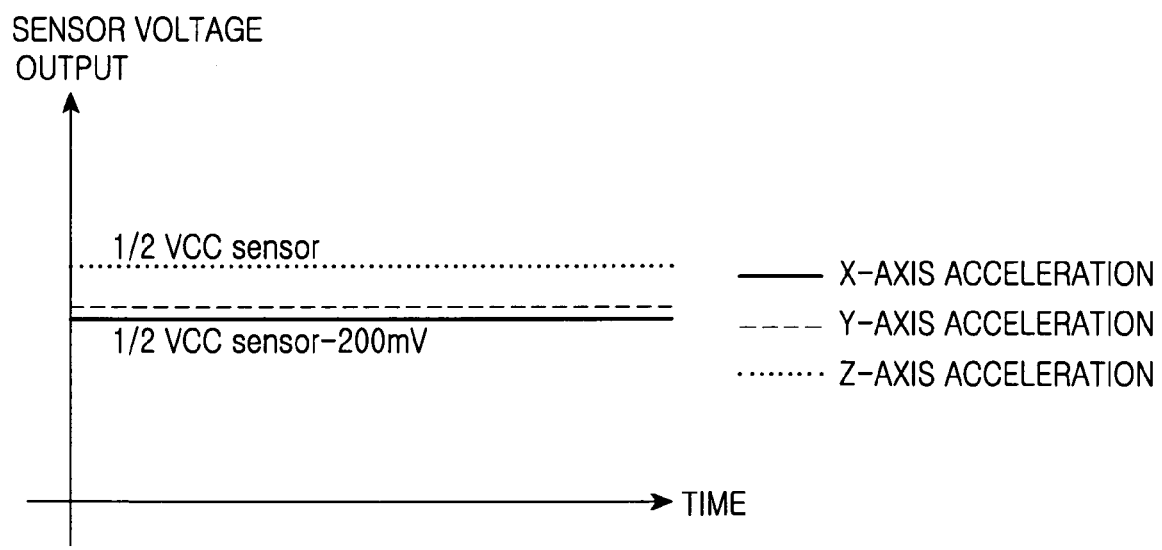

Referring to FIGS. 2A and 2B, the acceleration sensor 153 installed on a predetermined portion of a pedometer. At this time, if the pedometer equipped with the acceleration sensor 153 is parallel to the ground as shown in FIG. 2A (that is, if the pedometer makes contact with the ground as shown in FIG. 2C), a Z-axis is subject to the gravity, but an X-axis and a Y-axis are not subject to the gravity. Accordingly, when the pedometer is positioned as shown in FIG. 2C, the acceleration sensor 153 outputs acceleration information as shown in FIG. 2D. As shown in FIG. 2D, a Z-axis value of the output acceleration information is changed as compared to the X and Y axes, while the X-axis and Y-axis values of the output acceleration information may not be influenced by the gravity. In addition, as shown in FIG. 2E, if the pedometer stands upright, the Z-axis is not influenced by the gravity and the X-axis and Y-axis are subject to the gravity. Accordingly, the acceleration sensor 153 generates acceleration information as shown in FIG. 2F.

As the acceleration information is generated, the controller 151 combines and analyzes the acceleration information, thereby determining whether the acceleration information represents the step of the user. That is, the controller 151 receives the acceleration information from the acceleration sensor 153 and extracts dynamic energy components from the acceleration information, thereby determining the step of the user and calculating the calories consumed.

That is, the controller 151 of the pedometer serves as a sensor control unit and a measurement unit for the quantity of exercise and the power consumption of the device.

When the controller 151 serves as the sensor control unit, the controller 151 supplies power to the acceleration sensor 153 for a predetermined period of time with a first time interval and samples the acceleration information output from the acceleration sensor at a second predetermined point during a second time interval. The first time interval means a sampling interval and the second time interval means a real power supply section in the sampling interval, which is shown as 231 to 233 in FIG. 3D.

When the controller 151 serves as the measurement unit for the quantity of exercise, the controller 151 converts the sampled acceleration information into dynamic energy. If an ascending gradient of the converted dynamic energy has a value above a predetermined value and a local maximum value, the controller 151 compares the local maximum value with a predetermined threshold value and determines 1-step when the local maximum value exceeds the predetermined threshold value. To this end, the controller 151 comprises an acceleration information accumulation section for accumulating the acceleration information for the purpose of performing a discrete cosine transform (DCT), a DCT section for performing the DCT of the accumulated acceleration information, an energy extracting section for extracting energy data from predetermined frequency bands by combining the DCT acceleration information, and a determination section for determining the type of step the user has taken when the local maximum value exceeds the predetermined threshold value by comparing the local maximum value with the predetermined threshold value when the ascending gradient of the converted dynamic energy has the value above the predetermined value and the local maximum value.

When the controller 151 serves as the measurement unit for calorie consumption, the controller 151 has energy level values of at least two intervals corresponding to the walking speed determined through experimentation and the calorie consumption value in each energy level interval. In addition, the controller 151 compares a present energy level value with the energy level value of each interval, thereby calculating the energy level value of each interval and the calorie consumption value thereof. According to an embodiment of the present invention, the energy level interval may vary depending on the position where the pedometer is attached to the user and the type of exercise, such as running at full speed, jogging, normal walking and slow walking.

In addition, the controller 151 of the pedometer may further comprise a sampling interval determination section in addition to a sensor control section, a dynamic energy measurement section, and a calorie consumption measurement section. That is, according to an embodiment of the present invention, the pedometer determines the type of exercise being performed by the user and sets the sampling frequency based the determination of the type of exercise, thereby effectively controlling the operation of the acceleration sensor 153. Thus, the user can set the sampling frequency as a normal measurement mode (for example, $\frac{1}{18}$ second) or a detail measurement mode (for example, $\frac{1}{35}$ second). Since the sampling frequency in the detail measurement mode is higher than the sampling frequency in the normal measurement mode, the output of the acceleration sensor 153 is precisely represented in the detail measurement mode. When at least two sampling frequencies are used, it is possible to effectively measure the quantity of exercise performed by the user by controlling the sampling interval of the sampling frequencies according to the type of exercise performed by the user. For instance, if the user runs and walks with the pedometer, the acceleration sensor 153 generates a signal having a higher energy level and a faster level trigger operation when the user runs. That is, if the type of exercise includes walking and running, it is possible to recognize the type of exercise (walking or running) based on a time interval between steps. Accordingly, the sampling frequency in the running mode is higher than the sample frequency in the walking mode. Thus, if at least two sampling frequencies are used, a lower sampling frequency is supplied to the acceleration sensor 153 when the user walks and a higher sampling frequency is supplied to the acceleration sensor 153 when the user runs. In this case, the acceleration information generated from the acceleration sensor 153 can be adaptively controlled according to the type of exercise performed by the user so that the acceleration sensor 153 may stably generate the acceleration information.

Figure 9:
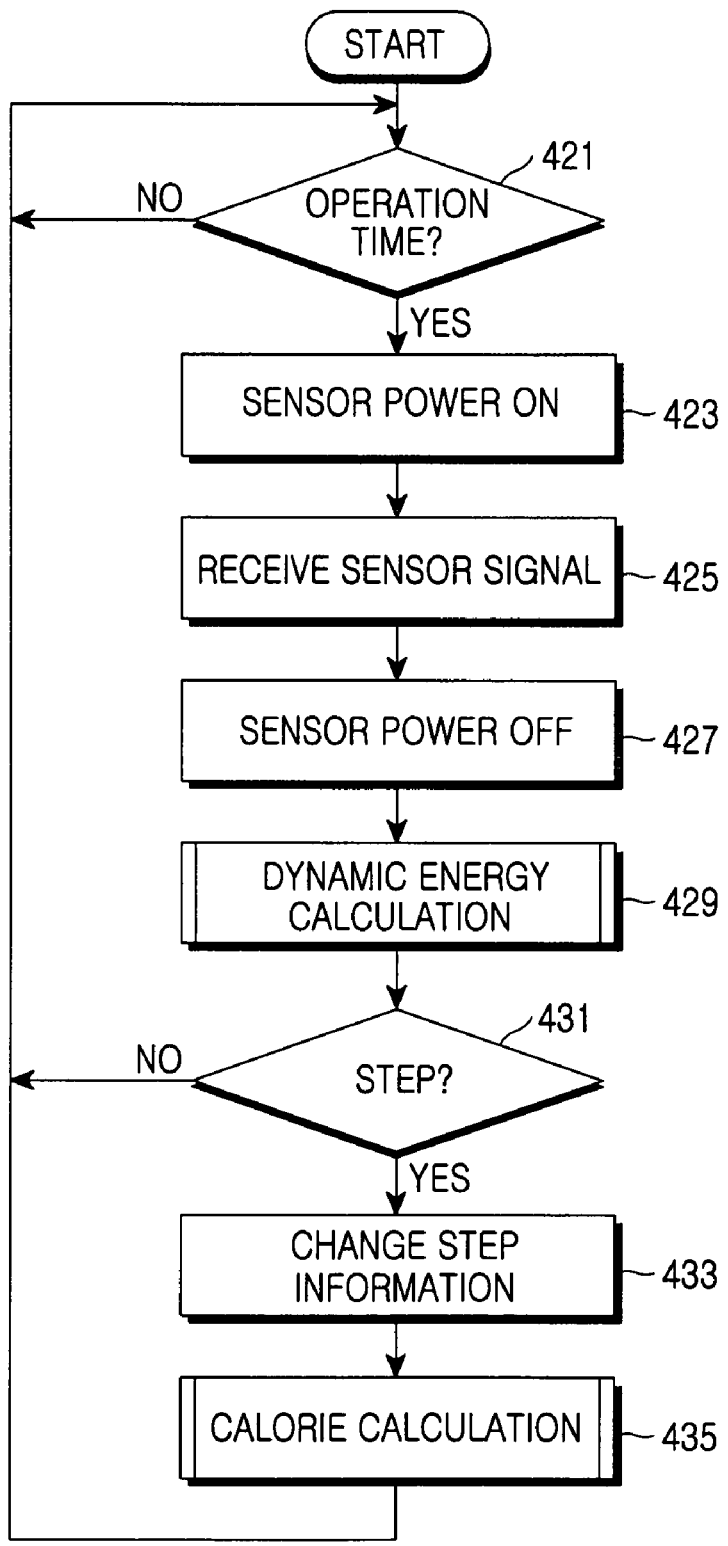
FIG. 9 is a flowchart illustrating the procedure for measuring the quantity of exercise and calorie consumption by controlling an acceleration sensor using a controller of a pedometer according to an embodiment of the present invention.

Therefore, embodiments of the present invention provide a sampling interval determination section capable of generating a sampling frequency for controlling the sampling interval of the acceleration sensor 153 by detecting the type of exercise performed by a user based on the high frequency characteristic of DCT information generated from the dynamic energy measurement section. The sampling interval determination section experimentally obtains and accumulates the level of the high frequency signal of the DCT information and level trigger intervals measured according to the type of exercise performed by the user (walking and running, or in more detail, running at full speed, jogging, fast walking and walking). In addition, the sampling interval determination section takes the mean of the level of the high frequency signal and level trigger intervals according to the type of exercise and stores information related to the reference level of the high frequency signal and level trigger time for determining the type of exercise performed by the user in the memory section as a table. After that, if the dynamic energy measurement section generates the DCT information, the sampling interval determination section monitors the level of the high frequency signal of the DCT information and the level trigger time and compares them with the reference level of the high frequency signal and level trigger time stored in the memory section, thereby determining the type of exercise performed by the user satisfying the above parameters. In addition, the sampling interval determination section sets the sampling frequency corresponding to the type of exercise and supplies the sampling frequency to the acceleration sensor 153. Accordingly, the acceleration sensor 153 can accurately detect the acceleration information according to the type of exercise performed by the user based on the sampling frequency generated from the sampling interval determination section. In the meantime, if a power management unit, which will be described later in more detail with reference to FIG. 9, is used, power consumption may vary depending on variations in the sampling frequency. Thus, the above sampling frequency (normal measurement mode: $\frac{1}{18}$ second, detail measurement mode: $\frac{1}{35}$) may also vary depending on the measurement environment including the power consumption grade. That is, the user may reduce the sampling frequency in order to reduce power consumption, or increase the sampling frequency for the purpose of obtaining precise measurements.

Hereinafter, an operational principle of the pedometer according to an embodiment of the present invention will be described in an order of an operational procedure, a step determination procedure, and a calorie calculation procedure of the pedometer.

First, the operational procedure of the pedometer according to an embodiment of the present invention will be described.

According to an embodiment of the present invention, the controller 151 of the pedometer discontinuously controls the acceleration sensor 153. If power is continuously supplied to the acceleration sensor 153, the acceleration sensor 153 may continuously operate, causing great power consumption. Thus, according to an embodiment of the present invention, operational time for the acceleration sensor 153 is determined through an experiment by calculating walking time of a person and the controller 151 intermittently supplies the operational power to the acceleration sensor 153 with a predetermined time interval, thereby reducing power consumption. That is, the controller 151 of the pedometer intermittently supplies the operational power to the acceleration sensor 153 with a predetermined time interval, thereby intermittently operating the acceleration sensor 153. FIGS. 3A to 3D are views illustrating exemplary sampled acceleration information of an acceleration sensor according to an embodiment of the present invention.

Figure 3A:
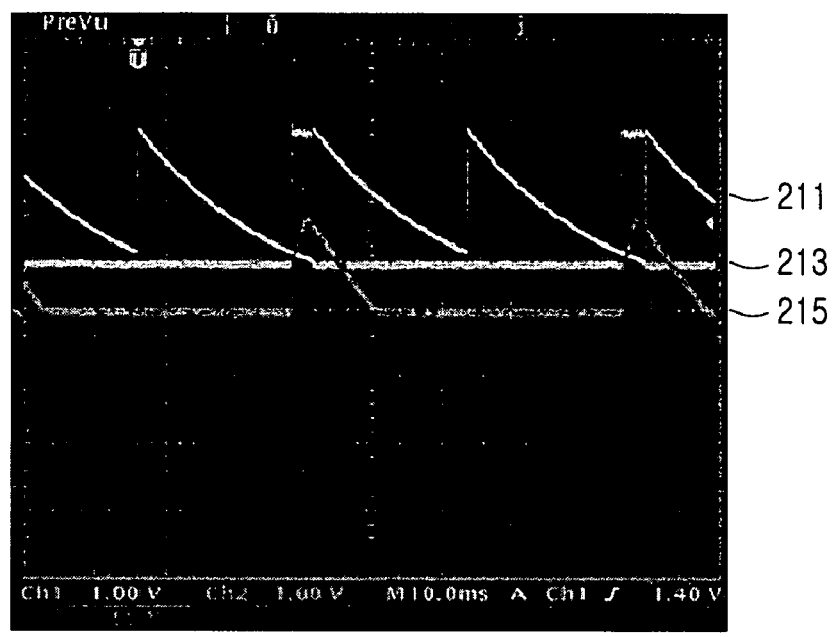
FIGS. 3A to 3D are views illustrating exemplary sampled acceleration information of an acceleration sensor according to an embodiment of the present invention.
Figure 3B:
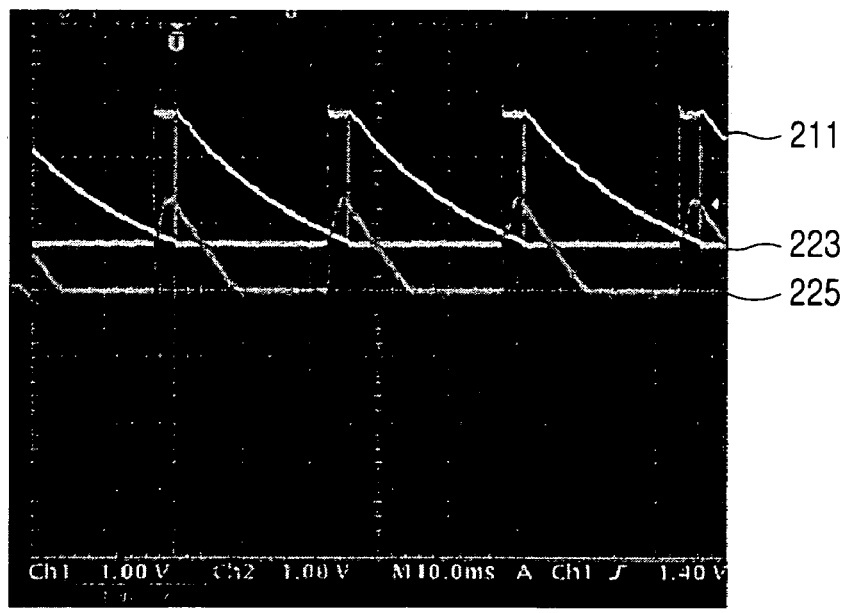

The controller 151 of the pedometer 150 controls the operation of the acceleration sensor 153 with a predetermined time interval which is set based on external resistance and capacitor. At this time, if the external resistance is approximately 1MΩ and the capacitor is approximately 22 nF, the predetermined time interval is approximately ⅓₅second. Thus, the controller 151 samples the acceleration information of X, Y and Z-axes generated from the acceleration sensor 153 while supplying the operational power to the acceleration sensor 153 with the predetermined time interval. A signal 211 shown in FIG. 3A and 3B represents the predetermined time interval determined based on the external resistance and capacitor. The signal 211 may repeat active time and power-down time and play the role of reference time for power supplied to the acceleration sensor 153. In addition, the controller 151 supplies power to the acceleration sensor 153 per every active time or per several active times according to the measurement mode, which is set by the user. FIG. 3B shows an operational characteristic when the power is supplied to the acceleration sensor 153 per every active time and FIG. 3A shows an operational characteristic when the power is supplied to the acceleration sensor 153 per every two active times.

Figure 3C:
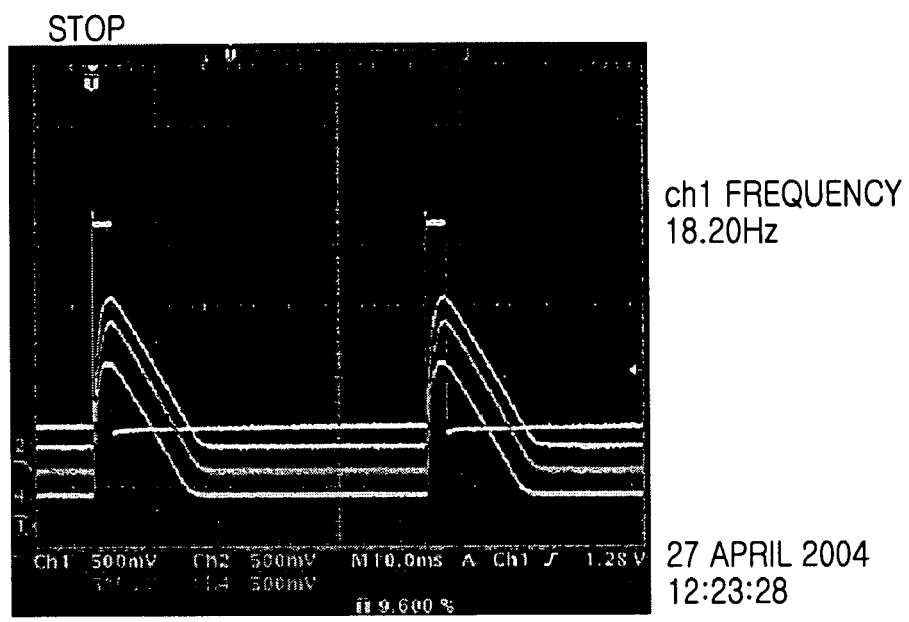

Referring to FIG. 3A, when a signal in the form of reference numeral 211 is generated, the controller 151 supplies a power signal 213 to the acceleration sensor 153 per every two active times. Upon receiving the power signal 213, the acceleration sensor 153 generates the acceleration information in the form of a signal 215. In addition, referring to FIG. 3B, when a signal in the form of reference numeral 211 is generated, the controller 151 supplies a power signal 223 to the acceleration sensor 153 per every active time. Upon receiving the power signal 223, the acceleration sensor 153 generates the acceleration information in the form of a signal 225. The signals 215 and 225 shown in FIGS. 3A and 3B are acceleration information of a predetermined axis (for example, an X-axis) of the acceleration sensor 153. FIG. 3C shows the acceleration information generated from three-axes (X, Y and Z-axes) of the acceleration sensor 153.

Figure 3D:
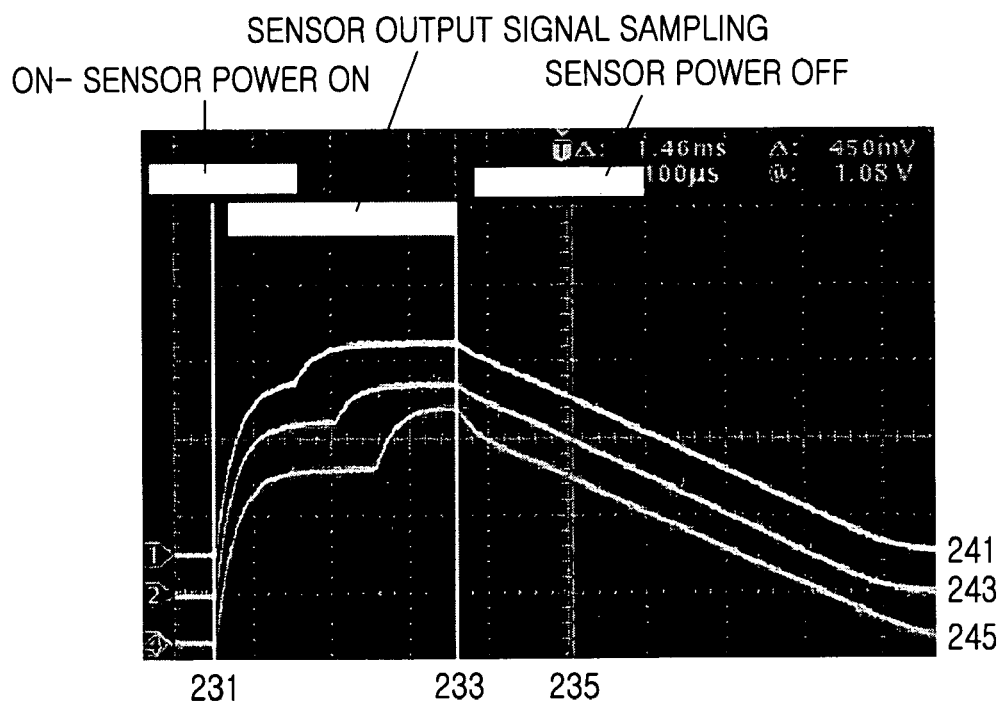

The controller 151 samples the acceleration information of the X, Y and Z-axes of the acceleration sensor 153 at a predetermined time after the acceleration sensor 153 has been powered on. FIG. 3D is a view illustrating the points where the controller 151 controls the power-on and power-off of the acceleration sensor 153 and samples the output signal of the acceleration sensor 153. Referring to FIG. 3D, the controller 151 supplies sensor power to the acceleration sensor 153 at power-on time 231. Thus, the output of the X, Y and Z-axes of the acceleration sensor 153 is gradually increased as shown by reference numerals 241, 243 and 245 and the output of the X, Y and Z-axes of the acceleration sensor 153 is stabilized at a predetermined point of time. At this time, the controller 151 samples the output of the acceleration sensor 153. That is, the controller 151 samples the output of the X, Y and Z-axes of the acceleration sensor 153 at the predetermined point of time represented by reference numeral 233 in FIG. 3D and converts the sampling voltages of the X, Y and Z-axes of the acceleration sensor 153 into digital signals by using an A/D converter. The sampling period at this time, is either ⅟₁₈ second (FIG. 3A) or ⅟₃₅ second (FIG. 3B) depending upon the sampling frequency mode. Then, the controller 151 shuts off the power being supplied to the acceleration sensor 153, thereby minimizing the power consumption of the acceleration sensor 153. That is, the controller 151 turns off the power of the acceleration sensor 153 at the predetermined point of time represented by reference numeral 233 in FIG. 3D, thereby stopping the operation of the acceleration sensor 153.

As described above, according to an embodiment of the present invention, the controller 151 intermittently controls the operation of the acceleration sensor 153, thereby reducing the power consumption of the pedometer 150.

Figure 3E:
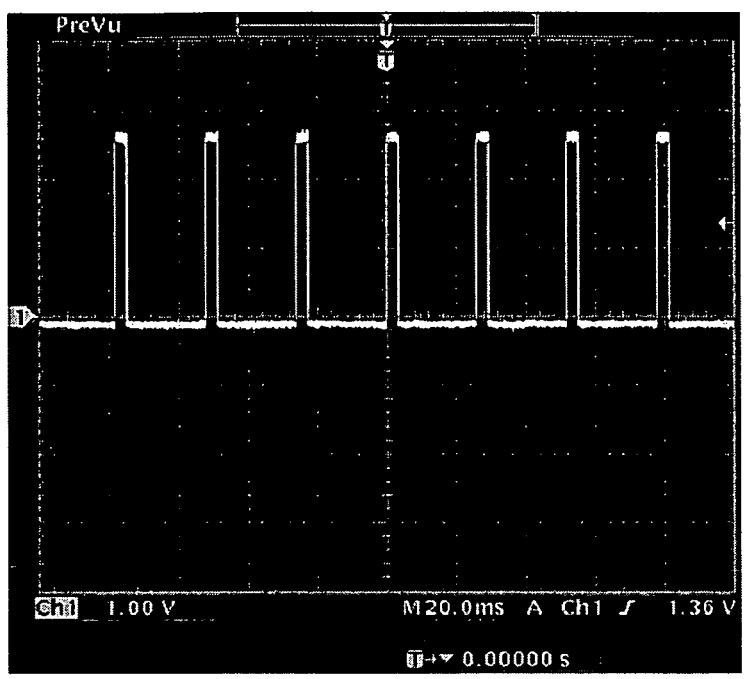
FIGS. 3E and 3F are views illustrating sampling frequencies corresponding to the types of exercise according to an embodiment of the present invention.
Figure 3F:
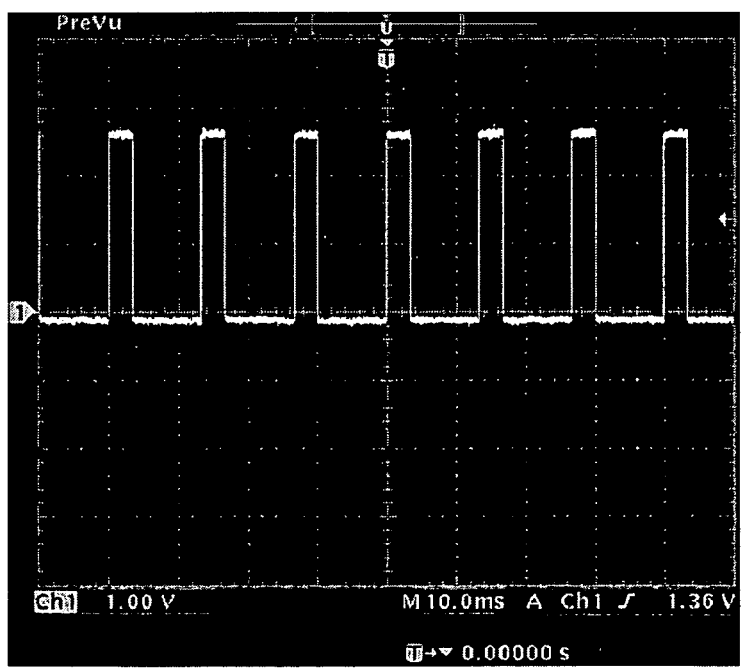

In addition, it is possible to reduce the power consumption of the pedometer by driving the acceleration sensor 153 for a predetermined period of time during the sampling interval. As shown in FIGS. 3A and 3B, since the sampling frequency mode is divided into the normal mode and the detail mode, it is possible to selectively use the sampling frequency according to the state of exercise of the user. In addition, the sampling frequency corresponding to each type of the exercise can be used. As stated above, the types of exercise includes walking, running, and so on. When the user runs, the acceleration information can be detected with a higher energy level and a short detection interval. That is, it is possible to distinguish the type of exercise being performed by the user based on a time interval between steps. Accordingly, if the sampling frequency in the running mode is higher than the sample frequency in the walking mode, the quantity of exercise can be precisely detected. Accordingly, if the type of exercise is determined to be "running", it is preferred to use the higher sampling frequency for the acceleration sensor. That is, as shown in FIG. 3E, if sampling frequencies of 38.49 Hz and 74.96 Hz are used, the sampling frequency of 38.49 Hz is used for the walking mode and the sampling frequency of 74.96 Hz is used for the running mode. That is, after checking the type of exercise performed by the user, the above sampling frequency is supplied to the acceleration sensor 153 according to the type of exercise, so that the quantity of exercise of the user can be precisely detected.

Hereinafter, the procedure for determining the step of the user by analyzing the acceleration information of the X, Y and Z-axes of the acceleration sensor 153 will be described.

If sampling voltages of the X, Y and Z-axes of the acceleration sensor 153 are Vx, Vy and Vz, respectively, the sampling voltages Vx, Vy and Vz and accelerations Ax, Ay and Az applied to three-axes of the acceleration sensor 153 may satisfy Equation 2.

$$V_x=0.2A_x+0.5V_{DD}, V_y=0.2A_y+0.5V_{DD}, V_z=0.2A_z+0.5V_{DD}$$ Equation 2

Accordingly, in order to obtain the accelerations Ax, Ay and Az by using the sampling voltages Vx, Vy and Vz, Equation 3 is used.

$$A_x=5(V_x-0.5V_{DD}), A_y=5(V_y-0.5V_{DD}), A_z=5(V_z-0.5V_{DD})$$ Equation 3

In Equation 3, the units of sampling voltages Vx, Vy and Vz and accelerations Ax, Ay and Az are V and m/s$^2$, respectively. In addition, $V_{DD}$ is the supply voltage for the acceleration sensor, typically, 2.8V in a portable terminal.

After that, the acceleration information is accumulated for the purpose of performing a discrete cosine transform (DCT). Thus, the latest eight acceleration data samples are accumulated. That is, the latest eight acceleration data samples of X, Y and Z-axes are accumulated and stored. In addition, the accumulated acceleration data is subject to the DCT. At this time, it is possible to perform the DCT for eight acceleration data samples per each axis. The DCT can be performed according to Equation 4. In Equation 4, Ax(k) (k=0, 1, 2, 3, 4, 5, 6, 7) represents data from the latest eight acceleration data samples accumulated in the X-axis of the acceleration sensor 153, Ax(0) represents the latest acceleration information of the X-axis of the acceleration sensor 153, and Ax(7) represents the final acceleration information of the X-axis of the acceleration sensor 153. The same rule is applied to Ay(k) and Az(k).

$$P_x(k) = 2\sum_{n=0}^{7} A_x(n)\cos\frac{\pi k(n+0.5)}{8}, (k = 0, 1, 2, 3, 4, 5, 6, 7)$$

$$P_y(k) = 2\sum_{n=0}^{7} A_y(n)\cos\frac{\pi k(n+0.5)}{8}, (k = 0, 1, 2, 3, 4, 5, 6, 7)$$

$$P_z(k) = 2\sum_{n=0}^{7} A_z(n)\cos\frac{\pi k(n+0.5)}{8}, (k = 0, 1, 2, 3, 4, 5, 6, 7)$$

Equation 4

After performing the DCT for the accumulated acceleration information by using Equation 4, the energy values is extracted from DCT information. That is, the controller 151 calculates the energy value based on the Px(k), Py(k) and Pz(k) according to Equation 5. At this time, the controller 151 calculates the energy value for a specific band only.

$$E = \sum_{k=1}^{5} (|P_x(k)| + |P_y(k)| + |P_z(k)|)$$ Equation 5

As described above, the controller 151 repeatedly samples the signals in each sampling interval, converts the sampling signals into acceleration signals, performs the DCT with respect to the accumulated acceleration signals and extracts the energy from the DCT information. The energy information obtained through the above procedure can be represented in the form of a graph as shown in FIG. 4.

The controller 151 converts the data from the latest eight data samples of X, Y and Z-axes into frequency components in every active time or every predetermined active time by using the DCT (8-point DCT). At this time, DC acceleration components are removed from the frequency components. Thus, the influence caused by the acceleration of gravity will also be removed. This is for obtaining acceleration variation derived from the movement of the user regardless of the angle and position of the portable terminal. Then, the controller extracts the AC acceleration components and combines the data of the three-axes (X, Y and Z). The combined data are dynamic energy components representing the level of acceleration derived from the movement of the user.

Figure 4:
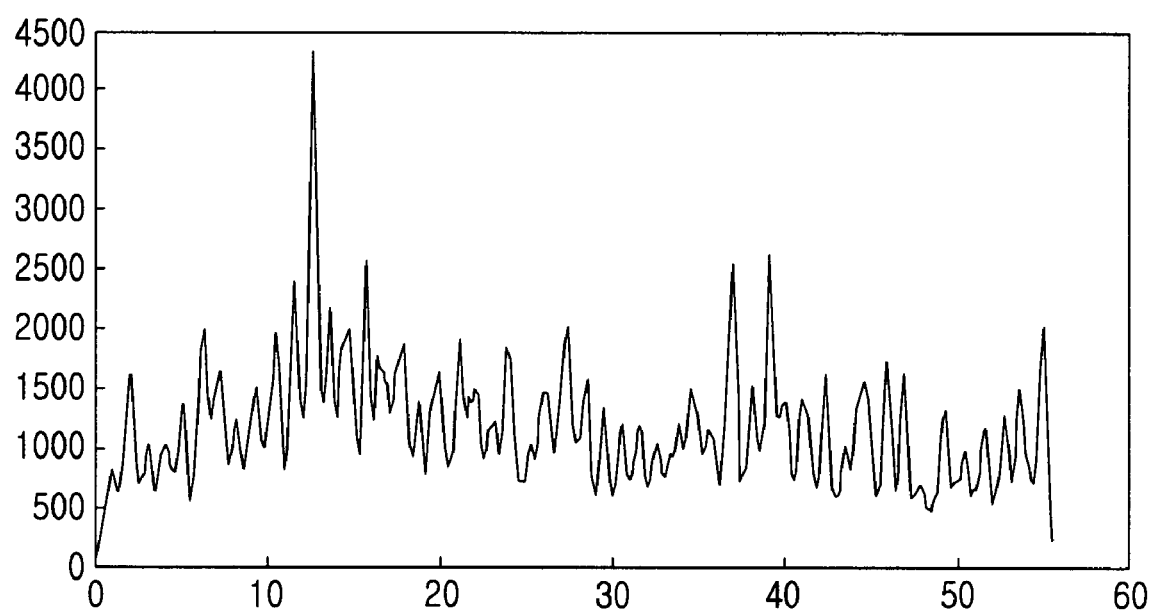
FIG. 4 is a graph illustrating energy information related to the quantity of exercise detected by a pedometer according to an embodiment of the present invention.
Figure 5:
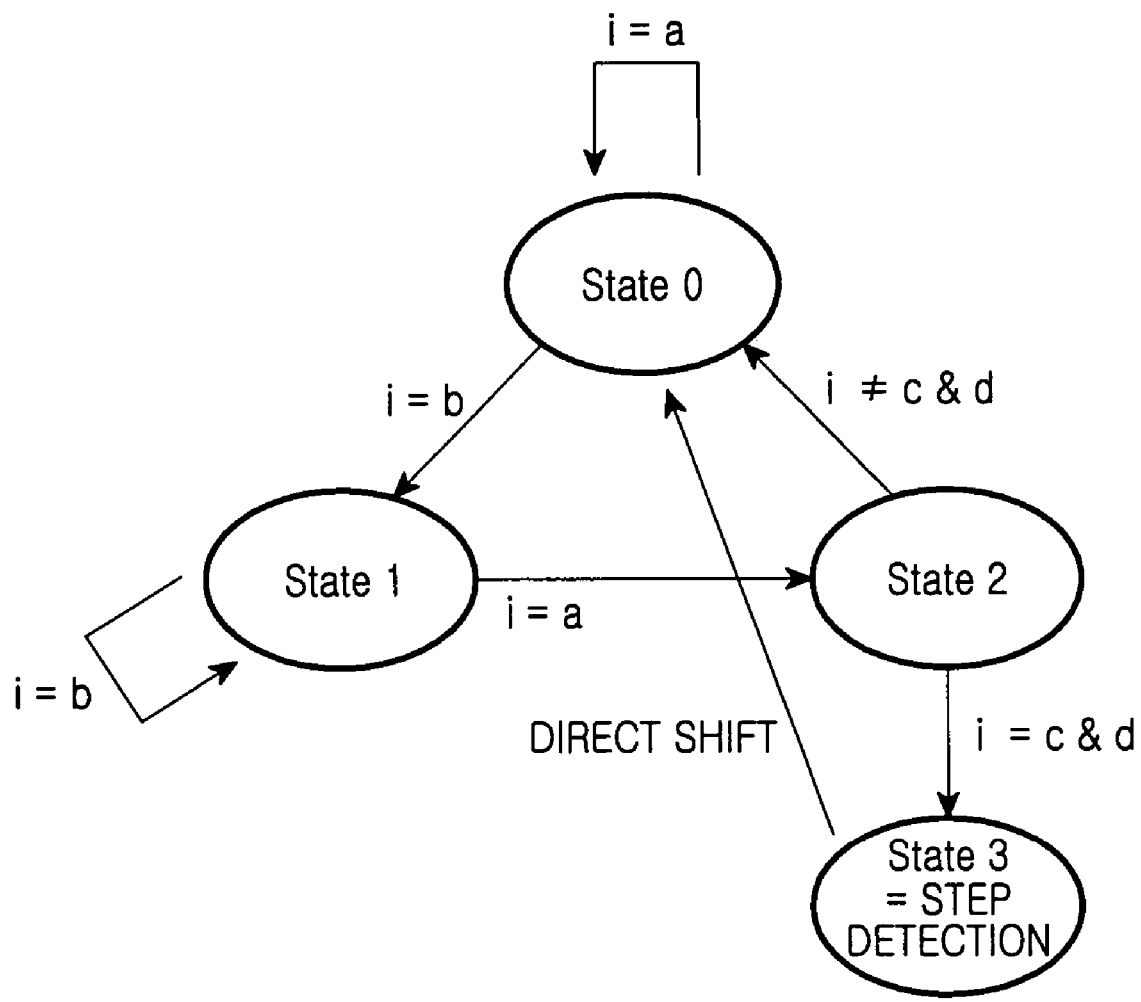
FIG. 5 is a state machine view for detecting the steps of a user by analyzing the energy information related to the quantity of exercise detected from a pedometer according to an embodiment of the present invention.

Thus, the controller determines whether the user walks by analyzing the extracted energy components as shown in FIG. 4. Such a determination can be carried out by using the state-machine as shown in FIG. 5. FIG. 5 is a state machine view for detecting steps of the user according to an embodiment of the present invention. State transition may occur under four conditions as shown in Table 2.

TABLE 2

| Input | Explanation | Note |
|---|---|---|
| a | Predetermined latest energy data have local maximum value | Condition 1 |
| b | Ascending gradient of predetermined latest energy data has value exceeding predetermined value | Condition 2 |
| c | Local maximum value has value exceeding a predetermined energy value | Condition 3 |
| d | Predetermined time has lapsed after state 3 | Condition 4 |

Figure 6:
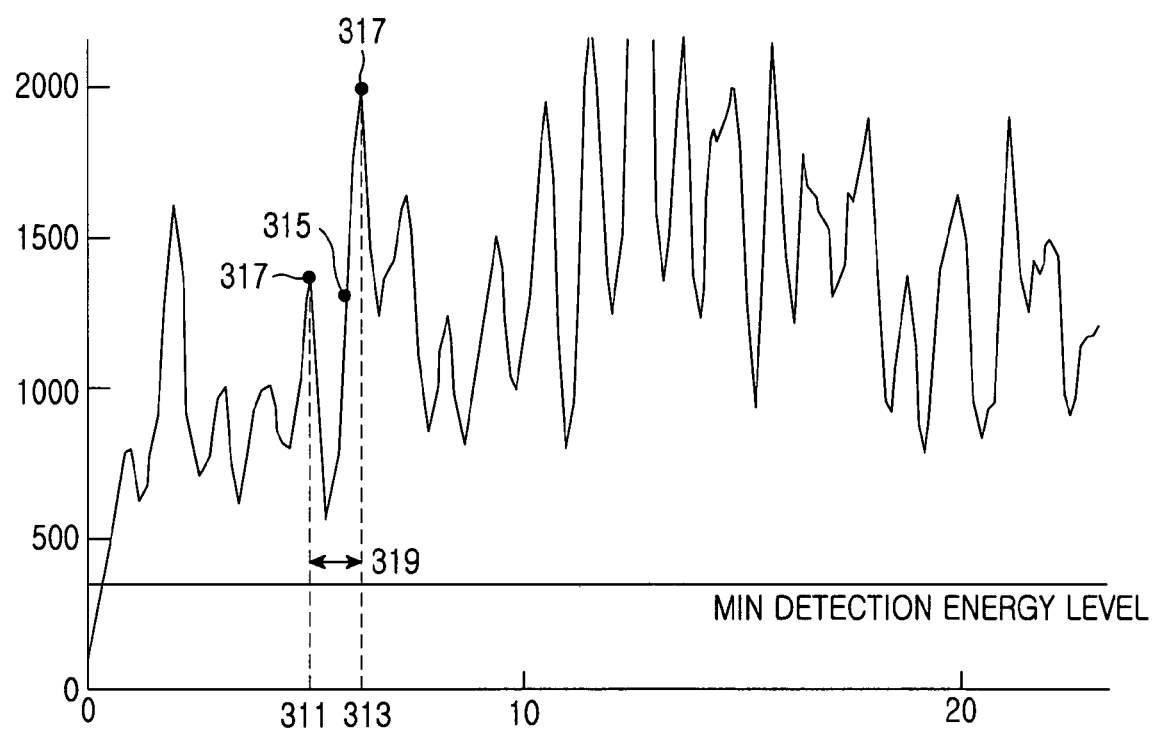
FIG. 6 is a graph illustrating the parameters for determining the number of steps based on the energy information related to the quantity of exercise according to an embodiment of the present invention.

The minimum values for the parameters represented in Table 2 can be obtained by using energy information extracted through an experiment. FIG. 6 is a view for explaining the input parameters shown in Table 2. The embodiments of the present invention employ a plurality of parameters for determining the steps of the user. According to an embodiment of the present invention, four parameters are employed as represented in Table 2.

Referring to FIG. 5, in state 0, if the ascending gradient of the predetermined energy data has a value exceeding the predetermined value, that is, if condition 2 is satisfied, the controller 151 is switched into state 1. In addition, if the predetermined energy data have a local maximum value, that is, if condition 1 is satisfied, the controller 151 is switched into state 2. Then, it is checked whether the local maximum value exceeds a predetermined energy value under state 2 and whether predetermined time has lapsed after state 3 (conditions 3 and 4). If conditions 3 and 4 are not satisfied under state 2, the controller 151 is switched into state 0. However, if conditions 3 and 4 are satisfied under state 2, the controller 151 is switched into state 3, determining the present energy information as a step of the user. After that, the controller 151 is switched into state 0 from state 3 in order to repeat the above procedure.

Referring to FIGS. 5 and 6, in state 0, if the ascending gradient of the energy information has a value exceeding a predetermined value as represented by reference numeral 313, the controller 151 is switched into state 1. The controller 151 is maintained in state 1 until the energy information has the local maximum value as represented by reference numeral 317. If the energy information has the local maximum value 317, the controller 151 is switched into state 2. In state 2, if the local maximum value 317 exceeds the predetermined energy value (minimum detection energy level) and time spent for shifting from previous state 3 to present state 3 exceeds a predetermined time interval as represented by reference numeral 319, the controller 151 is switched into state 3 and determines the energy information that represents the step of the user. Then, the controller 151 is switched into state 0. The controller 151 maintains state 0 until the energy information value has the ascending gradient. That is, according to an embodiment of the present invention, after determining the energy information that represents the step of the user, the controller 151 waits for a predetermined period of time until the energy information has the ascending gradient. If the energy level is switched into the ascending gradient, the controller 151 waits for a predetermined period of time until the energy information has the maximum local value 317. In addition, if the energy information has the maximum local value 317, the controller 151 checks whether the local maximum value exceeds the predetermined energy value and whether the time has lapsed from the predetermined point of time determining the step of the user. If the above two conditions are satisfied, the controller 151 determines the energy information that represents the step of the user.

Figure 7A:
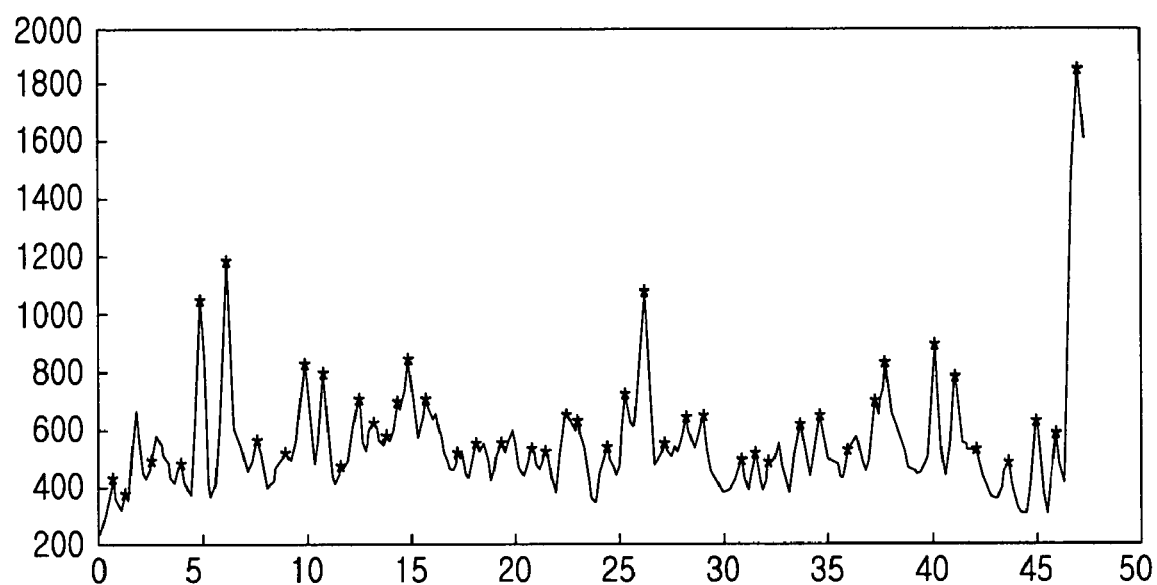
FIGS. 7A to 7C are views illustrating methods for determining the number of steps based on a factor according to an embodiment of the present invention.
Figure 7B:
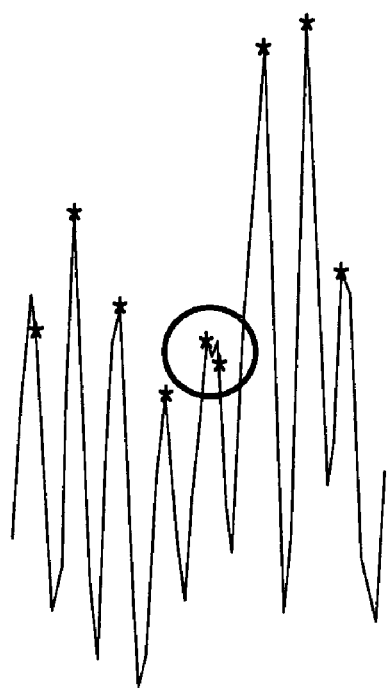
Figure 7C:
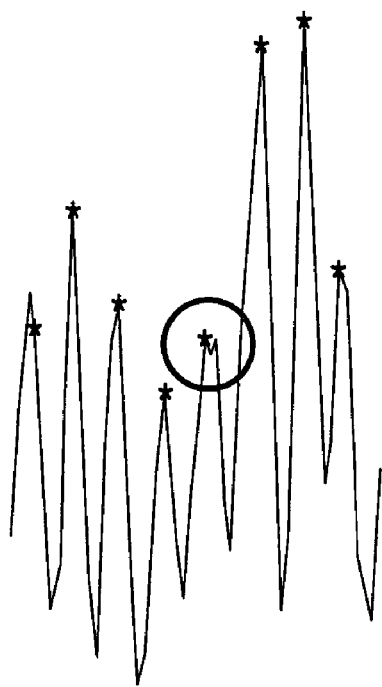

As described above, in order to determine the step of the user, the controller 151 forms the state machine as shown in FIG. 5 and detects variations of the dynamic energy based on the state machine to check whether the variations of the energy pattern represents the step of the user. If the variation of the energy pattern represents the step of the user, the pedometer 150 precisely measures the steps of the user by using several parameters (conditions). The above measurement method employs the time interval parameter and the factor of the threshold value. The time interval parameter is used for preventing the pedometer from over-counting the user's step. In general, a person can make four steps per one second if the person is moving rapidly. Thus, it is necessary to disregard the dynamic energy pattern if the dynamic energy pattern occurs within 250 ms after state 3 shown in FIG. 5 even if the dynamic energy pattern corresponds to the step of the user. That is, if the time interval parameter is not used, the energy information can be erroneously determined as the step of the user as shown in FIG. 7B although it must not be treated as the step of the user. Thus, the energy information shown in FIG. 7B must be treated in a manner as shown in FIG. 7C. In addition, the threshold value parameter is used for allowing the pedometer to count the user's step only when the energy variation exceeds a predetermined level. That is, even when the dynamic energy pattern corresponds to the step of the user, if an absolute value of the dynamic energy is less than the factor of the threshold value (that is, the minimum detection energy level shown in FIG. 6), the threshold value parameter allows the pedometer to determine the dynamic energy pattern as measurement noise of the acceleration sensor or as a minute movement by the user, so the dynamic energy pattern is not determined as representing the step of the user.

Hereinafter, a procedure of measuring the calorie consumption after the step determination procedure is performed will now be described in more detail.

If the dynamic energy value has been determined as representing a particular step of the user, the controller 151 calculates the calories consumed according to the determined step of the user. At this time, the controller 151 uses the energy level corresponding to steps of the user to calculate the calories consumed. The energy level is divided into several sections according to the type of exercise performed by the user, such as running at full speed, jogging, normal walking and slow walking.

Figure 8A:
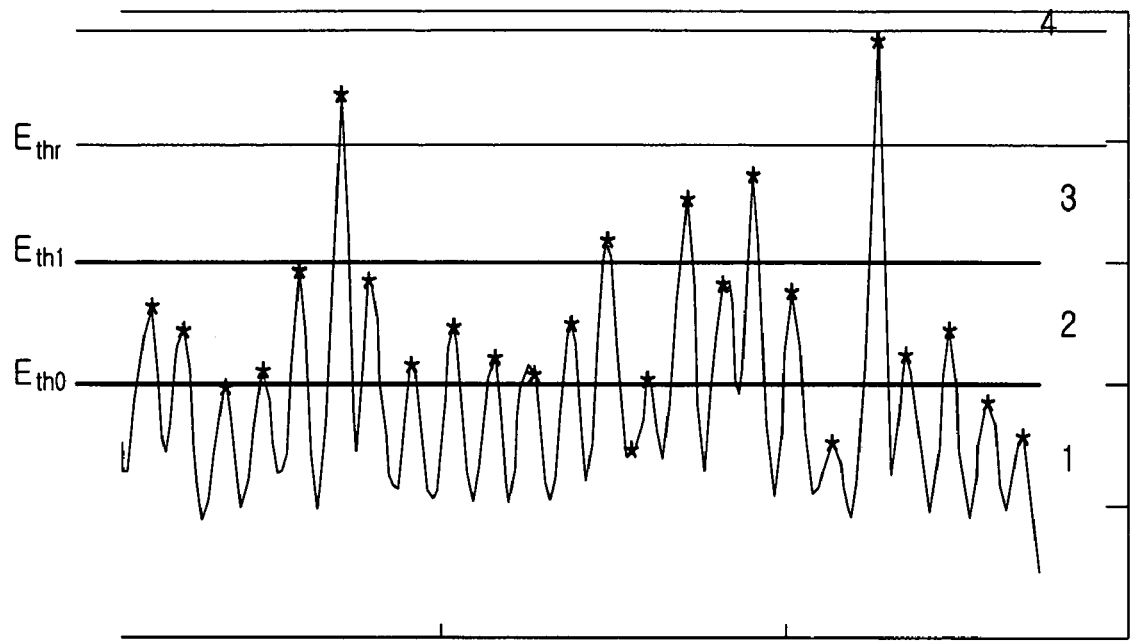
FIG. 8A is a view illustrating an example for calculating calorie consumption based on an energy level of measured quantity of exercise according to an embodiment of the present invention.

FIG. 8A is a view illustrating exemplary energy level sections corresponding to the steps of the user according to an embodiment of the present invention. The energy levels shown in FIG. 8A can be represented as Equation 6.

$$Cal_{60\,Kg} = Cal_{60\,Kg} + Cal_{NEW}(E_{MAX})$$

$$Cal_{NEW}(E_{MAX}) = \begin{cases} 0.08(\text{cal}), & E_{MAX} < E_{th0} \\ 0.06(\text{cal}), & E_{th0} \leq E_{MAX} < E_{th1} \\ 0.04(\text{cal}), & E_{th1} \leq E_{MAX} < E_{th2} \\ 0.02(\text{cal}), & E_{th2} \leq E_{MAX} \end{cases}$$

$E_{max}$: maximum energy level for steps of user;
$E_{th0-2}$: constant for setting the energy level section;
$Cal_{60\,Kg}$: factor for calorie calculation;
In this case, the calorie consumption when the weight of the user is 60 Kg; and
$Cal_{NEW}(E_{maximum})$: calorie consumption for one step.

Referring to FIG. 8A and Equation 6, $E_{th0-2}$ which is the constant for setting the energy level section is obtained through experimentation. That is, the energy value may vary depending on the positions of the pedometer 150, such as front or rear pockets of trousers, a pocket of a jacket, a bag, and a neck or a hand of a user and so on. The energy value obtained when the user exercises with the pedometer in the pocket of the trousers may be different from the energy value obtained when the user exercises while gripping the pedometer. For this reason, the energy level for the steps of the user is measured while placing the pedometer in various positions and enabling the user to run or walk predetermined distances within a predetermined time as shown in Table 3. At this time, after combining $E_{max}$ values corresponding to the steps of the user, the total $E_{max}$ value is divided by the number of steps, thereby obtaining an average $E_{max}$ value. Thus, $E_{th0-2}$ used for setting the energy level section, such as running at full speed, jogging, normal walking and slow walking, can be determined based on the average $E_{max}$ value, which is obtained by repeating the above described experiments. Therefore, the value of $E_{th0-2}$ may vary depending on the position of the pedometer on the user.

TABLE 3

| Lapse time for 100 m | Type of exercise |
| --- | --- |
| Less than 17 seconds | Running at full speed |
| 17 to 30 seconds | Jogging |
| 30 to 60 seconds | Fast walking |
| Above 60 seconds | Walking |

After obtaining the average $E_{max}$ value, the calorie consumption per one step of the user is calculated based on the calorie consumption information per one step according to the type of exercise. The calorie consumption per one step of the user is accumulated and divided by the total steps of the user according to the type of exercise, thereby obtaining the average calorie consumption per one step as shown in Table 4.

TABLE 4

| Type of exercise | Calorie consumption (60 kg) | FIG. 8A |
| --- | --- | --- |
| Running at full speed | 80 cal/one step | Section 4 |
| Jogging | 60 cal/one step | Section 3 |
| Fast walking | 40 cal/one step | Section 2 |
| Walking | 20 cal/one step | Section 1 |

If a weight value per one step (for a user weighing 60 kg and running at full speed, the weight value is 80 cal/one step) shown in Table 4 is added to every step of the user, an accumulation value of calorie consumption may vary according to strength of the dynamic energy, that is, calorie consumption of the user who walks predetermined steps is different form calorie consumption of the user who runs the same steps. In general, if a person having a weight of 60 kg normally walks 10,000 steps, the calorie consumption is about 400 kcal. Thus, it is necessary to statistically match calorie consumption resulted from walking with calorie consumption resulted from running by taking the accumulated weight value and the number of steps into consideration. In addition, the calorie consumption of persons may vary according to the height and weight of the user even if they perform the same type of exercise. Table 5 shows a relationship between the weight and calorie consumption of the user, which is obtained through experimentation.

TABLE 5

| | 45 kg | 50 kg | 56 kg | 61.2 kg | 67.5 kg | 73 kg | 78.7 kg | 84 kg |
|---|---|---|---|---|---|---|---|---|
| Ascending stairs | 351 | 395 | 438 | 481.5 | 525 | 566 | 606 | 647 |
| Business work | 48 | 54 | 60 | 66 | 72 | 78 | 84 | 90 |
| Cleaning work | 90 | 102 | 114 | 126 | 138 | 149 | 159 | 164 |
| Base ball | 138 | 156 | 174 | 192 | 210 | 228 | 246 | 263 |
| Swimming | 78 | 87 | 98 | 105 | 114 | 125 | 135 | 146 |

Figure 8B:
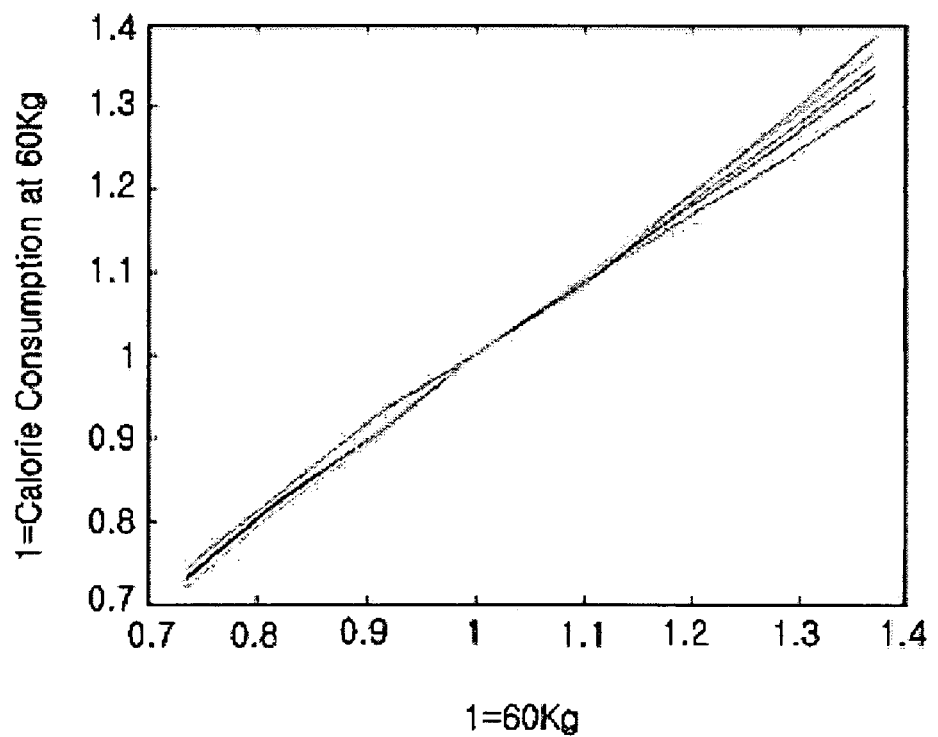
FIG. 8B is a graph illustrating calorie consumption between persons who have a standard weight and a non-standard weight, respectively, according to an embodiment of the present invention.

Based on data shown in Table 5, the calorie consumption of a person having a weight of 60 kg can be represented in the form of a graph as shown in FIG. 8B. As shown in FIG. 8B, the calorie consumption is proportional to the weight of the person. Thus, if the pedometer 150 shows calorie consumption of $Cal_{60\ kg}$ for the person having the weight of 60 kg, calorie consumption $Cal_M$ of a person having a weight of Mkg can be obtained through Equation 7. According to an embodiment of the present invention, calorie consumption for the standard weight of 60 kg is first calculated and the calorie consumption corresponding to the weight of the user is finally calculated using Equation 7.

$$Cal_M = Cal_{60\ kg} \times \frac{M}{60\ Kg} \qquad \text{Equation 7}$$

$Cal_M$: calorie consumption of a person having a weight of Mkg $Cal_{60\ kg}$: calorie consumption obtained through Equation 6

Hereinafter, a procedure of accumulating and managing the steps and calorie consumption of the user will be described in more detail.

According to an embodiment of the present invention, the quantity of exercise (that is, the number of steps) and calorie consumption resulting thereof measured by the pedometer are accumulated and managed. To this end, the memory unit 130 is provided to accumulate and manage the output of the pedometer. The memory unit 130 includes a time memory (AM 1 to PM 12), a day memory (1 to 31 days) and a month memory (January to December), wherein the above memories store the steps of user and calorie consumption, respectively.

Thus, the number of the steps and the calorie consumption obtained through the second and third procedures are accumulated and stored in the corresponding region of the time memory. The steps of the user and calorie consumption according to the exercise of the user are sequentially stored in the corresponding regions of the time memory. In addition, if the date is changed, the steps of the user and calorie consumption (data for 24 hours) stored in the time memory are accumulated and stored in the corresponding region of the day memory. If the month is changed, the steps of the user and calorie consumption (data for 31 days) stored in the day memory are accumulated and stored in the corresponding region of the month memory. Accordingly, the quantity of exercise and the calorie consumption of the user can be managed in terms of the time, day and month thereof, so that the user can selectively check the daily or monthly quantity of exercise and calorie consumption of the user, if necessary.

FIG. 9 is a flowchart illustrating the procedure of measuring quantity of exercise and calorie consumption by controlling the acceleration sensor 153 using the controller 151 of the pedometer.

Referring to FIG. 9, the controller 151 of the pedometer measures the quantity of exercise and calorie consumption of the user while controlling the acceleration sensor 153. At this time, the controller 151 samples the output of the acceleration sensor 153 while controlling power applied to the acceleration sensor 153 according to the operation mode thereof. That is, if the operation mode is the normal measurement mode, the controller 151 supplies power to the acceleration sensor 153 as shown in FIG. 3A. In addition, if the operation mode is the detail measurement mode, the controller 151 supplies power to the acceleration sensor 153 as shown in FIG. 3B. When it reaches the predetermined operational time, the controller 151 detects it (step 421) and supplies power to the acceleration sensor 153 as represented by reference numeral 231 in FIG. 3D (step 423). After that, as the output of the acceleration sensor 153 is stabilized (see, reference numeral 233 in FIG. 3D), the controller 151 receives the output of the acceleration sensor 153 by sampling the output of the acceleration sensor 153 (step 425). At the same time, the controller 151 shuts off the power being supplied to the acceleration sensor 153 (step 427). The power supply time for the acceleration sensor 153 is predetermined between reference numerals 231 and 233 such that the output of the acceleration sensor 153 can be sufficiently stabilized.

Figure 10:
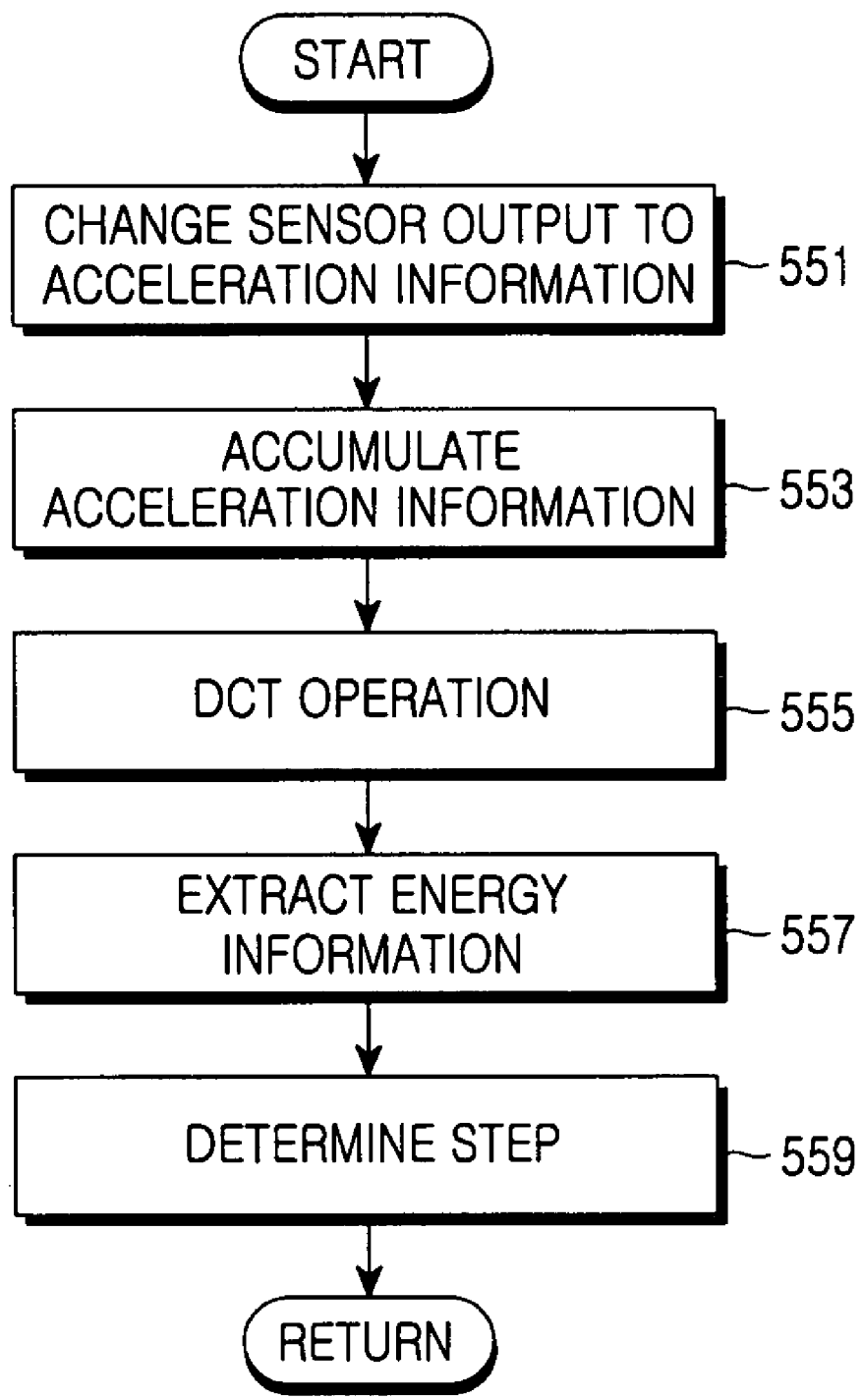
FIG. 10 is a flowchart illustrating the procedure for detecting the step of a user based on the acceleration information generated from an acceleration sensor according to an embodiment of the present invention.

After sampling and receiving the output of the acceleration sensor 153, the controller 151 analyzes the output of the acceleration sensor 153, thereby measuring the quantity of exercise (step 429). FIG. 10 is a flowchart illustrating the procedure of calculating the quantity of exercise processed in step 429 shown in FIG. 9.

Referring to FIG. 10, the controller 151 converts the output of the acceleration sensor 153 into acceleration information by using Equation 3 (step 551). Then, the controller 151 accumulates the acceleration information and performs the DCT for the accumulated acceleration information according to Equation 4 (step 555). After that, the controller 151 combines the DCT information according to Equation 5 and extracts the energy information (step 557). If a graph for the energy information is made while repeating the above procedure, the energy information as shown in FIG. 4 can be represented. In addition, based on the energy information as shown in FIG. 4, the controller 151 determines the step of the user according to the state machine as shown in FIG. 5 (step 559). At this time, the state machine shown in FIG. 5 is checked based on four parameters shown in Table 2, thereby determining the particular type of step of the user. That is, according to an embodiment of the present invention, the step represented by the energy value is determined to be the particular type of step of the user if the value of the extracted energy satisfies the time interval and the threshold value.

If the step of the user has been determined, the controller 151 detects it (step 431) and increases the number of steps by one (step 433). Then, the controller 151 calculates the calorie consumption for each type of step of the user (step 435).

FIG. 10 is a flowchart illustrating the procedure for calculating the quantity of exercise when only one sampling frequency is used. The quantity of exercise may vary depending on the type of exercise. That is, mutually different acceleration information is generated from the acceleration sensor 153 in the walking mode and the running mode. That is, in a case of the running mode, the higher signal level and the faster level trigger interval may be detected. The signal level signifies the level of the high frequency signal of DCT information. Therefore, it is preferred to allocate the sampling frequency depending on the type of exercise performed by the user. That is, after checking the type of exercise, the higher sampling frequency is applied to the acceleration sensor when the user runs and the lower sampling frequency is applied to the acceleration sensor when the user walks. In this case, it is possible to stably sample the acceleration information in the running mode.

The type of exercise performed by the user can be recognized by using high frequency components of the DCT information detected when calculating the quantity of exercise. That is, the step of calculating the quantity of exercise (step 429 in FIG. 9) may include the sub-step of extracting energy information for determining the type of step of the user as shown in FIG. 10. At this time, the DCT operation is carried out. Thus, it is possible to check the type of exercise by extracting the high frequency signal from the DCT signal. The step of establishing the sampling frequency based on the type of exercise can be performed in step 429 of FIG. 9. In addition, it is possible to establish the sampling frequency after changing information related to the number of steps of the user in step 433 or after calculating calorie consumption in step 435. According to an embodiment of the present invention, the sampling frequency is established according to the type of exercise when determining the step of the user by calculating the quantity of exercise as shown in FIG. 11.

Figure 11:
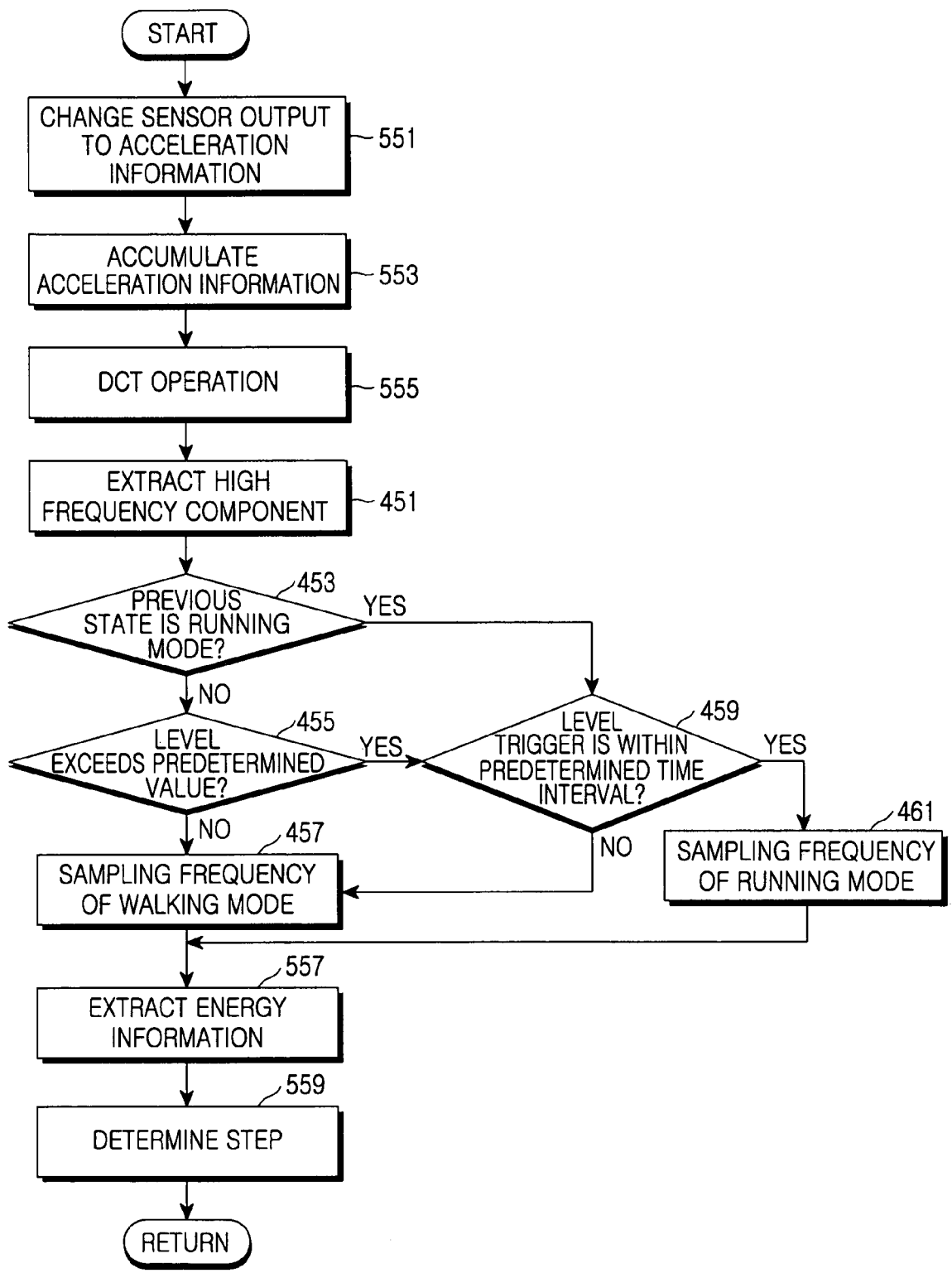
FIG. 11 is a flowchart illustrating the procedure for determining whether a user takes a step by analyzing the type of exercise based on acceleration information generated from an acceleration sensor according to an embodiment of the present invention.
Figure 12A:
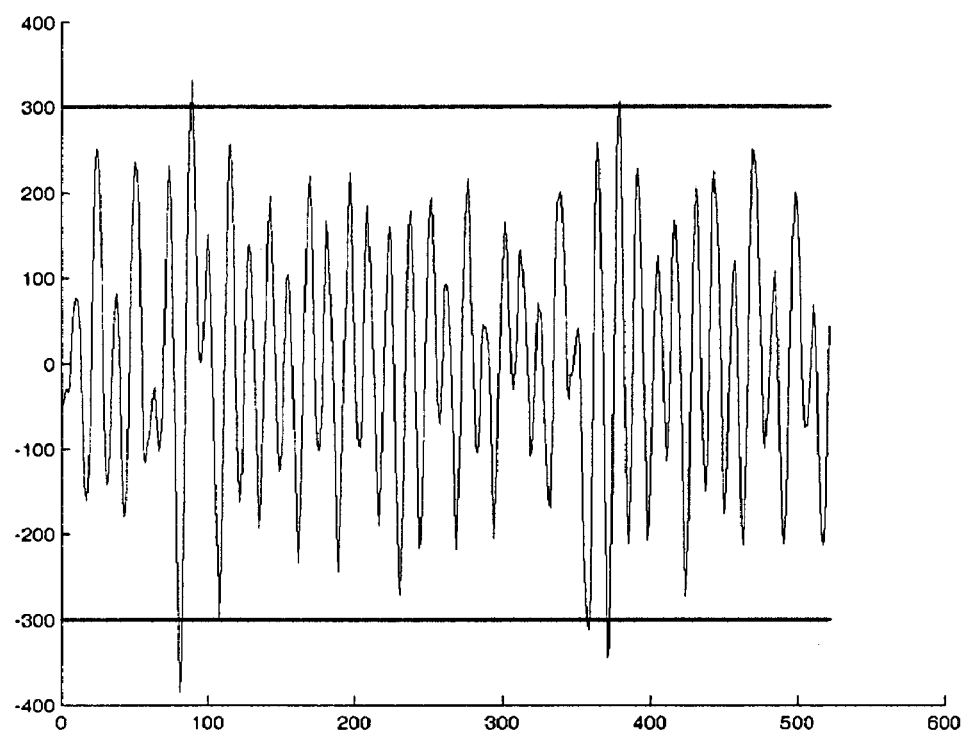
FIGS. 12A and 12B are views illustrating the energy levels and level trigger characteristics according to the type of exercise according to an embodiment of the present invention.
Figure 12B:
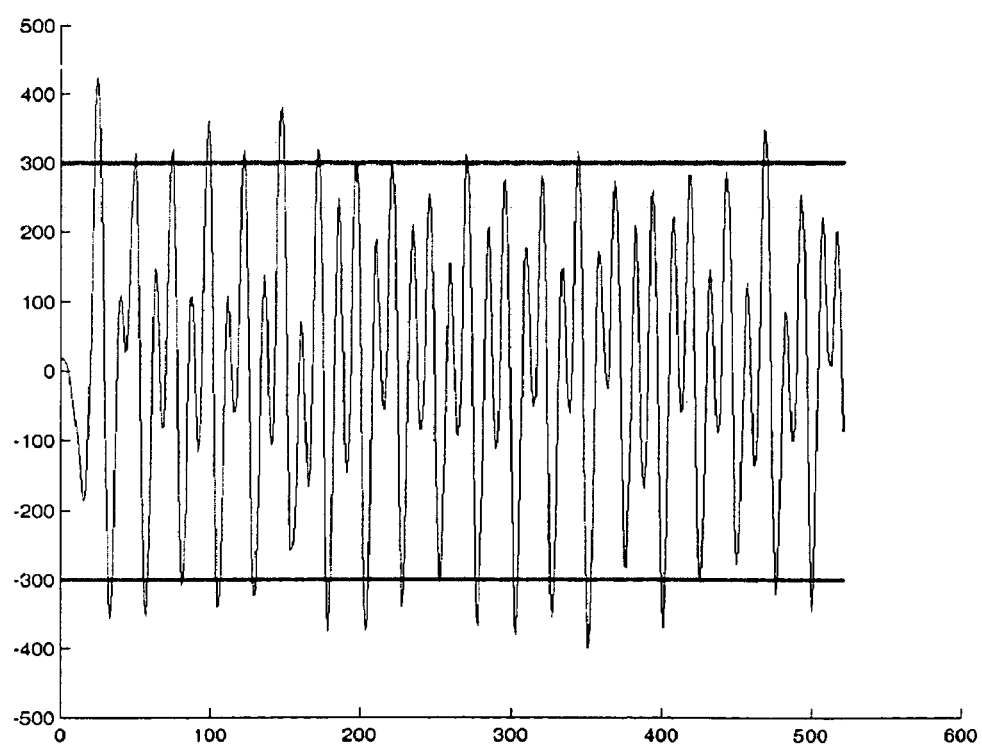
Figure 13A:
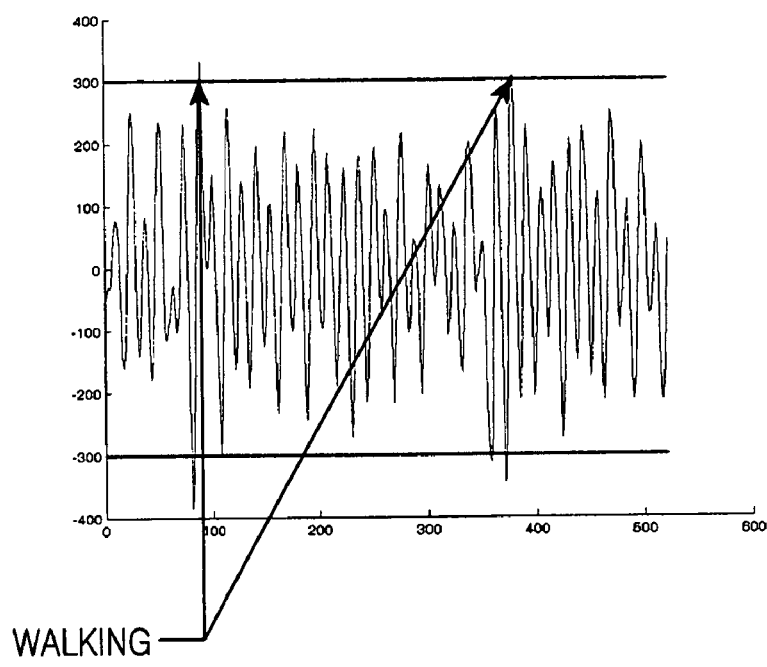
FIGS. 13A and 13B are views illustrating a method of determining the type of exercise according to an embodiment of the present invention.
Figure 13B:
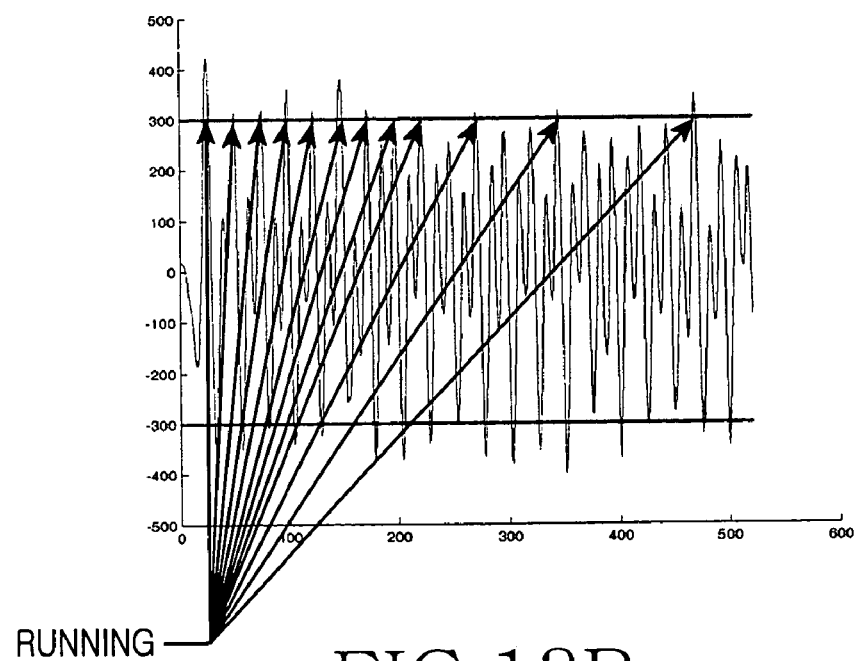

FIG. 11 is a flowchart illustrating the procedure for determining the sampling frequency by analyzing the type of exercise based on the quantity of exercise calculated in step 429 in FIG. 9. In FIG. 11, the type of exercise is "running" and "walking". FIGS. 12A and 12B are views illustrating characteristics of the DCT high frequency signal according to the type of exercise (running and walking), and FIGS. 13A and 13B are views illustrating a method of determining the type of exercise (running and walking).

FIG. 12A shows the characteristics of the DCT high frequency signal in the walking mode and FIG. 12B shows the characteristics of the DCT high frequency signal in the running mode. The high frequency signal detected in the running mode has a higher level and a faster level trigger time than those of the walking mode. Thus, the running mode or the walking mode can be determined by using the predetermined amplitude value, which is set to 300 in FIGS. 12A and 12B, and the level trigger time. That is, as shown in FIGS. 13A and 13B, if the predetermined amplitude value is set to 300, the level trigger exceeding the predetermined high frequency signal level may not occur in the walking mode (see, FIG. 13A). However, the level trigger exceeding the predetermined amplitude value may occur in every step in the running mode (see, FIG. 13B). That is, the level of the high frequency signal of the DCT information detected in the running mode is higher than that of the DCT information detected in the walking mode. In addition, the level trigger in the running mode is faster than the level trigger in the walking mode. In this case, if the sampling frequency, which is higher than the sampling frequency used in the walking mode, is used in the running mode, the quantity of exercise can be stably calculated in the running mode. Therefore, it is possible to obtain the reference level and reference level trigger for each type of exercise by measuring the level of the high frequency signal and the level trigger time of the DCT information according to the type of exercise (walking and running, and, if necessary, running at fill speed, jogging, fast walking and walking) and taking the mean value thereof. In addition, after storing the reference level and reference level trigger time for each type of exercise in the memory section, the acceleration information generated from the acceleration sensor 153 is compared with the stored reference level and reference level trigger time in order to determine the type of exercise performed by the user.

FIG. 11 is a flowchart illustrating the procedure for determining the sampling frequency based on the type of exercise according to an embodiment of the present invention. First, the acceleration information generated from the acceleration sensor 153 is converted into DCT information through steps 551 to 555. Then, information about the high frequency signal is extracted from the DCT information (step 451). After that, the controller 151 checks whether the previous mode is a running mode or a walking mode. If the previous mode is the walking mode, the controller 151 checks whether the present level exceeds a predetermined amplitude value (step 455). If the present level is less than the predetermined amplitude value, the controller 151 sets the sampling frequency of the walking mode (step 457), extracts energy information from the DCT information (step 557), and determines the step of the user (step 559). However, if it is determined in step 455 that the present level exceeds the predetermined amplitude, the controller 151 checks whether the level trigger is achieved within a predetermine period of time (step 459). If the level trigger time exceeds the predetermined reference time, the procedure returns to step 457 so that the above procedure is repeated. That is, as shown in FIG. 13A, if the level of the high frequency signal of the DCT information is less than the predetermined amplitude, or the level trigger time exceeds the predetermined time although the level of the high frequency signal of the DCT information exceeds the predetermined amplitude, the controller 151 determines that the present mode is the walking mode, so the controller 151 sets the sampling frequency of the walking mode in step 457.

However, if the level of the high frequency signal of the DCT information exceeds the predetermined amplitude and the level trigger is achieved within the predetermined time in the walking mode, the controller 151 detects it through steps 455 to 459 and sets the sampling frequency of the running mode in step 461. After that, the controller 151 extracts the energy information from the DCT information in step 557 and determines the step of the user in step 559. In addition, if the level trigger is achieved within the predetermined time when the previous mode is the running mode, the controller 151 detects it through steps 453 to 459 and sets the sampling frequency of the running mode in step 461. After that, the controller 151 extracts energy information from the DCT information in step 557 and determines the step of the user in step 559. In this manner, if the amplitude of the high frequency signal of the DCT information has a value exceeding the predetermined level and the level trigger is achieved within the predetermined time, the controller 151 sets the sampling frequency of the running mode as shown in FIG. 13B.

In FIG. 11, steps 451 to 461 are performed after transforming the acceleration information into the DCT information. That is, according to an embodiment of the present invention, the procedure for establishing the sampling frequency must be performed after forming the DCT information by extracting the acceleration information and the established sampling frequency is used as a sampling frequency for extracting the next acceleration information. Although it has been described that the sampling frequency is established when calculating the quantity of exercise in step 429 of FIG. 9, the sampling frequency can be established after determining the step of the user or after calculating calorie consumption.

Figure 14:
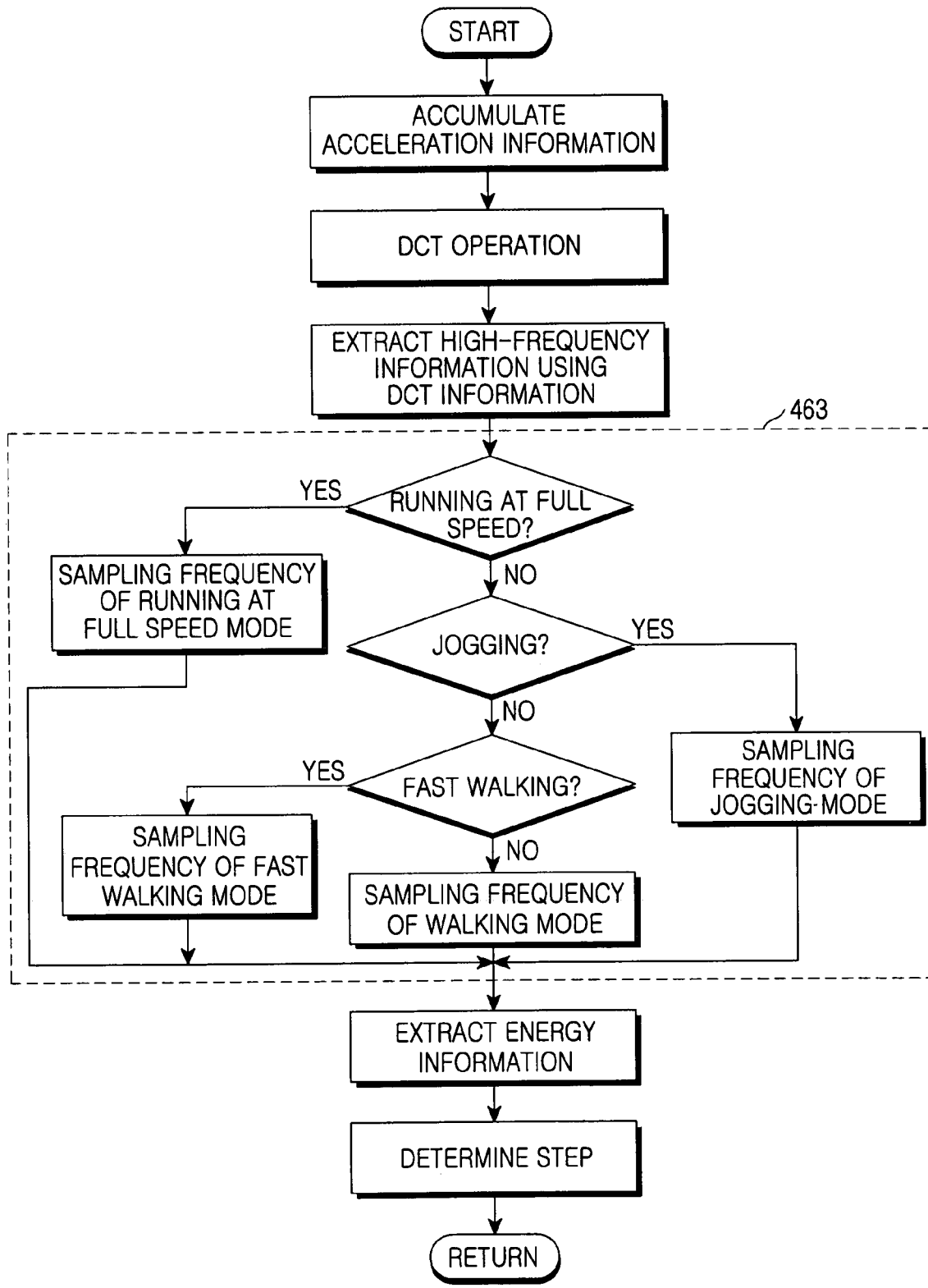
FIG. 14 is a flowchart illustrating the procedure for determining whether a user takes a step by analyzing the type of exercise based on acceleration information generated from an acceleration sensor according to another embodiment of the present invention.
Figure 15A:
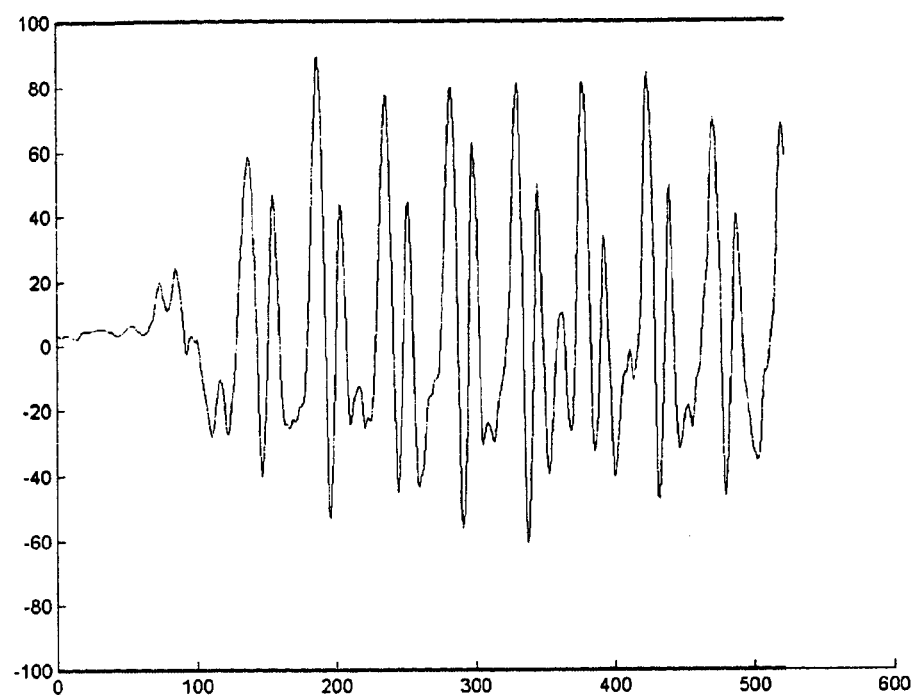
FIGS. 15A and 15B are views illustrating energy characteristics in a walking mode according to an embodiment of the present invention.
Figure 15B:
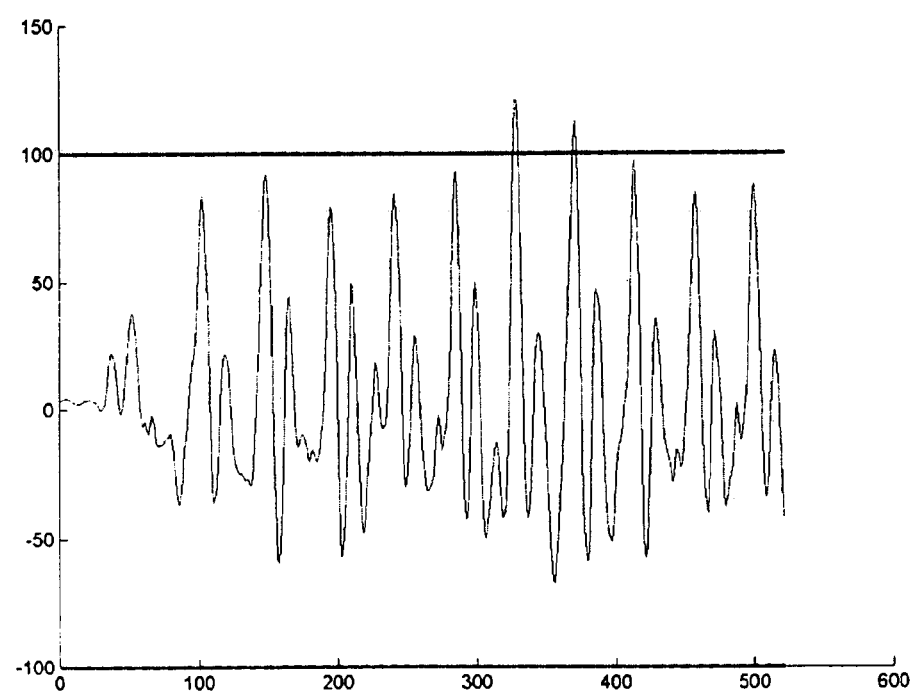
Figure 16A:
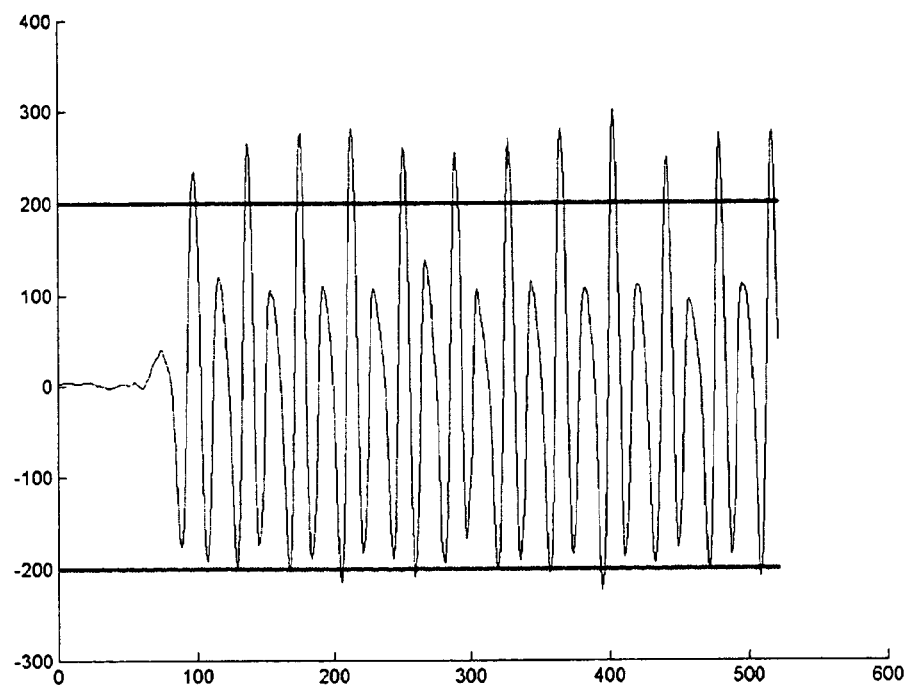
FIGS. 16A and 16B are views illustrating energy characteristics in a fast walking mode according to an embodiment of the present invention.
Figure 16B:
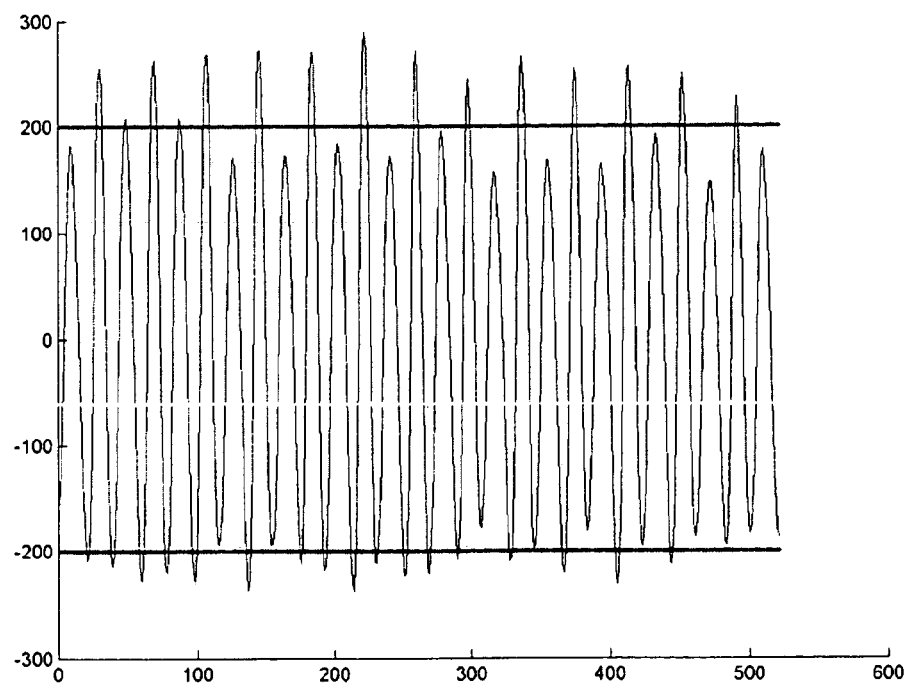
Figure 17A:
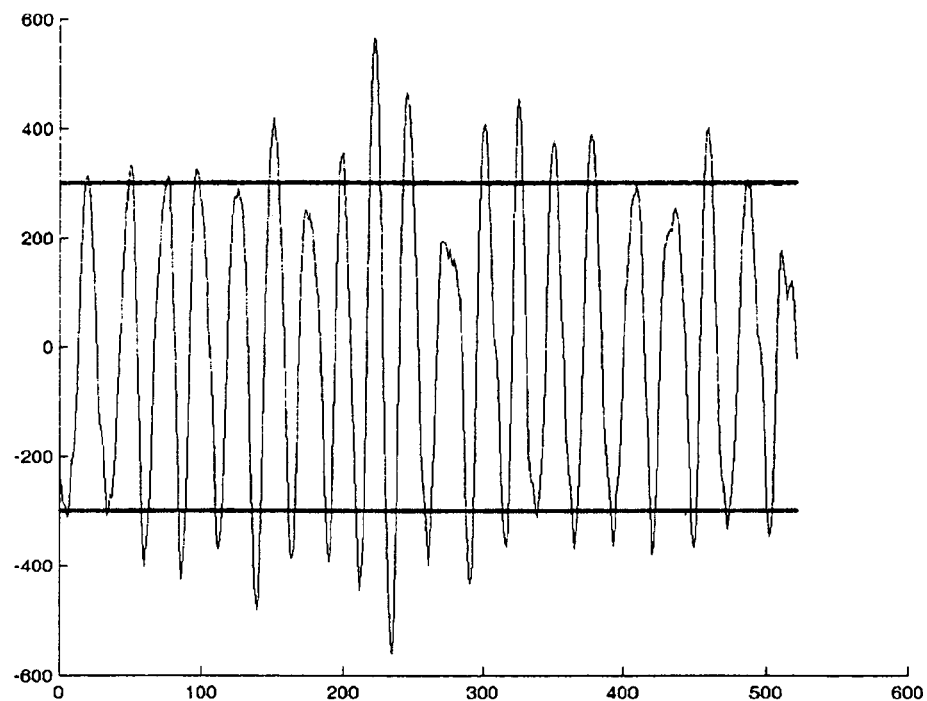
FIGS. 17A and 17B are views illustrating energy characteristics in a jogging mode according to an embodiment of the present invention.
Figure 17B:
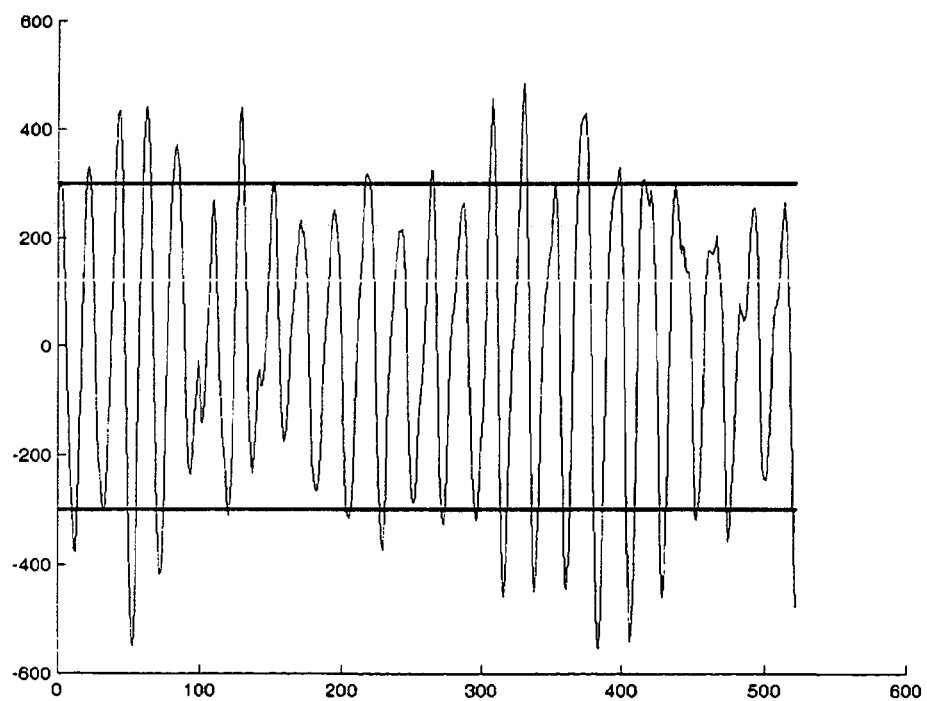
Figure 18A:
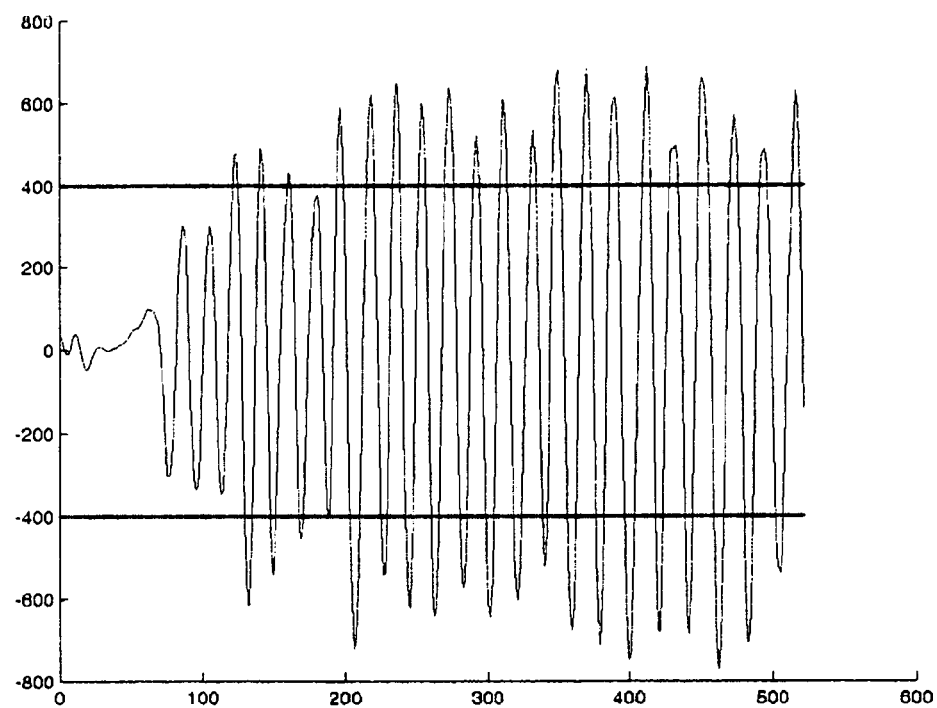
FIGS. 18A and 18B are views illustrating energy characteristics in a running mode according to an embodiment of the present invention.
Figure 18B:
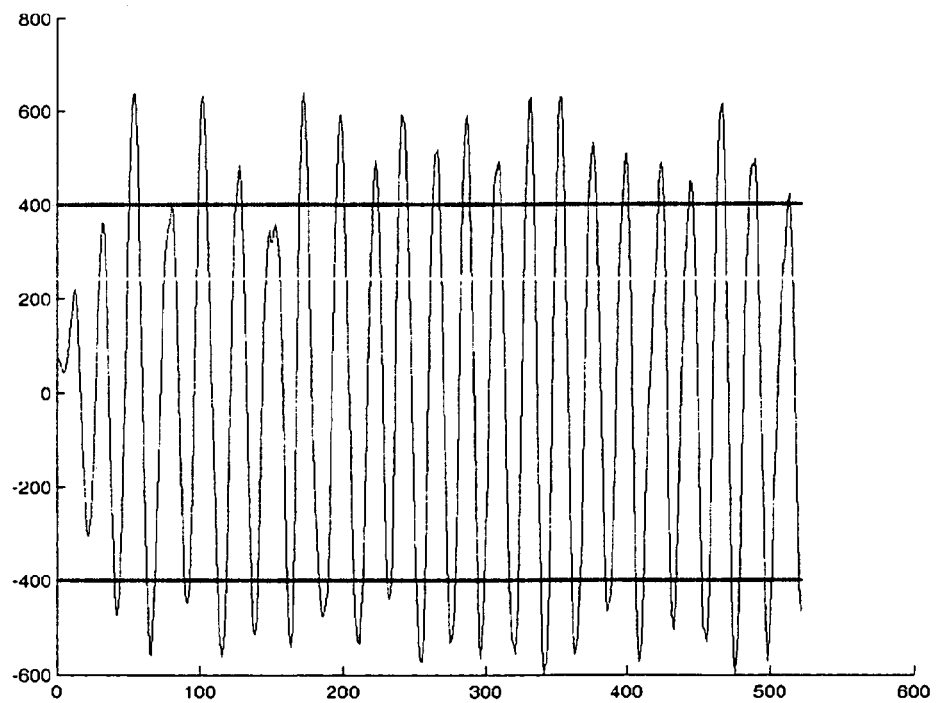

FIG. 14 is a flowchart illustrating the procedure for determining a step of a user in which the walking mode is divided into a fast walking mode and a walking mode and the running mode is divided into a running at full speed mode and a jogging mode. The steps for determining the type of step the user is taking are shown in block 463. FIGS. 15B and 15B illustrate exemplary energy characteristics in the walking mode, FIGS. 16A and 16B illustrate exemplary energy characteristics in the fast walking mode, FIGS. 17A and 17B illustrate exemplary energy characteristics in the jogging mode and FIGS. 18A and 18B illustrate exemplary energy characteristics in the running at full speed mode. As shown in FIGS. 15B to 18B, the energy level of the high frequency signal and the level trigger time may vary depending on the type of exercise. That is, in the walking mode, the high frequency signal has a small amplitude while representing a slow level trigger operation. In addition, in the running at full speed mode, the high frequency signal has a large amplitude and the level trigger operation is achieved within a short period of time. Accordingly, it is possible to establish the sampling frequency corresponding to each mode as shown in FIG. 11 if the level trigger time for each type of exercise and the level of the high frequency signal are set. In order to inspect the running at full speed mode, the jogging mode, the fast walking mode and the walking mode, the energy levels of the high frequency signals, the level trigger times and the sampling frequencies must be established corresponding to the above modes. In addition, when the high frequency signal of the DTC information is extracted, it is necessary to check whether the high frequency signal satisfies the energy level and the level trigger time for the running at full speed mode, the jogging mode, the fast walking mode and the walking mode and the sampling frequency adaptable for exercise satisfying the above two conditions is established.

After determining the step of the user in step 429 of FIG. 9 by performing the procedure shown in FIGS. 10, 11 or 14, the operations continue in FIG. 9. Where in step 443, the controller 151 changes information related to the number of steps and calculates calorie consumption caused by the step of the user in step 435. As mentioned above, the calorie consumption may vary depending on the type of exercise (running at high speed, jogging, fast walking and walking) and the attachment position of the pedometer. That is, the calorie consumption in the running at full speed mode is different from the calorie consumption in the walking mode. Thus, it is preferred to add the weight value according to the type of exercise when calculating the calorie consumption. In addition, acceleration information of the acceleration sensor 153 detected when the user performs exercise while gripping the pedometer is different from acceleration information detected by the acceleration sensor 153 when the user exercises by attaching the pedometer to the wrist or the waist. Thus, it is preferred to vary the weight value according to the attachment position of the pedometer when calculating the calorie consumption.

Figure 19:
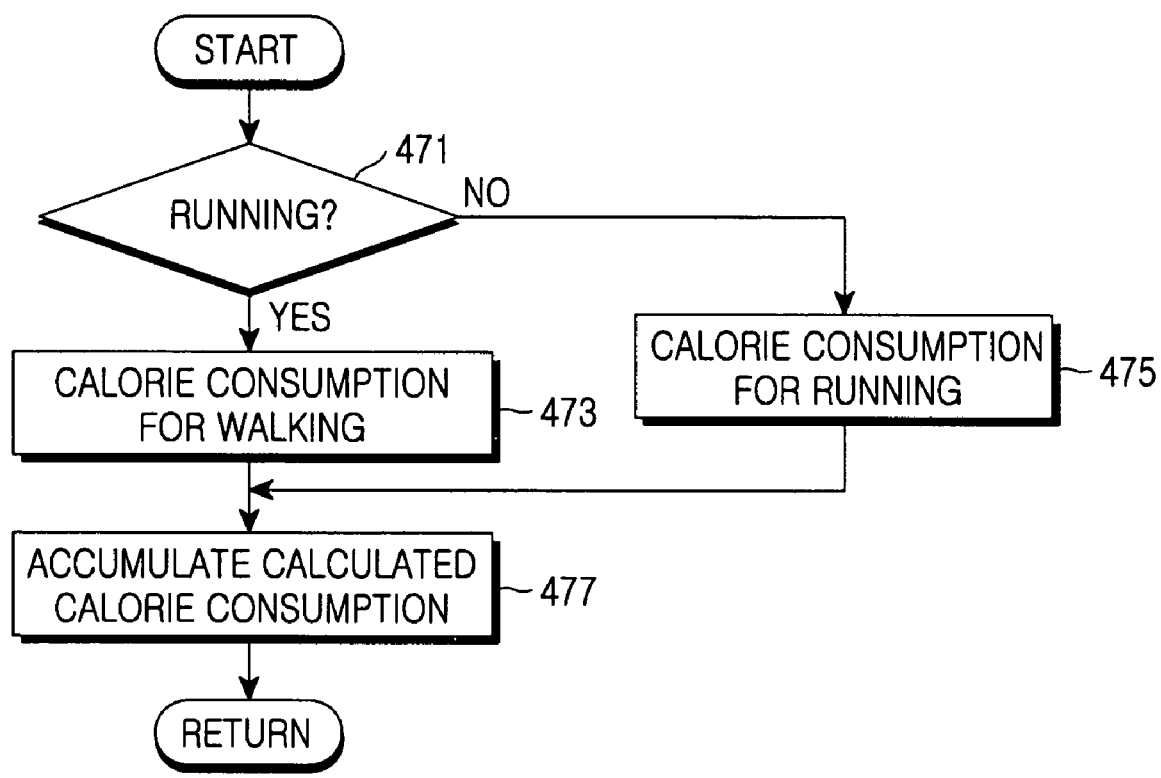
FIG. 19 is a flowchart illustrating the procedure for calculating energy consumption when the type of user step is detected in FIG. 9 according to an embodiment of the present invention.

FIG. 19 is a flowchart illustrating the procedure for calculating calorie consumption by using the pedometer when the step of the user is detected in step 435 of FIG. 9, in which the exercise mode is divided into the walking mode and the running mode similar to FIG. 11.

Referring to FIG. 19, in order to calculate the calorie consumption after the type of step of the user is detected, the controller 151 analyzes the type of exercise based on the detected step (step 471). As mentioned above, the type of exercise includes the walking and running as shown in FIG. 11. If the step of the user is determined as walking, the controller 151 calculates the calorie consumption according to the walking mode (step 473). If the step of the user is determined to be running, the controller 151 calculates the calorie consumption according to the running mode (step 475). Then, the controller 151 accumulates the calculated calorie consumption. The calorie consumption may be calculated for every step of the user. The method for calculating the calorie consumption according to the type of exercise will now be described in more detail with reference to FIGS. 20 and 21.

Figure 20:
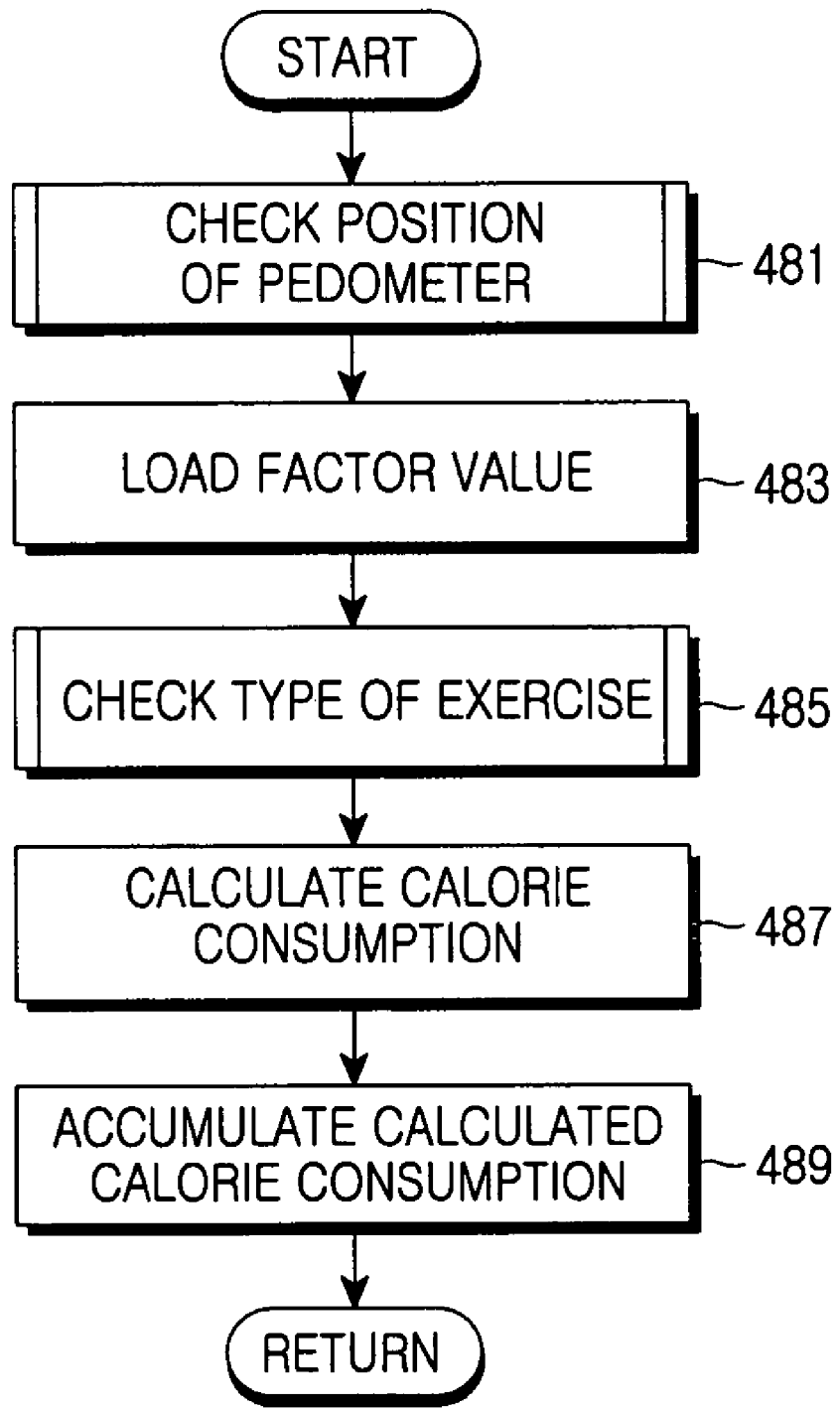
FIG. 20 is a flowchart illustrating the procedure for calculating energy consumption when the type of user step is detected in FIG. 9 according to another embodiment of the present invention.

FIG. 20 is a flowchart illustrating the procedure for calculating calorie consumption when the type of user step is detected in step 435 of FIG. 9 according to another embodiment of the present invention. That is, FIG. 20 shows the procedure for calculating the calorie consumption according to the attachment position of the pedometer and the type of exercise performed by the user. In addition, FIG. 21 shows the procedure of FIG. 20 in further detail.

Referring to FIG. 20, the controller 151 checks the attachment position of the pedometer (step 481) and loads the factor value corresponding to the attachment position of the pedometer (step 483). The attachment position of the pedometer can be selected by the user. Then, the controller 151 checks the type of exercise performed by the user (step 485) and calculates the calorie consumption according to the type of exercise performed by the user and the attachment position of the pedometer (step 487). After that, the controller 151 accumulates and stores the calculated calorie consumption.

Figure 21:
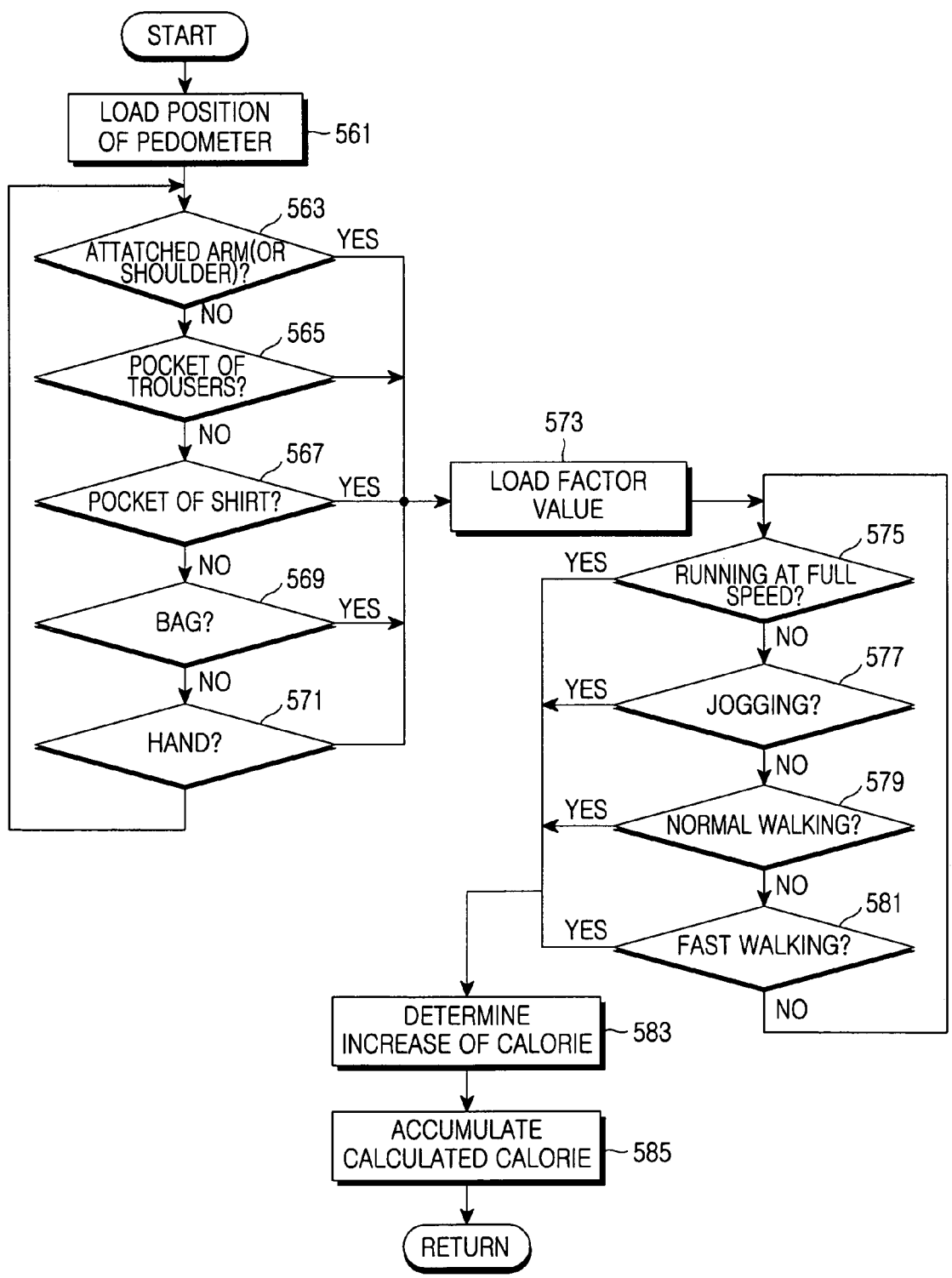
FIG. 21 is a flowchart illustrating the procedure for calculating energy consumption shown in FIG. 20 in more detail.

FIG. 21 is a flowchart illustrating the procedure of calculating the calorie consumption according to the type of user step when the step of the user has been detected. FIG. 21 shows the procedure of FIG. 20 in more detail.

Referring to FIG. 21, the controller 151 loads position information of the registered pedometer (step 561) and analyzes the attachment position of the pedometer while performing steps 563 to 571. The pedometer can be accommodated in the pockets of trousers, the pocket of the jacket and the bag and can be attached to the hand, the arm or the shoulder of the user. The attachment position of the pedometer can be selected and registered by the user or can be determined by obtaining the output characteristic of the pedometer through experimentation. That is, according to the former, the user inputs the attachment position of the pedometer by using the input section 145, and the controller 151 registers the position information of the pedometer in order to utilize the position information of the pedometer when calculating the calorie consumption. According to the latter, the user exercises with the pedometer attached to a predetermined attachment position, thereby obtaining the position information of the pedometer. For instance, the user exercises after placing the pedometer in the front pocket of the trousers, thereby obtaining a predetermined number of sample outputs. After that, the sample outputs are analyzed to determine and store front signals detected from the front pocket of the trousers of the user. After that, the output of the acceleration sensor 153 received during exercise is analyzed and is compared with the stored signals, thereby determining the attachment position of the pedometer.

If the attachment position of the pedometer is determined while performing the steps 563 to 571, the controller 151 loads a factor value according to the attachment position of the pedometer (step 573). Then, the controller 151 determines the type of exercise performed by the user according to Equation 6 by using the energy level $E_{max}$. As mentioned above, the type of exercise can be classified into running, jogging, normal walking and slow walking according to the speed of steps. Accordingly, the controller 151 determines the calorie consumption according to the energy levels of the steps by using Equation 6 and determines the type of exercise through steps 575 to 581. In addition, the controller 151 determines the calorie consumption according to the type of exercise based on Table 4 (step 583). Table 4 shows the calorie consumption per one step according to the type of exercise. In addition, the controller 151 adds the measured calorie consumption to the accumulated calorie consumption.

The calorie consumption will be calculated if the weight of the user is taken into consideration. That is, if the weight of the user is applied to Equation 6, it is possible to calculate the calorie consumption for the steps of the user.

The pedometer can be installed in the portable terminal. That is, if the controller 151 and the acceleration sensor 153 of the pedometer shown in FIG. 1 are added to the portable terminal comprising the memory section, the display section and the input section, the portable terminal has a pedometer function without enlarging the size of the portable terminal. The following description will be made in relation to the portable terminal equipped with the pedometer. If the portable terminal is equipped with the pedometer, the pedometer measures the quantity of exercise and calorie consumption of the user under the control of the controller of the portable terminal. In addition, the portable terminal can transmit the measured quantity of exercise and calorie consumption of the user under the control of the controller of the portable terminal. The controller of the portable terminal receives information related to the quantity of exercise and calorie consumption of the user measured by the pedometer and stores them in the memory section thereof. If the user requests the data related to the quantity of exercise and calorie consumption of the user, the controller of the portable terminal displays the quantity of exercise and calorie consumption of the user in the display section.

Figure 22:
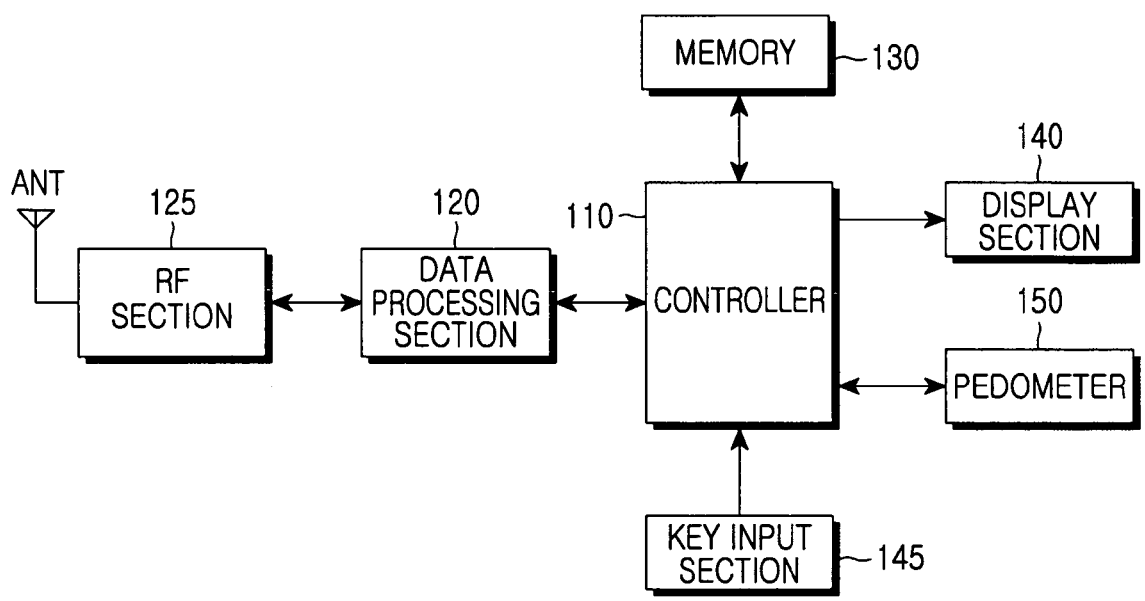
FIG. 22 is a block view illustrating a structure of a portable terminal equipped with a pedometer according to an embodiment of the present invention.
Figure 23:
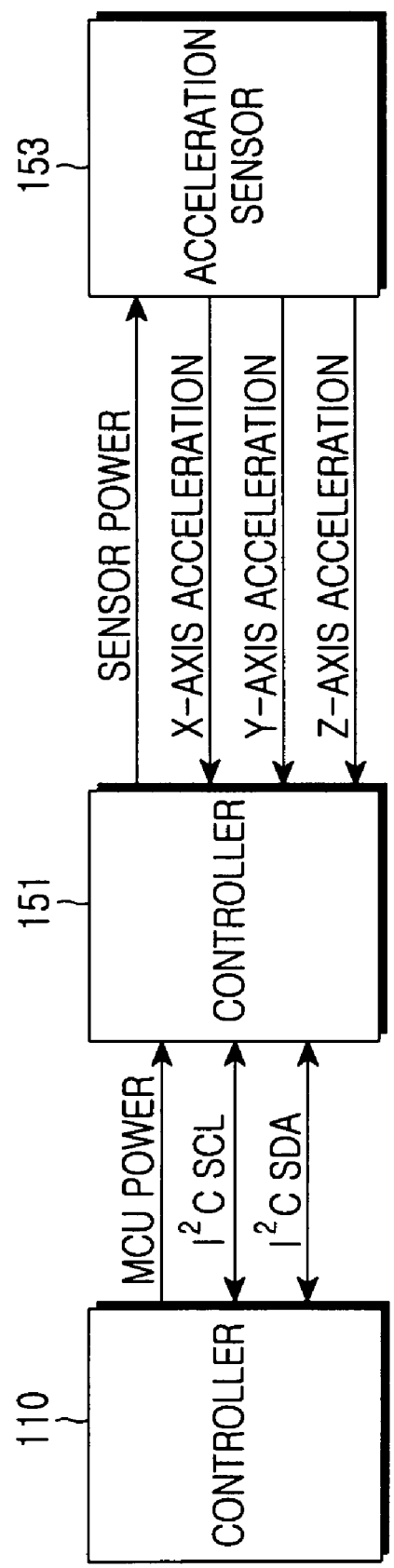
FIG. 23 is a block view illustrating the relationship between a controller of a portable terminal and a pedometer that has the exemplary energy and trigger levels shown in FIG. 12.

FIG. 22 is a block view illustrating a structure of the portable terminal equipped with the pedometer and FIG. 23 is a block view illustrating the relationship between the controller of the portable terminal and the pedometer.

Referring to FIG. 22, an RF section 125 performs an RF communication function for the portable terminal. The RF section 125 comprises an RF transmitter for up-converting and amplifying a frequency of a transmitted signal and an RF receiver for low-noise amplifying and down-converting a frequency of a received signal. A data processing unit 120 comprises a transmitter for encoding and modulating the transmitted signal and a receiver for decoding and demodulating the received signal. That is, the data processing unit 120 preferably comprises a MODEM and a CODEC.

A key input section 145 preferably comprises various functional keys for inputting numbers and text information and for setting various functions.

A memory 130 comprises a program memory and a data memory. The program memory stores programs used for processing functions of the portable terminal and programs used for managing displaying the quantity of exercise according to an embodiment of the present invention. The data memory temporarily stores data generated while executing the programs. In addition, according to an embodiment of the present invention, the data memory comprises memories for accumulating and managing exercise programs, such as time, day and month memories for storing the number of steps and calorie information.

The controller 110 controls an operation of the portable terminal. In addition, the controller 110 displays, accumulates and manages exercise information measured by the pedometer. The controller 110 may comprise the data processing unit 120. That is, the controller 110 can be fabricated in the form of an MSM chip.

A display section 140 displays the state of the portable terminal under the control of the controller 110. The display section 143 may comprise an LCD. That is, the display section 140 may comprise an LCD controller, a memory for storing display data, and an LCD device. If the LCD is embodied as a touch screen type LCD, the LCD may function as an input device.

The controller 110 controls the operation of the pedometer 150. The pedometer 150 measures the quantity of exercise according to the movement of the user of the portable terminal and outputs the measured quantity of exercise to the controller 110.

When transmitting an outgoing call by using the portable terminal having the construction as shown in FIG. 22, a user performs a dialing operation through the key input section 145 and the controller 110 detects the dialing operation. Thus, the controller 110 processes the dial information received through the data processing unit 120 and outputs an RF signal through the RF section 125. Then, if a recipient makes a response to the outgoing call, the controller 110 detects it through the RF section 125 and the data processing unit 120. Thus, the controller 110 forms a communication path consisting of the RF section 125 and the data processing unit 120 so as to allow the user to communicate with the recipient. In addition, when an incoming call is received in the portable terminal, the controller 110 detects the incoming call through the data processing unit 120 and raises an alarm for the incoming call. In this state, if the user pushes a communication key, the controller 110 provides an incoming call service.

In addition, the controller 110 controls the operation of the pedometer 150 according to the request of the user. That is, if the user requests the operation of the pedometer 150, the controller 110 turns on the pedometer 150. Thus, the pedometer 150 measures the quantity of exercise and the calorie consumption according to the movement of the user. In addition, when the controller 110 requests the data related to the quantity of exercise of the user, the pedometer 150 transmits the data to the controller 110. Thus, the controller 110 displays the data in the display section 140 and stores the data in the memory 130.

FIG. 23 shows the relationship between the controller 110 of the portable terminal and the pedometer 150. Reference numeral 151 represents the controller of the pedometer 150. The pedometer 150 preferably comprises the controller 151 and the acceleration sensor 153. The controller 151 of the pedometer 150 is connected to the controller 110 of the portable terminal through a power line, a clock line I²C SCL and a data line I²C SDA. The controller 151 of the pedometer discontinuously drives the acceleration sensor 153 under the control of the controller 110 of the portable terminal. In addition, the controller 151 of the pedometer sets the parameters for measuring the quantity of exercise based on command words from the controller 110 of the portable terminal. The controller 151 measures the quantity of exercise based on the output of the acceleration sensor 153 and accumulates the quantity of exercise. In addition, the controller 151 outputs data related to the quantity of exercise to the controller 110 of the portable terminal as the controller 110 requests the data.

As described above, the structure and the operation of the controller 151 and the acceleration sensor 153 are identical to those of the controller 151 and the acceleration sensor 153 shown in FIG. 1, except that the controller 151 of the pedometer is under the control of the controller 110 of the portable terminal.

Figure 24:
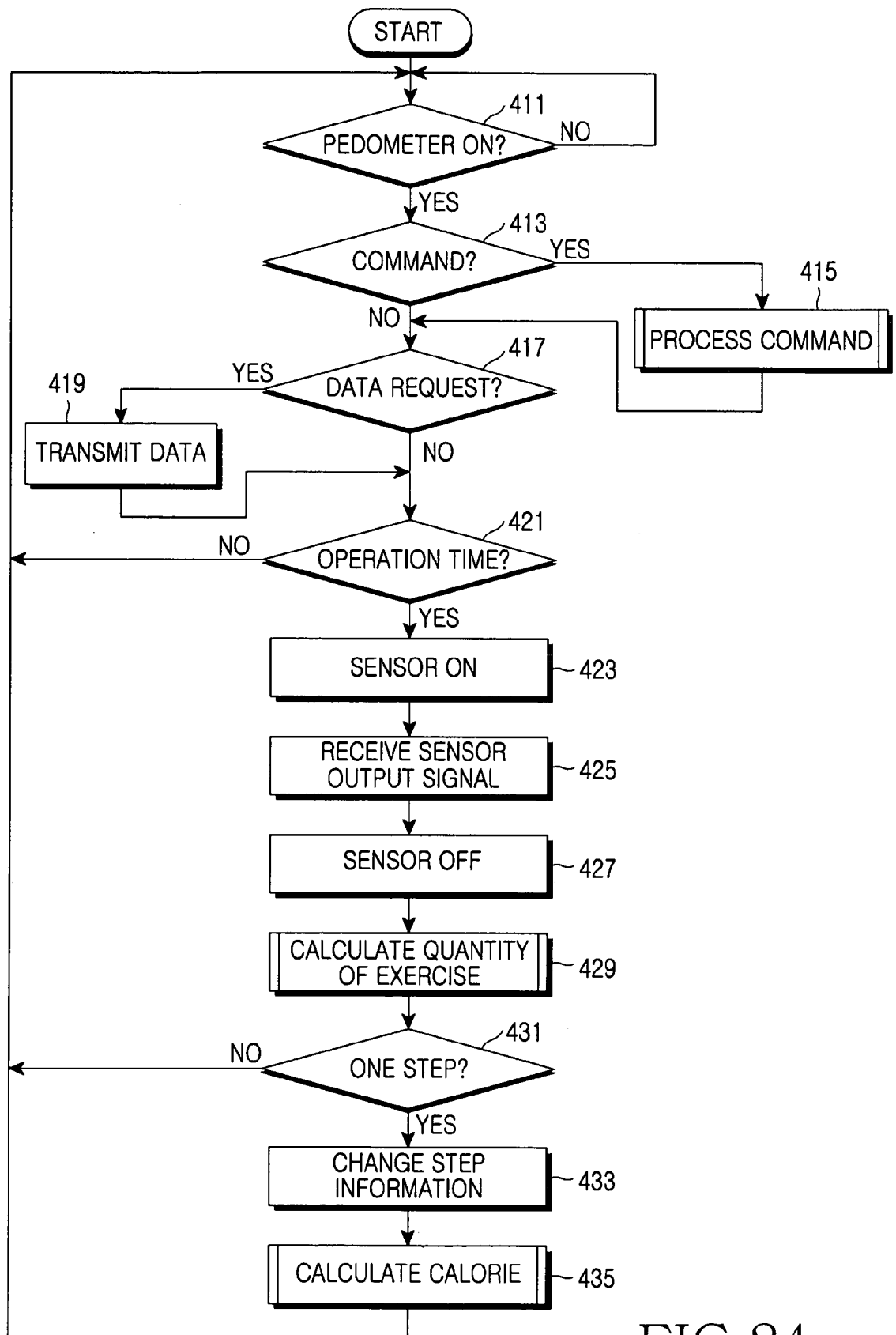
FIG. 24 is a flowchart illustrating the procedure for controlling and sampling an acceleration sensor of a pedometer according to an embodiment of the present invention.

FIG. 24 is a flowchart illustrating the procedure of the controller 151 of the pedometer 150 for calculating quantity of exercise and calorie consumption under the control of the controller 110 of the portable terminal.

Figure 25:
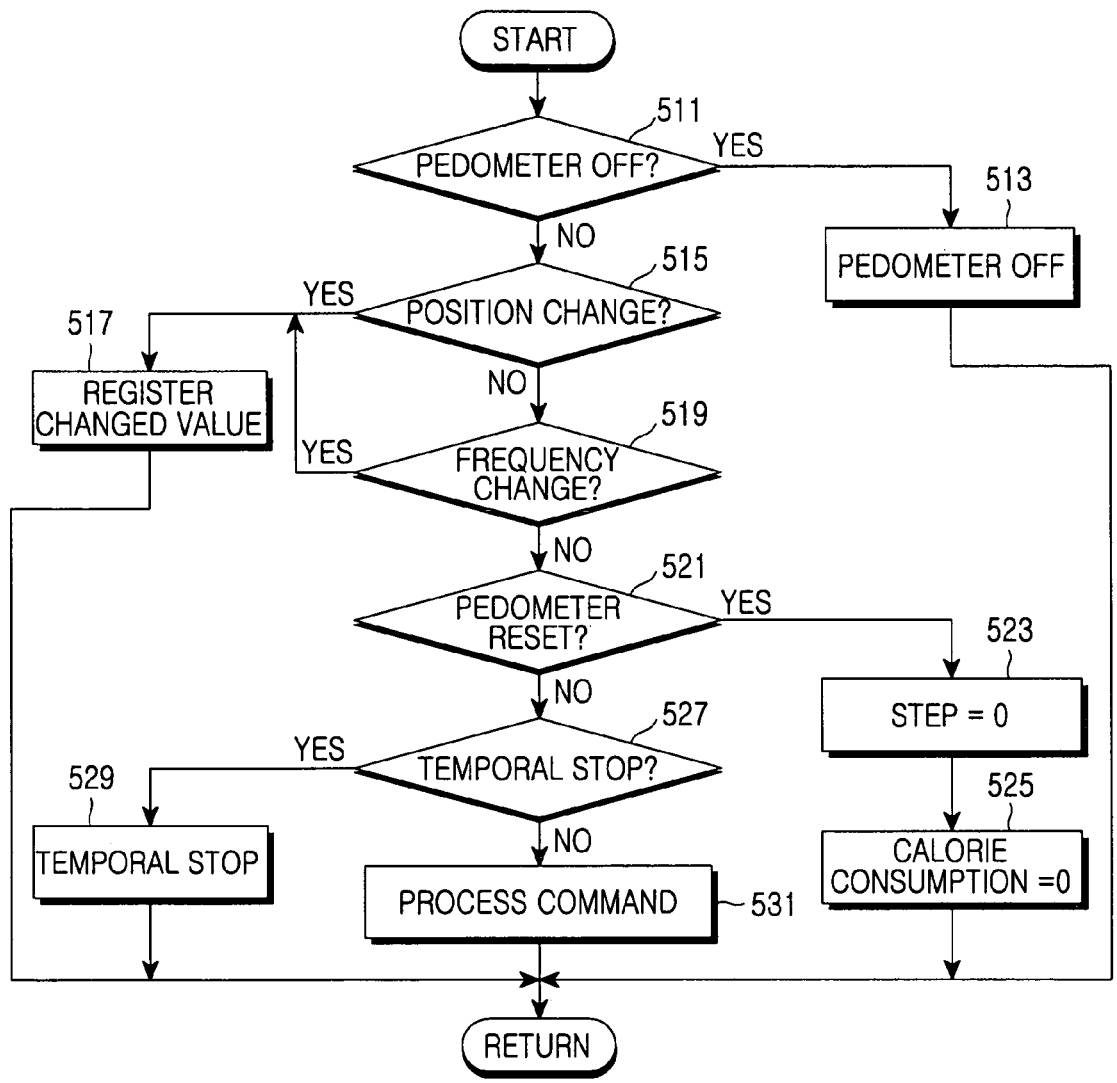
FIG. 25 is a flowchart illustrating the procedure for processing commands according to an embodiment of the present invention.

Referring to FIG. 24, if the controller 110 of the portable terminal generates a power-on command for the pedometer, the controller 151 of the pedometer 150 detects it (step 411). Then, if the controller 151 of the pedometer 150 receives a control command from the controller 110 of the portable terminal (step 413), the controller 151 of the pedometer performs the function corresponding to the control command. FIG. 25 is a flowchart illustrating the procedure of the controller 151 for processing commands of the controller 110.

Referring to FIG. 25, the control commands comprise a command for changing an operation mode of the pedometer, a command for resetting the pedometer and a command for notifying position variation of the pedometer. If a command for stopping the operation of the pedometer is received, the controller 151 detects it (step 511) and shuts off the power being supplied to the pedometer (step 513). In this case, the power being supplied to the acceleration sensor 153 is shut off, so that the procedure of calculating the quantity of exercise is not performed.

If a command for requesting the position change of the pedometer is received, the controller 151 detects it (step 515) and registers a position value of the pedometer 150 according to the command (step 517). The position change command may include the position information of the pedometer 150. That is, since the pedometer 150 can be attached to the front or rear pockets of trousers of the user, the pocket of the jacket, the bag or the hand of the user, the position change command is generated in order to establish the position information of the pedometer 150. If the controller 151 receives the position change command, the controller 151 registers the position information of the pedometer therein.

If a command for changing the frequency is received, the controller 151 detects it (step 519) and registers a frequency change value therein (step 517). The command for changing the operation mode is the command for changing the frequency (that is, the frequency of the controller 151 for sampling the output of the acceleration sensor 153) used for changing the sampling interval as shown in FIGS. 3A and 3B. That is, in the normal measurement mode as shown in FIG. 3A, the controller 151 supplies power to the acceleration sensor 153 in every two active times. In addition, in the detail measurement mode as shown in FIG. 3B, the controller 151 supplies the power to the acceleration sensor 153 in every active time.

If a command for resetting the pedometer is generated, the controller 151 detects it (step 521) and initializes the number of steps and calorie consumption accumulated in the controller 151 to "0" in steps 523 and 525, respectively. That is, the command for resetting the pedometer is generated when it is necessary to reset the information related to the number of steps and calorie consumption stored in the controller 151.

If a command for temporarily stopping the operation of the pedometer is received, the controller 151 detects it (step 527) and stops the operation of the pedometer 150 for a predetermined period of time (step 529). At this time, the controller 151 shuts off the power supplied to the acceleration sensor 153 for the predetermined temporary period of time.

Besides the above commands, a command for registering the weight of the user and a command for changing the factors used for calculating the quantity of exercise and calorie consumption can be utilized. In this case, the controller 151 detects the temporary stop command in step 527 and performs the function corresponding to the commands in step 531.

Figure 26:
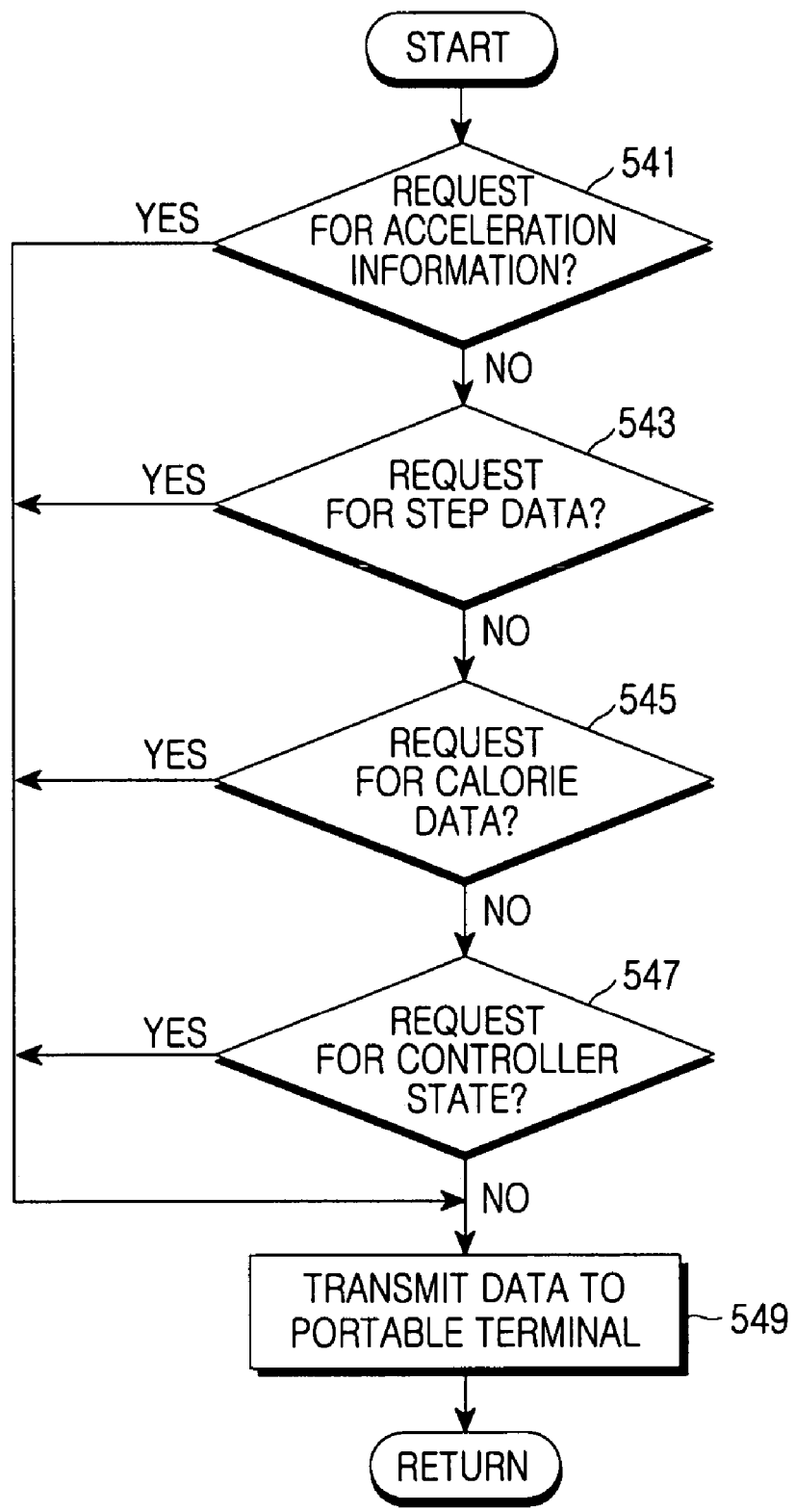
FIG. 26 is a flowchart illustrating the procedure for transmitting data after analyzing the type of data requested for transmission according to an embodiment of the present invention.

In addition, the controller 110 can request information related to the measured number of steps and calorie consumption. If such a request occurs, the controller 151 detects it (step 417 in FIG. 24) and transmits the information related to the measured number of steps and calorie consumption to the controller 110 (step 419). FIG. 26 is a flowchart illustrating the procedure of the controller 151 for transmitting data to the controller 110 after analyzing the data requested by the controller 110.

Referring to FIG. 26, the controller 110 can request data, such as acceleration information, the number of steps, calorie consumption and the state of the controller 151. If the controller 110 requests one type of data, the controller 151 detects it through steps 541 through 547 and transmits the requested data to the controller 110 (step 549). At this time, the controller 151 communicates with the controller 110 through the I²C scheme.

The controller 110 can continuously request the number of steps and calorie consumption data at a predetermined time interval. Since the time memory is provided in the memory 130 of the portable terminal, the controller 110 may access the measurement information of the pedometer 150 at the time interval of one hour and accumulate the data in the corresponding time memory thereof.

The controller 151 may measure the quantity of exercise and calorie consumption of the user while controlling the acceleration sensor 153 when it does not perform the functions according to the command and data request. At this time, the controller 151 measures the quantity of exercise and calorie consumption of the user through the procedure identical to steps 421 and 435 shown in FIG. 9. The controller 151 of the pedometer receives the quantity of exercise detected by the acceleration sensor 153 while controlling the power supplied to the acceleration sensor 153. At this time, the controller 110 can supply a timing signal to the controller 151 at a predetermined interval in order to allow the controller 151 to control the power supplied to the acceleration sensor 153. In addition, it is also possible to allow the controller 151 to control the power supplied to the acceleration sensor 153 as the controller 110 operates the pedometer until the controller 110 supplies the off-signal to the controller 151.

In addition, the pedometer controller 151 samples the output of the acceleration sensor 153 in the manner as shown in FIG. 3D and calculates the quantity of exercise while performing the procedure as shown in FIG. 10. If the type of step of the user is determined, the pedometer controller 151 may calculate the calorie consumption according to the predetermined procedure. The method of finally calculating the calorie consumption by the portable terminal will be described later in further detail. In addition, such a method can be performed by means of the pedometer controller 151.

The controller 110 of the portable terminal controls the operation of the pedometer 150 and requests the data related to the quantity of exercise and calorie consumption measured by the pedometer 150. In addition, the controller 110 accumulates and displays the data.

Figure 27:
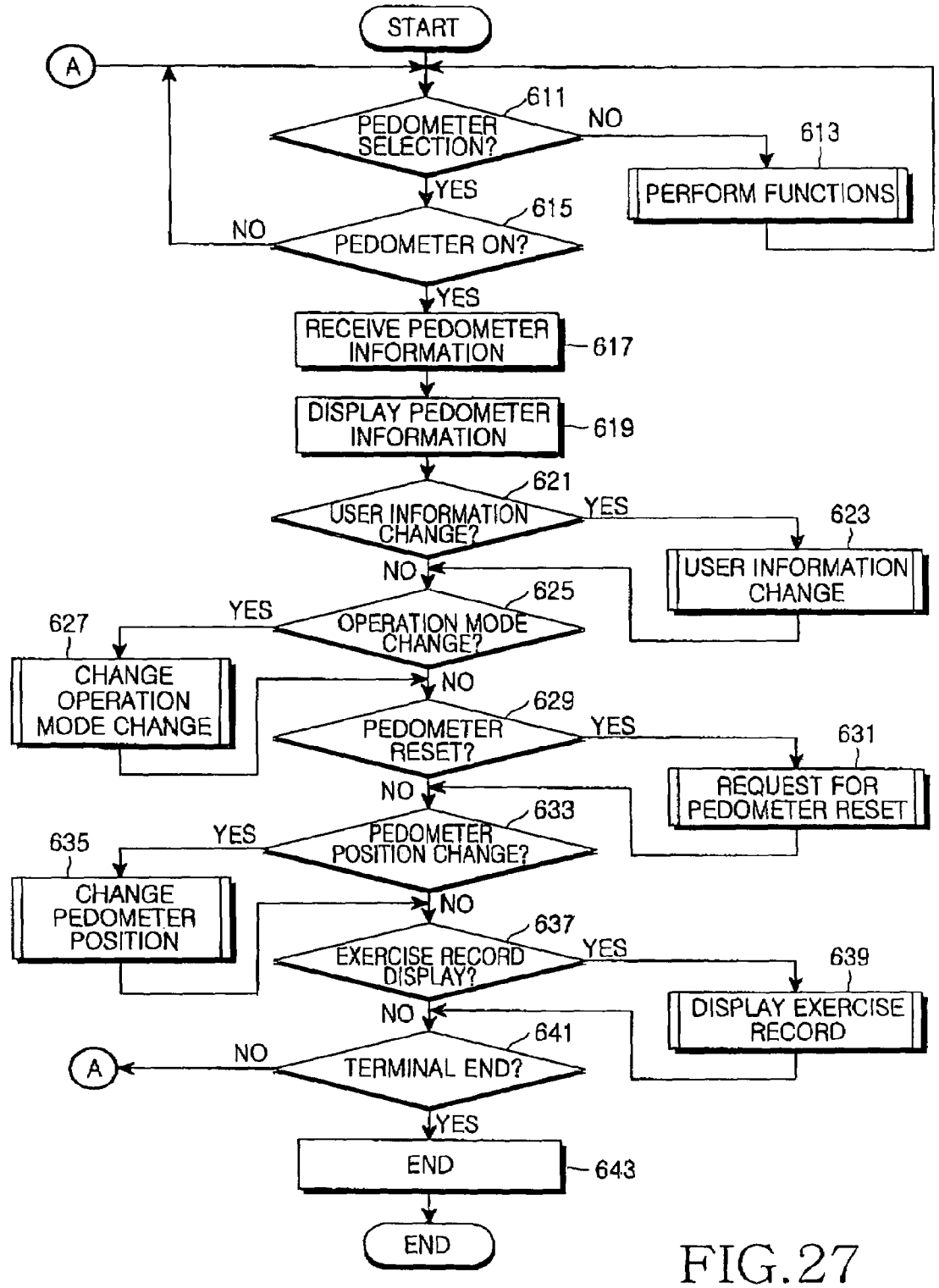
FIG. 27 is a flowchart illustrating the procedure for controlling a pedometer in a portable terminal according to an embodiment of the present invention.

Referring to FIG. 27, the pedometer 150 receives data related to the weight and height of the user from the portable terminal and displays the quantity of exercise and calorie consumption of the user. In addition, the pedometer 150 can store and manage the above data for a predetermined period of time. The pedometer can be operated when the portable terminal is powered on for the first time. It is also possible to control the operation of the pedometer by using a main menu of the portable terminal. The user can stop the operation of the pedometer 150.

The pedometer 150 can be operated by selecting a menu from the main menu of the portable terminal. If the user selects the operation menu of the pedometer 150 from the main menu of the portable terminal, the controller 110 detects it (step 611) and checks whether the pedometer is in an on-state (step 615). If the pedometer is on-state, the controller 110 receives information from the pedometer 150 (step 617) and displays information related to the quantity of exercise of the user in the display section 140 (step 619). At this time, the information displayed in the display section 140 may comprise the number of steps and calorie consumption of the user.

In this state, if the user selects a menu, the user of the portable terminal can input command words (textually or spoken) for controlling the operation of the pedometer. 150 or can check the quantity of exercise measured by the pedometer 150. The menu preferably includes the user information change, operation mode change, pedometer reset, change for the attachment position of the pedometer, and display for exercise record.

Figure 28A:
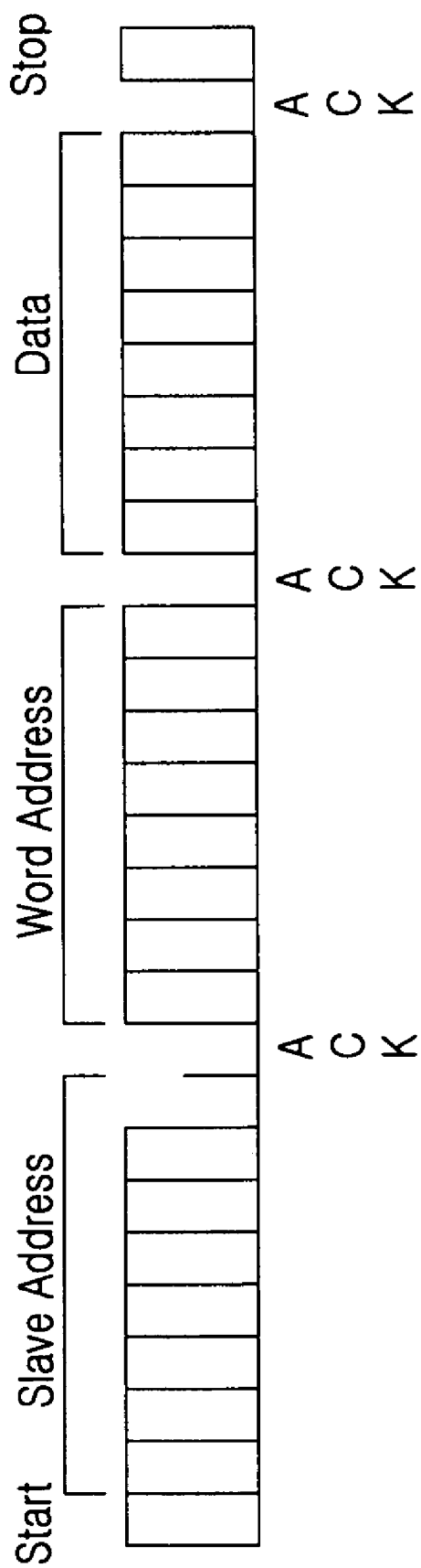
FIGS. 28A and 28B are views illustrating communication protocols between a controller of a portable terminal and a controller of a pedometer according to an embodiment of the present invention.
Figure 28B:
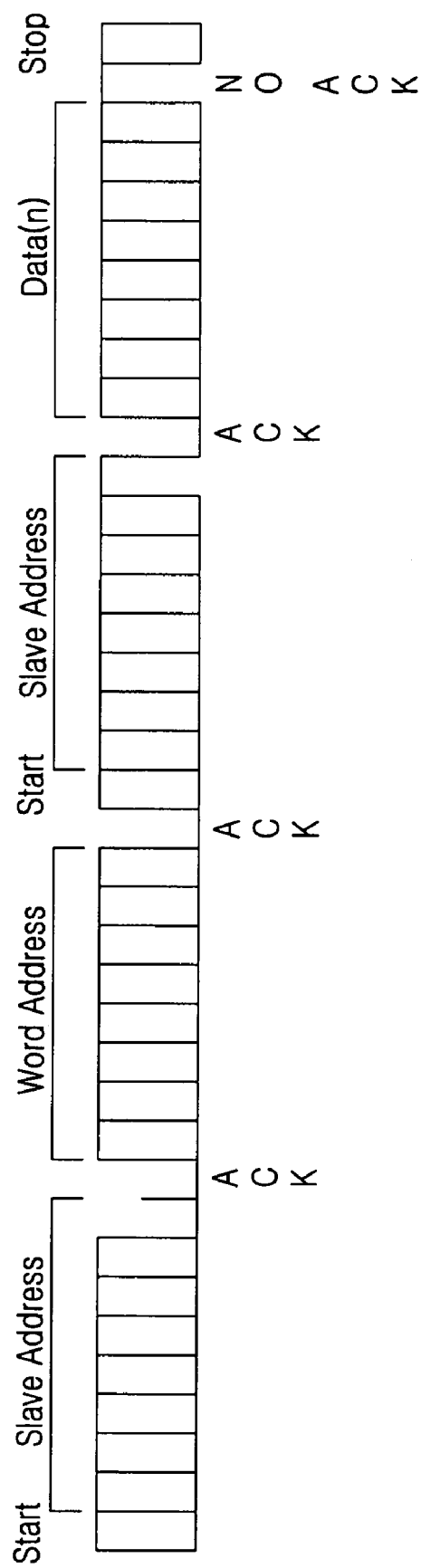

The controller 151 of the pedometer 150 makes data communication with the controller 110 of the portable terminal according to the I²C communication protocol. FIG. 28A shows the I²C communication protocol used when the controller 110 writes the command on the controller 151 of the pedometer 150. In addition, FIG. 28B shows the I²C communication protocol used when the controller 110 reads the information of the pedometer 150. Referring to FIG. 28A, when the controller 110 transmits the command to the controller 151 of the pedometer 150, the controller 110 writes the address of the pedometer 150 in a slave address and inputs a register address into a word address. Register address information may preferably comprise the pedometer reset, operation mode change (frequency change), pedometer off, temporal stop of the pedometer and change of the attachment position of the pedometer. In addition, data used for performing the functions of the command can be recorded in a data field. Referring to FIG. 28B, when the controller 110 wants to read the data from the pedometer 150, the controller 110 transmits the data after writing the address of the pedometer 150 in the slave address and the kind of desired data in the word address. The kind of desired data preferably includes acceleration information (X, Y and Z-axis data), the number of steps, calorie consumption and the state of the pedometer 150. In response to the controller 110, the pedometer controller 151 of the pedometer 150 transmits the data to the controller 110 by writing the address of the pedometer in the slave address and inputs data requested by the controller 110 in the data field. Accordingly, the command as shown in FIG. 28A is transmitted to the pedometer controller 151 from the controller 110 of the portable terminal so that the pedometer controller 151 controls the operation of the pedometer 150 according to the received command or registers the received command. In addition, as show in FIG. 28B, if the controller 110 of the portable terminal requests the data, the controller 151 of the pedometer 150 transmits the data requested by the controller 110 to the controller 110 of the portable terminal. At this time, the controller 151 of the pedometer 150 communicates with the controller 110 of the portable terminal through the I²C protocol scheme.

Figure 29:
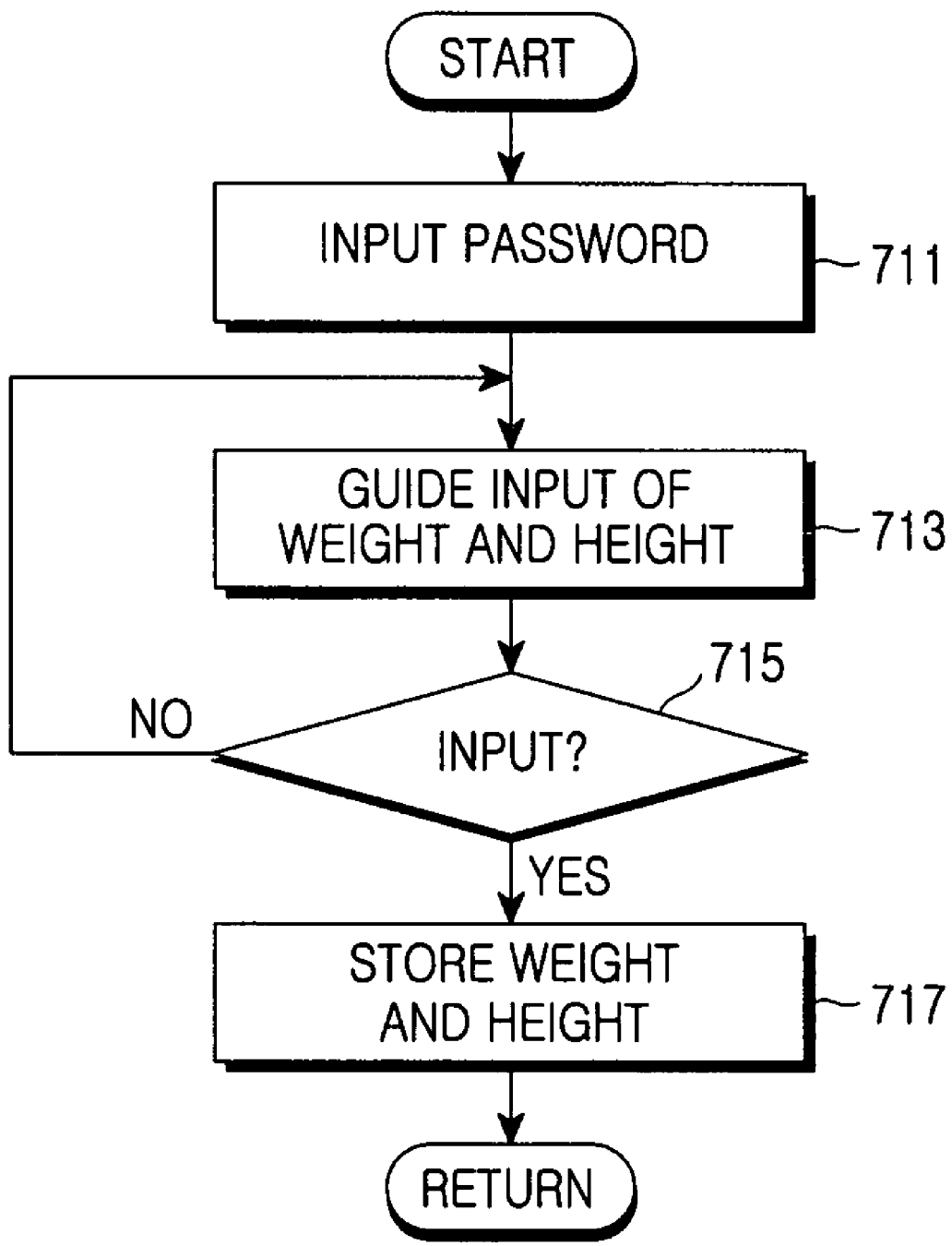
FIG. 29 is a flowchart illustrating the procedure for changing user information according to an embodiment of the present invention.

If the user information change is selected, the controller 110 detects it (step 621) and changes the user information (step 623). FIG. 29 is a flowchart illustrating the procedure of the controller 110 for correcting the user information as shown in step 623 in FIG. 27. Referring to FIG. 29, the user information may includes the weight and the height of the user having the pedometer 150. In addition, the user information can be utilized as data for calculating the calorie consumption according to the quantity of exercise. A password is required to register the user information. At this time, the password of the portable terminal can be used to register the user information. However, it is also possible to use a password different from the password of the portable terminal. If the password is not established, step 711 can be omitted. As the password is input, the controller 110 checks it in step 711 and guides the input of the weight and the height of the user (step 713). When the user inputs the weight and the height of the user, the controller 110 checks it in step 715 and stores the weight and the height of the user in the memory 130 (step 717). Then, the controller 110 returns to the procedure shown in FIG. 27.

Figure 30:
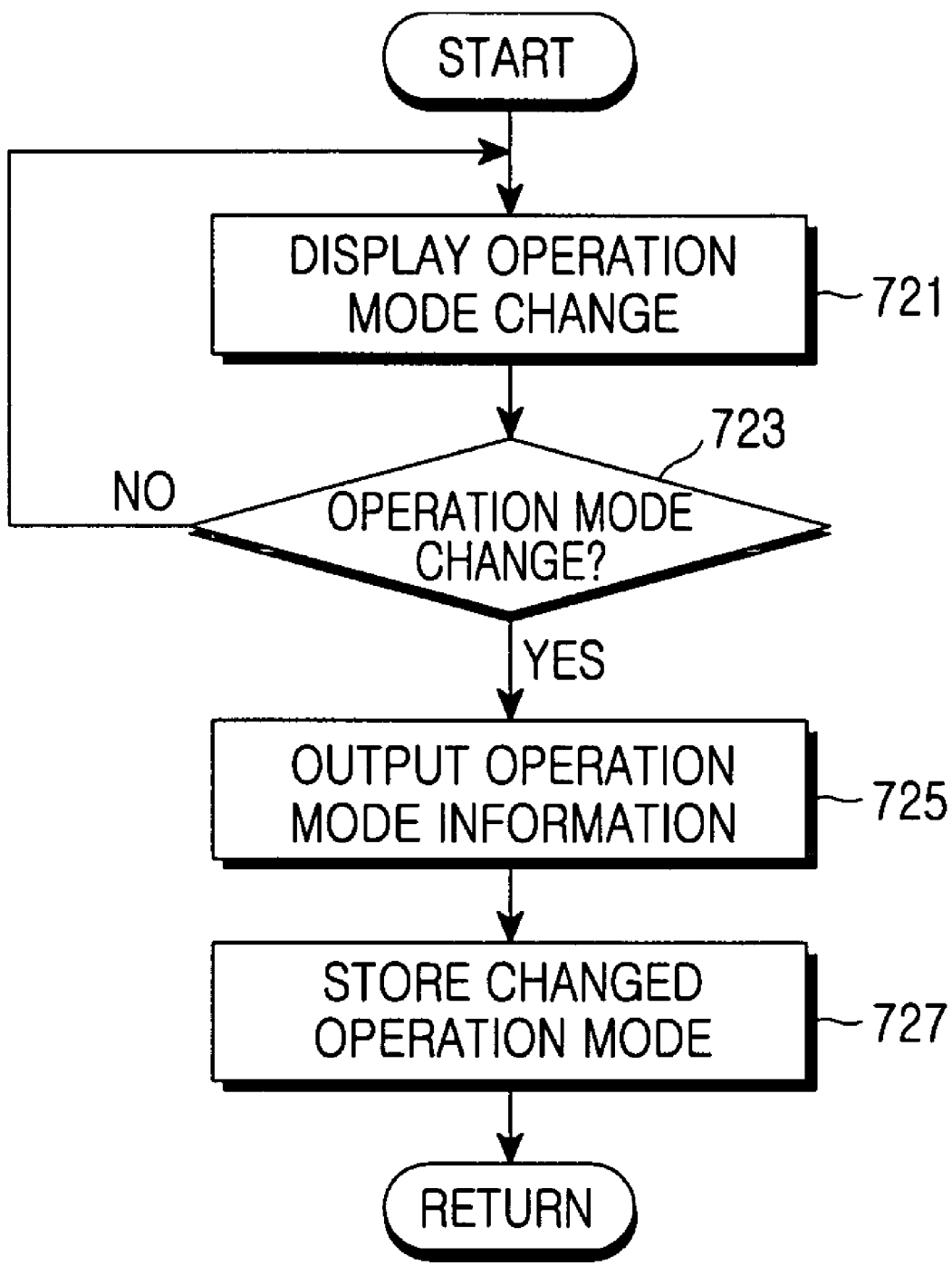
FIG. 30 is a flowchart illustrating the procedure for changing an operation mode according to an embodiment of the present invention.

If the operation mode change is selected, the controller 110 detects it (step 625) and changes the operation mode of the pedometer 150 (step 627). At this time, the controller 151 of the pedometer 150 establishes the field for sampling the output of the acceleration sensor 153. FIG. 30 is a flowchart illustrating the procedure of the controller 110 for changing the operation mode of the pedometer.

Referring to FIG. 30, if the operation mode change is selected, the controller 110 displays it in the display section 140 (step 721) and waits for the input of parameters for changing the operation mode. If the parameters are input in order to change the operation mode, the controller 110 detects it (step 723) and generates the command for the operation mode change (step 725). The controller 110 transmits the command to the pedometer controller 151 and registers the changed operation mode therein. In this case, the controller 110 transmits data by writing the command for the operation mode change in the word address field and inputs data of the normal measurement mode or the detail measurement mode in the data field shown in FIG. 28A. In the normal measurement mode, power supply and sampling operation are achieved as shown in FIG. 3A. In addition, in the detail measurement mode, power supply and sampling operation are achieved as shown in FIG. 3B. Thus, the controller 151 of the pedometer 150 controls the power supply and sampling operation as shown in FIG. 24.

If the pedometer reset is selected, the controller 110 detects it (step 629) and transmits the reset command for the pedometer (step 631). In response to the reset command, the controller 151 of the pedometer 150 resets the data related to the number of steps and calorie consumption, which have been measured and accumulated.

Figure 31:
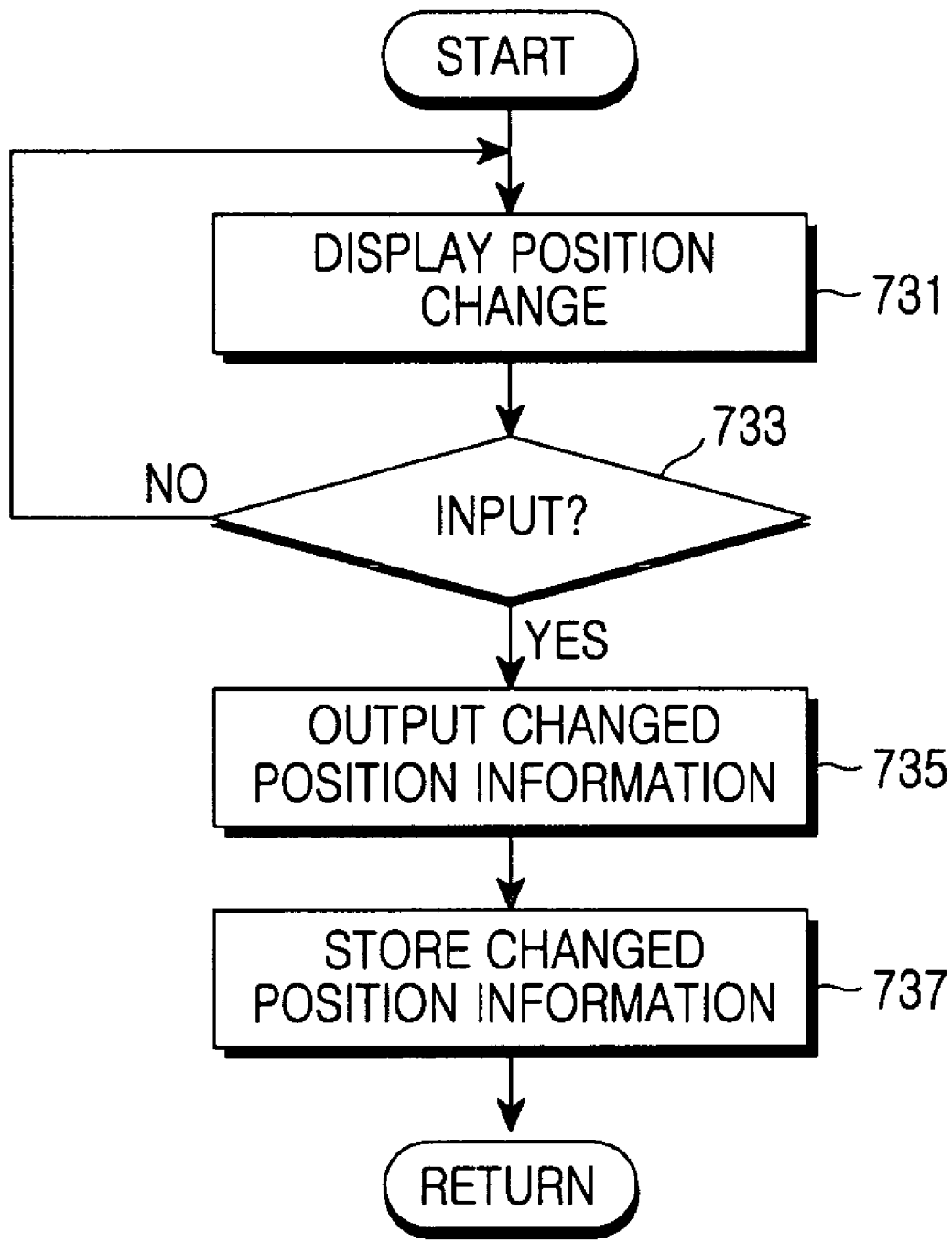
FIG. 31 is a flowchart illustrating the procedure for changing an installation position of a pedometer according to an embodiment of the present invention.

If the change of the attachment position for the pedometer is selected, the controller 110 detects it (step 633) and changes the position information of the pedometer (step 635). The position information of the pedometer preferably includes the attachment position of the portable terminal (pedometer) with respect to the user. Since the quantity of exercise of the user may vary depending on the attachment position of the portable terminal, the quantity of exercise must be calculated by taking the attachment position of the portable terminal into consideration. FIG. 31 is a flowchart illustrating the procedure of the controller 110 for changing the attachment position of the pedometer.

Referring to FIG. 31, as the change of the attachment position for the pedometer is selected, the controller 110 displays the attachment position of the pedometer in the display section 140 (step 731) and waits for the input of parameters for changing the attachment position of the pedometer. At this time, the attachment position displayed in the display section 140 preferably includes front or rear pockets of trousers, a pocket of a jacket, a bag, and a neck or a hand of the user. In this state, if a predetermined attachment position of the pedometer is selected, the controller 110 detects it (step 733) and generates the command for the position change of the pedometer 150 (step 735). In addition, the controller 110 transmits the command to the controller 151 and registers the changed position information for the pedometer therein (step 737). In this case, the controller 110 transmits the data by writing the position change command in the word address field and inputting the selected position information in the data field shown in FIG. 28A. Thus, the controller 151 of the pedometer 150 calculates the calories consumption by taking the position information of the pedometer 150 into consideration.

Referring back to FIG. 27, if the display for the exercise record is selected, the controller 110 detects it (step 637) and displays the quantity of exercise selected by the user in step 639.

Figure 32:
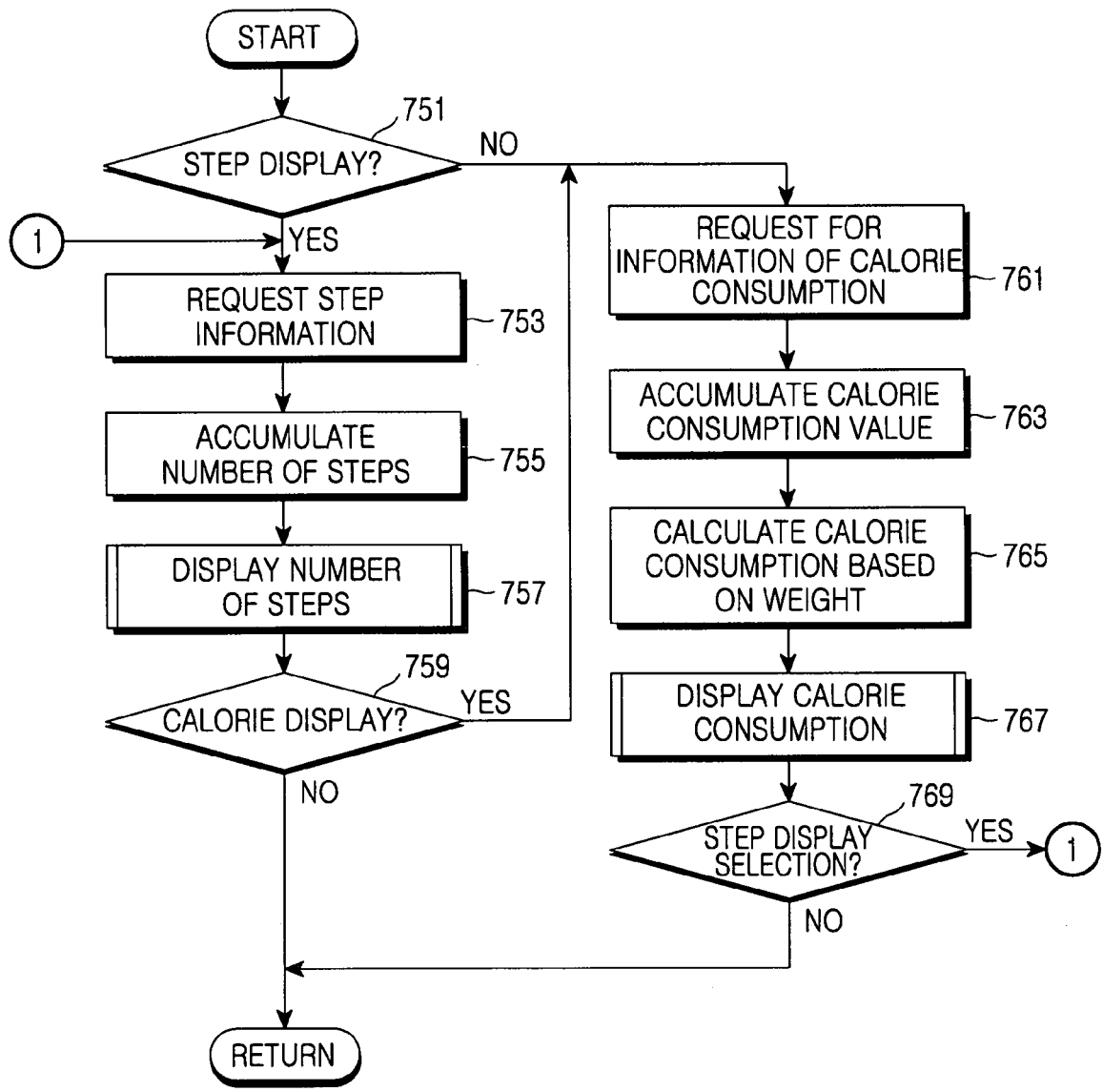
FIG. 32 is a flowchart illustrating the procedure for processing and displaying the quantity of exercise according to an embodiment of the present invention.
Figure 47A:
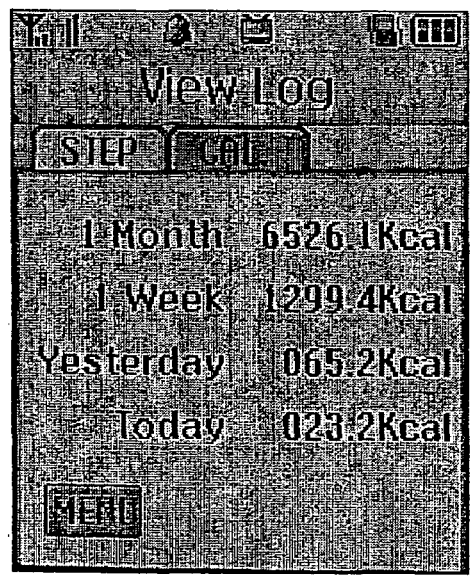
FIGS. 47A to 47J are views illustrating exemplary screen images for displaying information related to calorie consumption measured in a pedometer according to an embodiment of the present invention.
Figure 47B:
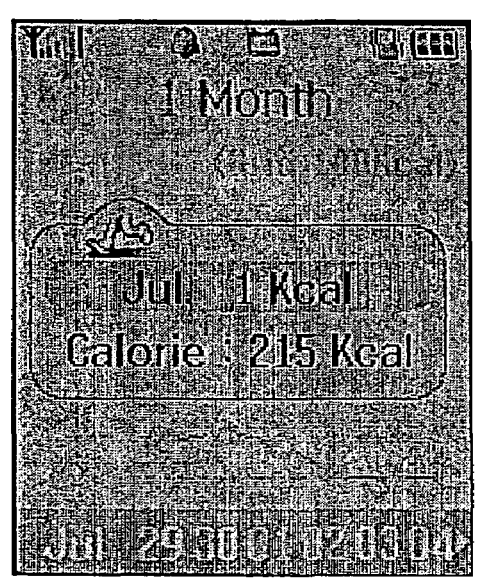
Figure 47C:
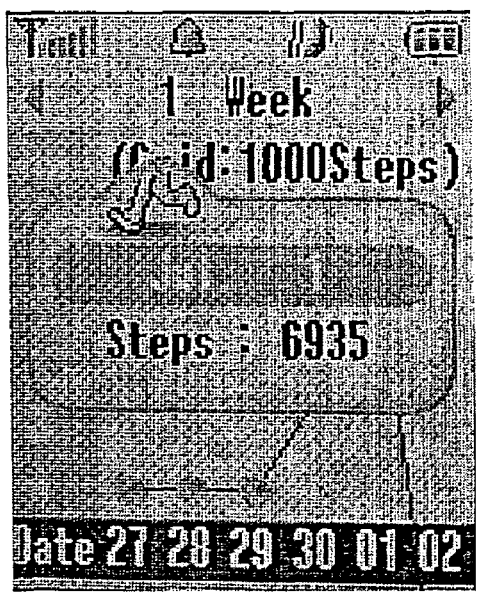
Figure 47D:
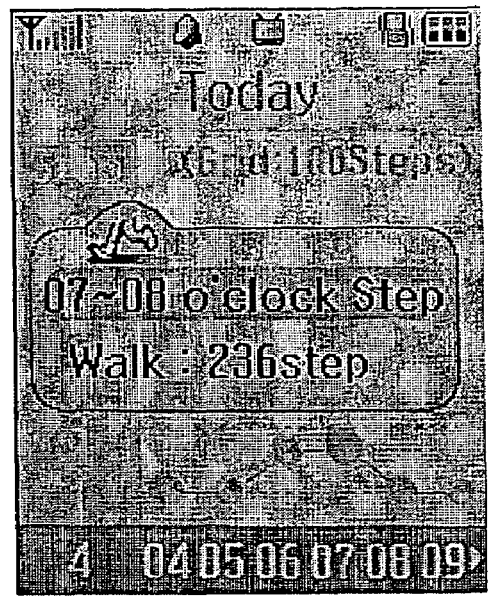
Figure 47E:
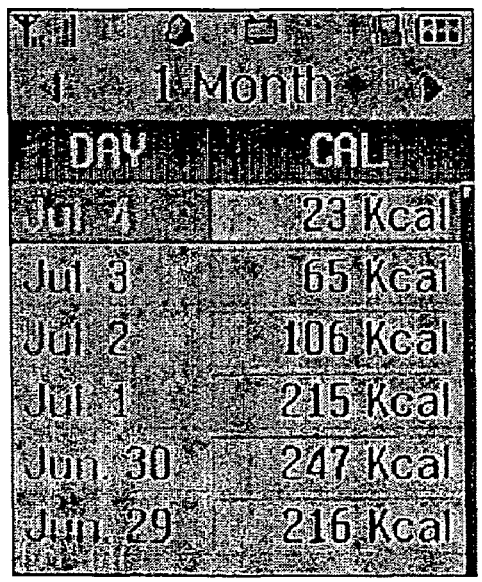
Figure 47F:
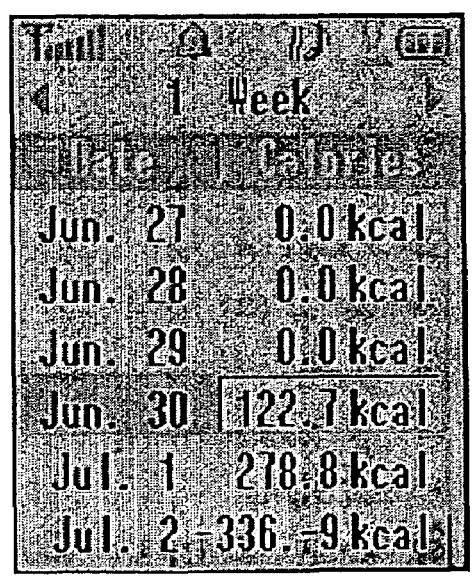
Figure 47G:
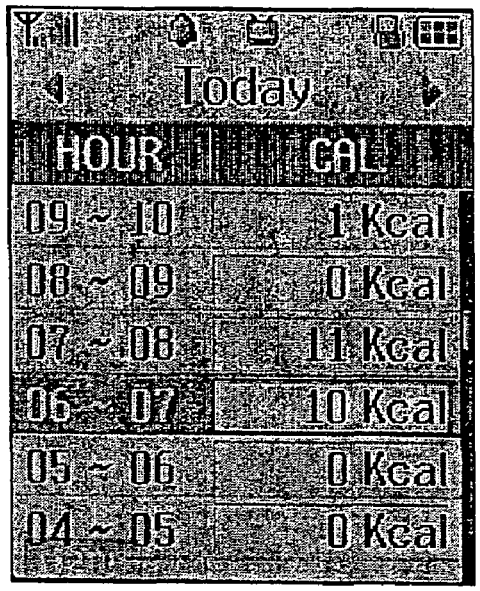
Figure 47H:
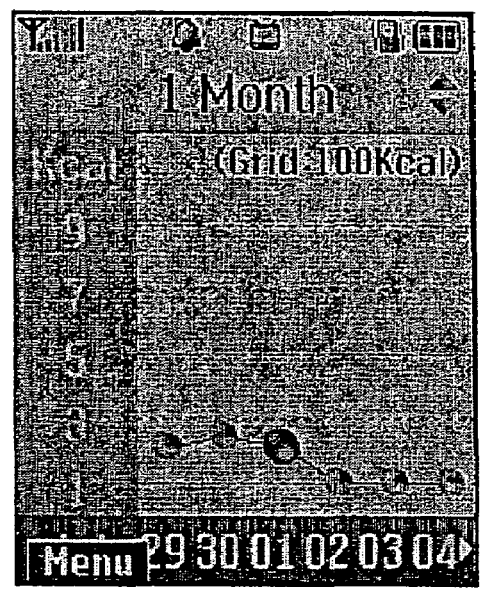
Figure 47I:
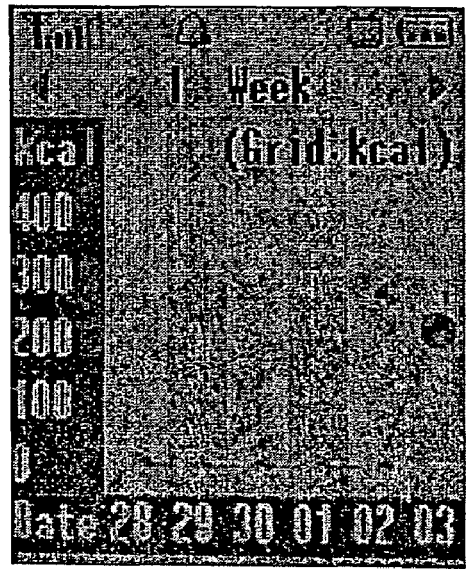
Figure 47J:
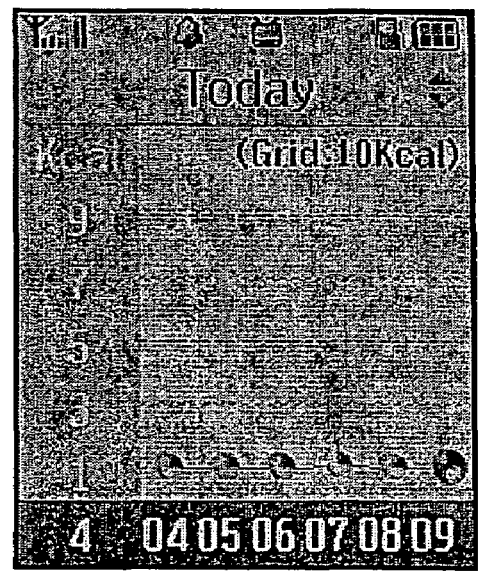

FIG. 32 is a flowchart illustrating the procedure of the controller 110 for displaying the quantity of exercise selected by the user. Referring to FIG. 32, if the user selects the display for the exercise record, the user can check the number of steps and calorie consumption of the user. In addition, it is also possible for the user to select the period of time for the exercise record and to check the exercise record expressed in figures or graphs. If the user selects the display for the number of steps, the controller 110 detects it (step 751) and requests the transmission of data related to the number of steps. Upon receiving the data from the controller 151 of the pedometer 150, the controller 110 accumulates and stores the data in the present time memory of the memory 130 (step 755). Then, the controller 110 loads the step information stored in the memory 130 and displays the step information as shown in FIG. 47A (step 757). The quantity of exercise during a predetermined period of time can be represented in the form of figures or graphs according to the selection of the user.

Hereinafter, the procedure for displaying the number of steps will be described in detail. As shown in FIGS. 47E to 47G, 47H to 47J or 47B to 47D, the number of steps can be represented in the form of graphs or numerical data. In addition, the period of time for the step data, such as today, yesterday, a week, or a month, can be selected by the user. That is, while the number of steps is being displayed, if the user selects the menu key displayed at a left lower portion of the display section, a graph key and a figure key are displayed. If the user enters the graph key, the user can select a period of time within the latest month (today, yesterday, a week, or a month). In this state, the user can select a predetermined period of time by using a directional key. If the user selects the predetermined period of time, the controller 110 detects it and displays the step information corresponding to the selected period of time in the display section 140. In addition, if the user selects the figure key, the user can select the predetermined period of time within the latest month (today, yesterday, a week, or a month). In this state, if the user selects the predetermined period of time by using the directional key, the controller 110 detects it and displays the step information corresponding to the selected period of time in the display section 140. At this time, the step information of the latest month can be displayed in the form of weekly step information or a daily step information. The weekly step information may be displayed with date and the daily step information may be displayed with time.

In addition, if the user selects the calorie consumption menu while the number of steps is being displayed in the display section, the controller 110 detects it (step 759) and converts the step display mode into a calorie consumption display mode (step 761). Accordingly, if the step or calorie consumption display mode is selected in step 751 or 759, respectively, the controller 110 requests the transmission of calorie consumption data is accumulated in the controller 151 of the pedometer 150 in step 761. Upon receiving the calorie consumption data, the controller 110 stores the data in the present time memory of he memory 140 (step 763). After that, the controller 110 loads information related to calorie consumption stored in the memory 130 thereof and calculates again the calorie consumption by taking the weight of the user into consideration (step 765). The weight of the user is preliminarily registered through the procedure as shown in FIG. 29, and the calorie consumption can be calculated according to Equation 7. As described above, according to an embodiment of the present invention, the calorie consumption of a person having a standard weight (60 kg) is first measured by means of the pedometer 150 and the controller 110 of the portable terminal measures the calorie consumption of the user by applying the weight of the user to the above standard calorie consumption. Thus, it is possible to precisely measure the calorie consumption according to the weight of the user. According to an embodiment of the present invention, the pedometer 150 primarily calculates the calorie consumption and the portable terminal secondarily calculates the calorie consumption. However, if the controller 110 of the portable terminal transmits the information about the weight of the user to the pedometer 150, the pedometer 150 can calculate the calorie consumption by taking the weight of the user into consideration.

After calculating the calorie consumption, the controller 110 displays information related to calorie consumption as shown in FIG. 48A (step 767). At this time, the calorie consumption during a predetermined period of time can be displayed in the form of figures or graphs according to the selection of the user. The display procedure of the calorie consumption may be identical to the display procedure of the number of steps. That is, the calorie consumption can be displayed in the form of numerical data or graphs as shown in FIGS. 48E to 48G, 48H and 48J or 48B to 48D. If the user selects the display of the step information while the calorie consumption is being displayed in the display section, the controller 110 detects it (step 769) and converts the calorie consumption display mode into the step display mode (step 753).

If the portable terminal is equipped with the pedometer, when the user walks with the portable terminal attached to the waist of the user, variation of acceleration derived from the walking is significantly less than the acceleration of gravity. Thus, it is necessary to detect minute variations of the acceleration by using the acceleration sensor 153 when determining the step of the user. For this reason, the solution of the pedometer having the acceleration sensor 153 becomes sensitive. In this case, although the pedometer can precisely detect the number of steps when the user walks or runs due to the sensitive performance factor of the acceleration sensor 153, the pedometer may regard external impact as the step of the user, so the number of steps may erroneously increase. For instance, if the pedometer or the portable terminal equipped with the pedometer is placed on a table, the pedometer may count the step even when a person knocks the table or an article having a heavy weight is loaded on the table.

For this reason, the pedometer or the portable terminal equipped with the pedometer may be unreliable thereof and may not achieve the import of the pedometer solution "health-care". Accordingly, it is preferred for the pedometer to have an algorithm for protecting the pedometer from external impacts in order to prevent the pedometer from malfunctioning due to the external impacts.

In general, external impact and vibration are intermittently and irregularly applied to the pedometer. In contrast, a signal is stably input into the pedometer when the user walks. Thus, it is preferred to allow the pedometer or the portable terminal equipped with the pedometer to be driven only through a user interface (UI) of the pedometer or the portable terminal equipped with the pedometer.

The malfunction of the pedometer may occur when the user walks with the pedometer after a predetermined standstill, when the pedometer is attached to the waist of the user or accommodated in the pocket, when an external speaker of the portable terminal equipped with the pedometer reproduces sound, or when the portable terminal equipped with the pedometer performs its own functions, such as a key input. The method for solving the potential malfunctions of the pedometer may also be applicable for the portable terminal equipped with the pedometer. Thus, the term "pedometer" used in the following description refers to not only the pedometer, but also the portable terminal equipped with the pedometer.

Figure 33A:
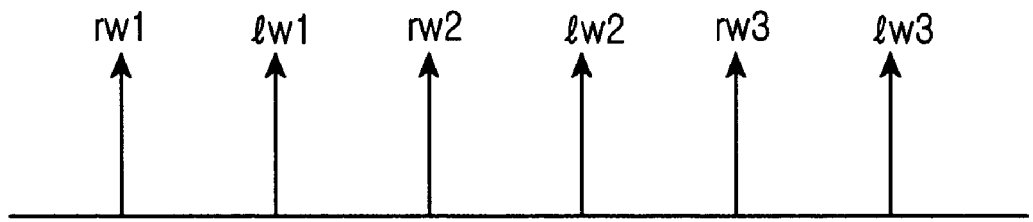
FIGS. 33A to 33C are views illustrating a exemplary data used in method of distinguishing the user's step from noise caused by external impacts and vibration according to an embodiment of the present invention.
Figure 33B:
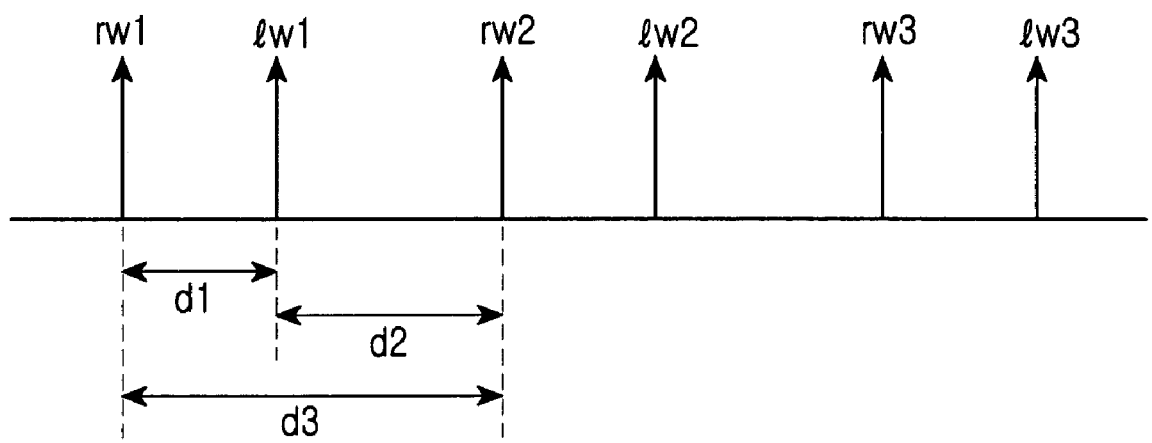

First, when a person knocks the table or an article having a heavy weight is loaded on the table under the state that the pedometer is placed on the table, the acceleration sensor 153 of the pedometer may detect the above external impact as the step of the user. In order to solve this problem, the pedometer is designed in such a manner that the pedometer may count the step of user only when a predetermined number of impacts is regularly transferred thereto at a predetermined interval. In general, as shown in FIG. 33A, the person walks with a constant stride so that the acceleration sensor 153 can detect the dynamic energy with a predetermined time interval. Reference characters rw and lw shown in FIGS. 33A and 33B represent dynamic energy generated by right and left feet, respectively. However, as shown in FIG. 33B, the stride of the right foot may be different from that of the left foot. Thus, a predetermined time lag may happen when the acceleration sensor 153 detects the dynamic energy of the left and right feet. However, as shown in FIG. 33B, although the stride (d1) of the right foot may be different from the stride (d2) of the left foot, the total stride (d3) of the left and right feet are regularly repeated. Thus, the pedometer can distinguish the external impact from the step of the user by using the stride characteristic of the person.

Figure 33C:
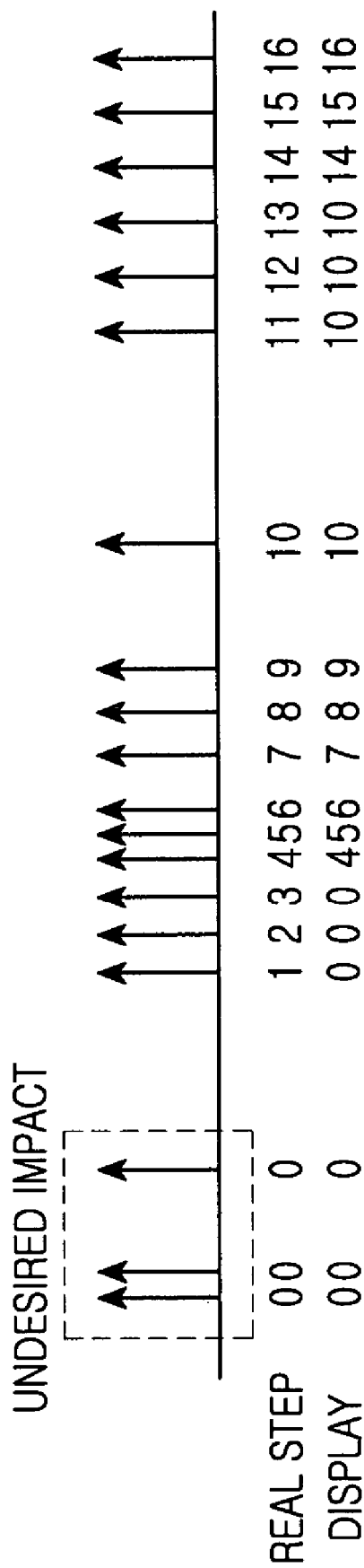

FIG. 33C are views illustrating a method of distinguishing the user step from an external impact according to an embodiment of the present invention. According to an embodiment of the present invention, the pedometer may count the step of an user only when a predetermined number of impacts is regularly transferred thereto at a predetermined interval. The predetermined number of impacts is preferably assumed as being "4". Of course, any number of predetermined impacts can be used. Thus, the controller 151 of the pedometer may operate the pedometer after the person walks four steps. After that, the pedometer counts the impact as an impact corresponding to the step of the user. The above method does not exert an undue influence upon the preciseness of the pedometer, which is determined according to the factor and the threshold value shown in FIG. 10.

If the data set shown in FIG. 33C is an example of the data received by a pedometer, several side effects may occur. First, if the user repeatedly stops for a long period of time after walking three steps, the pedometer may not count the step of the user. However, such a phenomenon may rarely happen, so it can be disregarded. If the user sitting on a chair moves the chair or crosses his or her legs, the external impact may be applied to the pedometer. In this case, the pedometer may not regard the external impact as the step of the user on the basis of the above algorithm. Second, if the user grips or shakes the portable terminal to check the number of steps, as shown in FIG. 33C, the number of steps may not increase at the first three stages, and then the number of steps increases by four steps at a fourth stage. After that, the pedometer counts the number of steps per every step.

Hereinafter, a method for preventing the pedometer from malfunctioning caused by changing the position thereof will now be described in more detail.

Figure 34A:
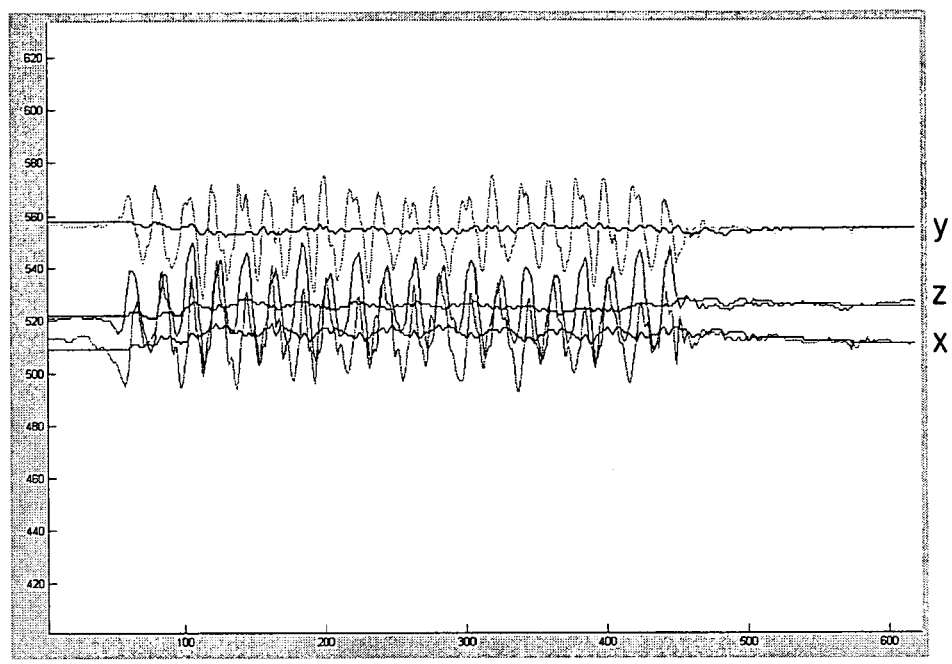
FIGS. 34A and 34B are views illustrating exemplary data used in a method for distinguishing the user's step from noise caused by variation of angular positions of a pedometer according to an embodiment of the present invention.
Figure 34B:
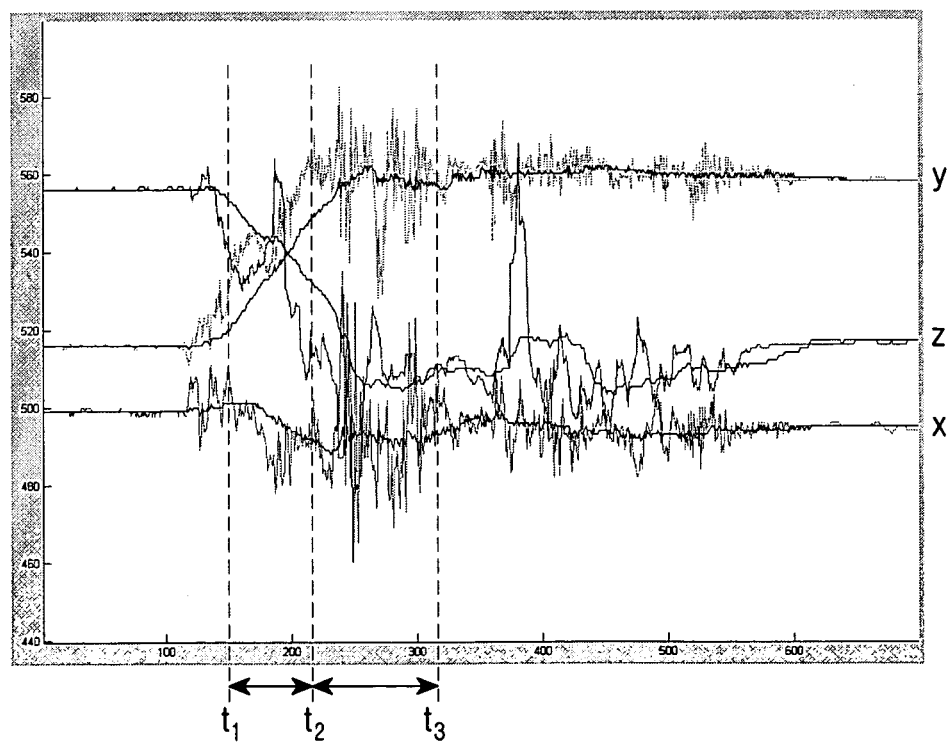

FIG. 34A is a view illustrating the signal characteristics in X, Y and Z-axis of the acceleration sensor 153 occurring when the person walks with the pedometer, and FIG. 34B is a view illustrating the signal characteristics in X, Y and Z-axis of the acceleration sensor 153 occurring when the angular position of the pedometer is suddenly changed.

Referring to FIGS. 34A and 34B, when the user walks with the pedometer, the acceleration sensor 153 generates a regular signal characteristic as shown in FIG. 34A. However, if the pedometer is attached to the waist of the user or the angular position of the pedometer is suddenly changed, the acceleration sensor 153 generates an irregular signal characteristic as shown in FIG. 34B in which detection signals of two axes are crossed with each other. If the angular position of the pedometer with respect to the ground is changed due to the attachment position of the pedometer (the waist or the pocket of the user), the acceleration may vary greatly. In this case, the energy component obtained through the frequency analysis is similar to that of the step of the user. Accordingly, it is necessary to prevent the angular position of the pedometer from being suddenly changed regardless of the step of the user.

In order to solve the above problem, embodiments of the present invention employ DC data by obtaining the DC data by taking an average value of raw data of the acceleration sensor 153. As shown in FIG. 24B, if a value of the DC data is changed due to the change of the angular position of the pedometer (y-axis and z-axis in FIG. 34B), the pedometer disregards the signal even if the signal represents a peak value corresponding to the step. In this manner, the problem occurring when the pedometer is attached to the waist of the user or when the pedometer is accommodated in the pocket can be solved.

Hereinafter, a method for preventing the pedometer from malfunctioning due to noise having high sound pressure will be described. FIGS. 35A to 35F are views illustrating signal and data distributions from noise caused by external sound according to an embodiment of the present invention.

Figure 35A:
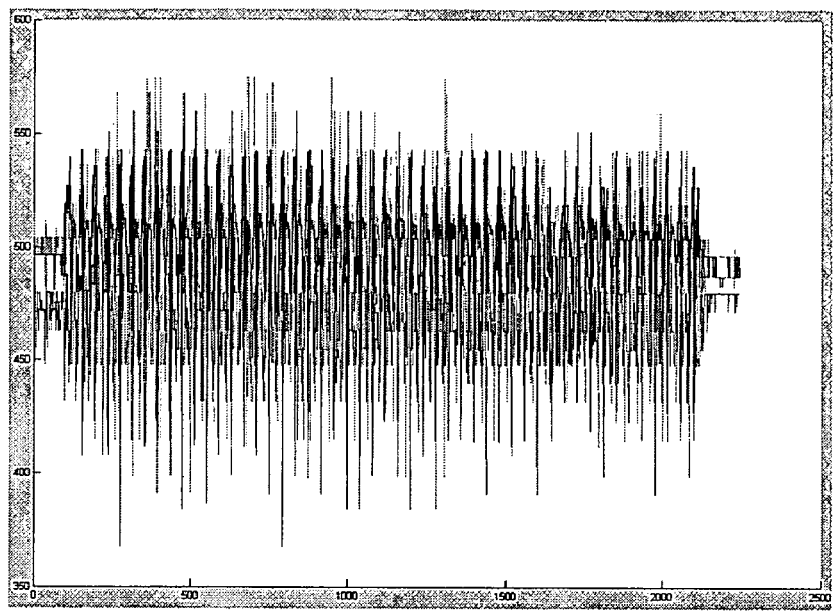
FIGS. 35A to 35F are views illustrating exemplary data used in a method for distinguishing the user's step from noise caused by external sound vibrations according to an embodiment of the present invention.
Figure 35B:
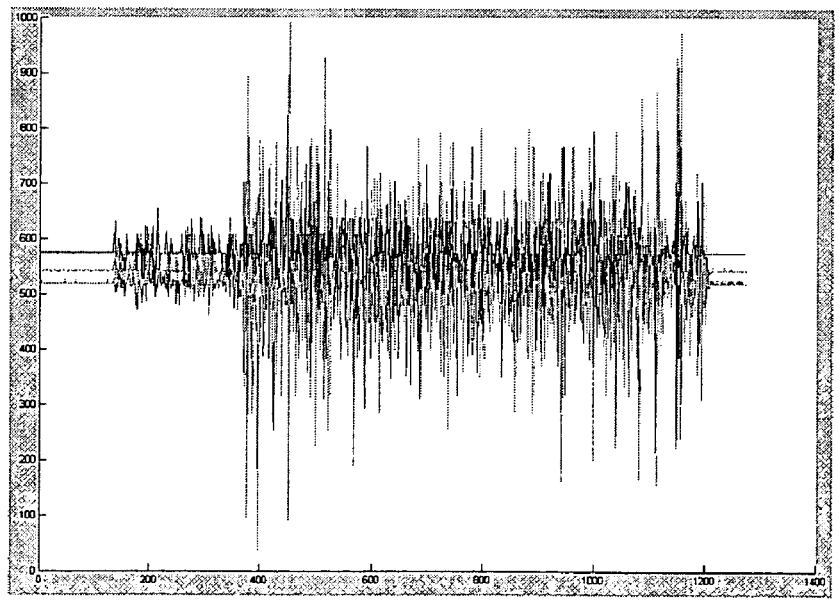
Figure 35C:
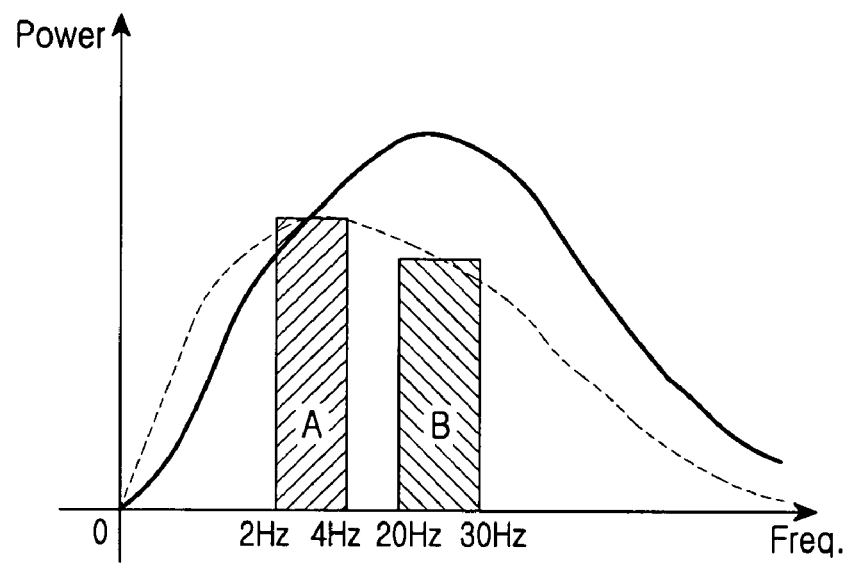
Figure 35D:
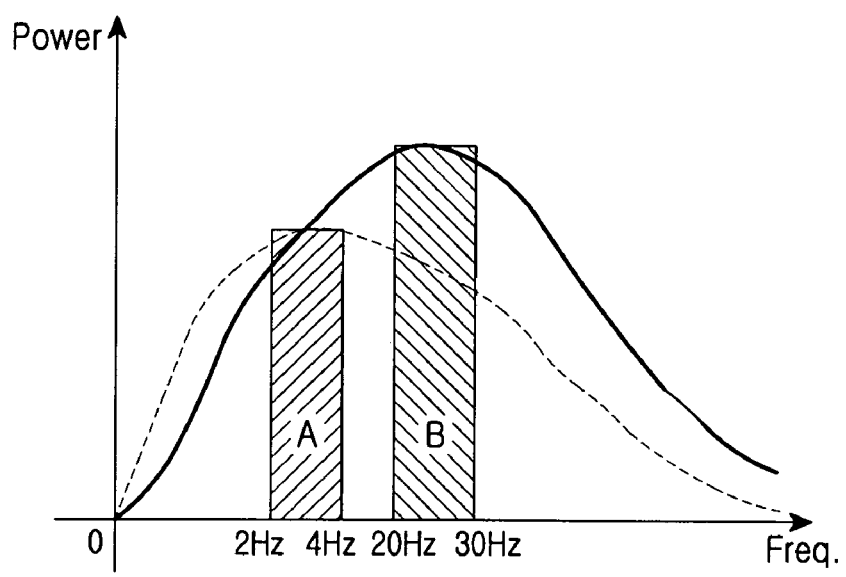

FIG. 35A is data of the three-axis acceleration sensor 153 for the step of the user and FIG. 35B is data of the three-axis acceleration sensor 153 for noise. As can be seen from FIGS. 35A and 35B, the pedometer may detect the noise as the step of the user. However, it should be noted that the frequency distribution of the step detected by the acceleration sensor 153 is different from that of the noise detected by the acceleration sensor 153. FIGS. 35C and 35D are graphs illustrating the frequency distribution of the step and noise having high sound pressure detected by the acceleration sensor 153. In FIGS. 35C and 35D, a dotted line represents the frequency distribution of the step and a solid line represents the frequency distribution of the noise. The pedometer may detect the step of the user through the frequency analysis. Thus, in the case of noise having high sound pressure, high energy can be found in the frequency band of 2 Hz to 4 Hz, which is the frequency band for the step. That is, the pedometer detects the step of the user based on the signal shown in an "A" region of FIGS. 35C and 35D. Accordingly, if the noise having the high energy is transferred to the pedometer, the pedometer may detect the noise as the step of the user.

Figure 35E:
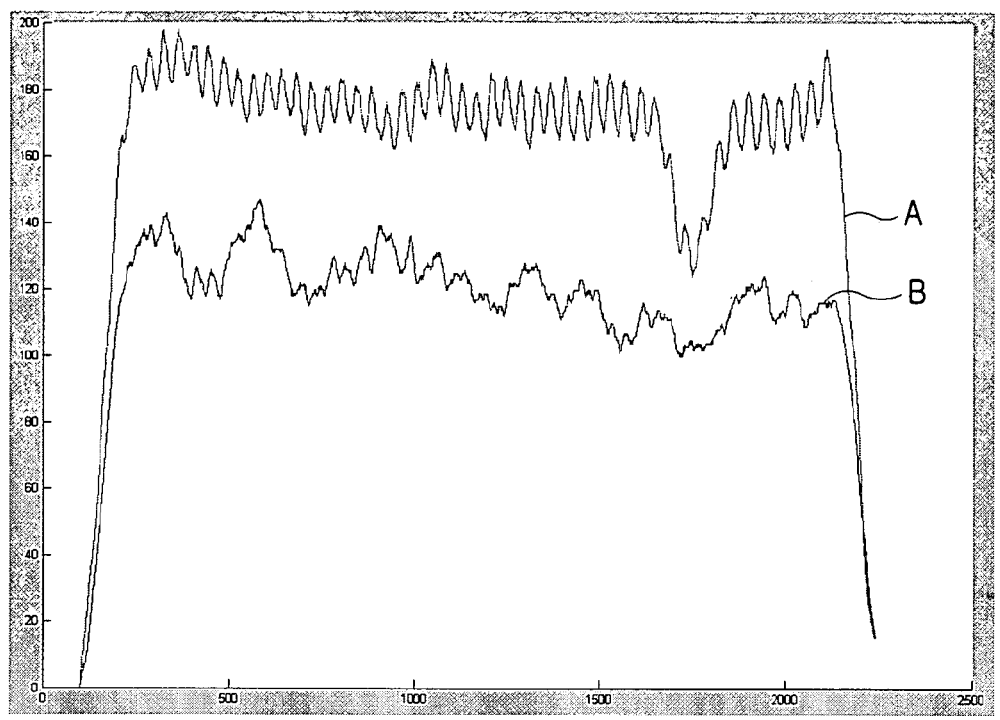
Figure 35F:
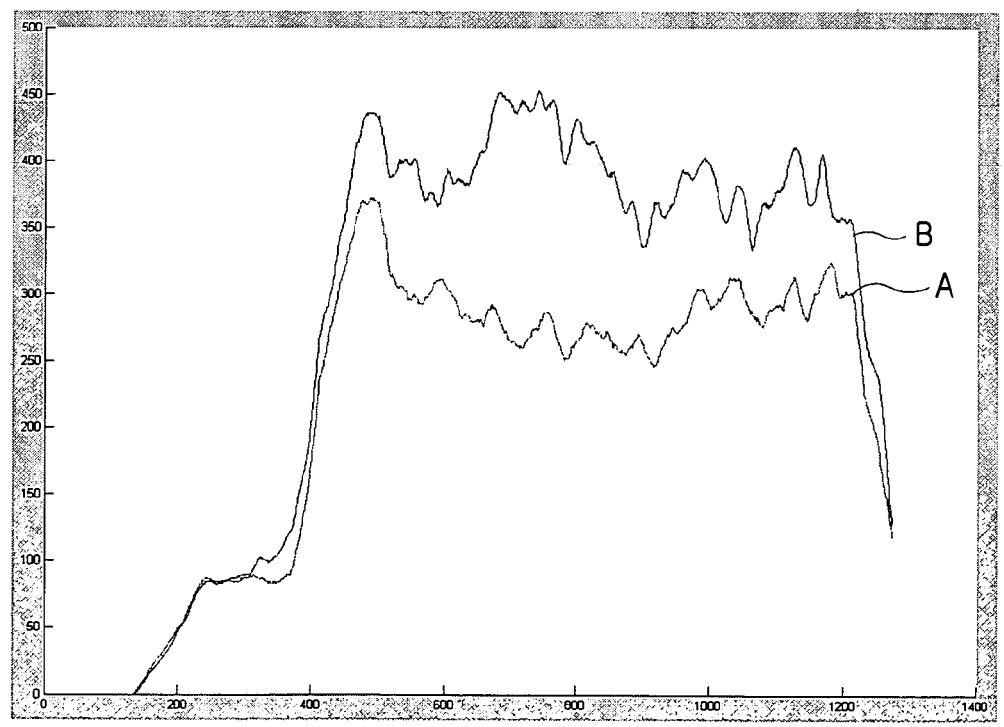

However, the energy of the step becomes reduced as it reaches the high frequency band, but the energy of the noise is concentrate on the high frequency band. That is, the step mainly represents low frequency components as shown in FIGS. 35C and 35E and the noise mainly represents low frequency components as shown in FIGS. 35D and 35F. Therefore, according to an embodiment of the present invention, the pedometer regards the signal as the step of the user when the energy level in the A region is larger than the energy level in the B region after comparing them with each other (FIG. 35E). In addition, the pedometer regards the signal as the noise when the energy level in the A region is smaller than the energy level in the B region (FIG. 35F). Thus, the pedometer according to an embodiment of the present invention can be prevented from malfunctioning when detecting noise and the step of the user.

Hereinafter, a method for preventing the pedometer from malfunctioning due to an operation of the portable terminal equipped with the pedometer will be described. When the user operates a key button or opens a folder (slider or flip) in order to make a call or perform the functions of the portable terminal, the portable terminal may apply impact to the pedometer having characteristics identical to the characteristics of the step of the user. Accordingly, when the user operates the keys or opens/closes the folder (slider or flip), the operation of the pedometer is temporarily stopped by shutting off power being supplied to the pedometer.

Hereinafter, the operation of the pedometer capable of preventing malfunction thereof by using the acceleration sensor 153 will be described in detail.

Figure 36:
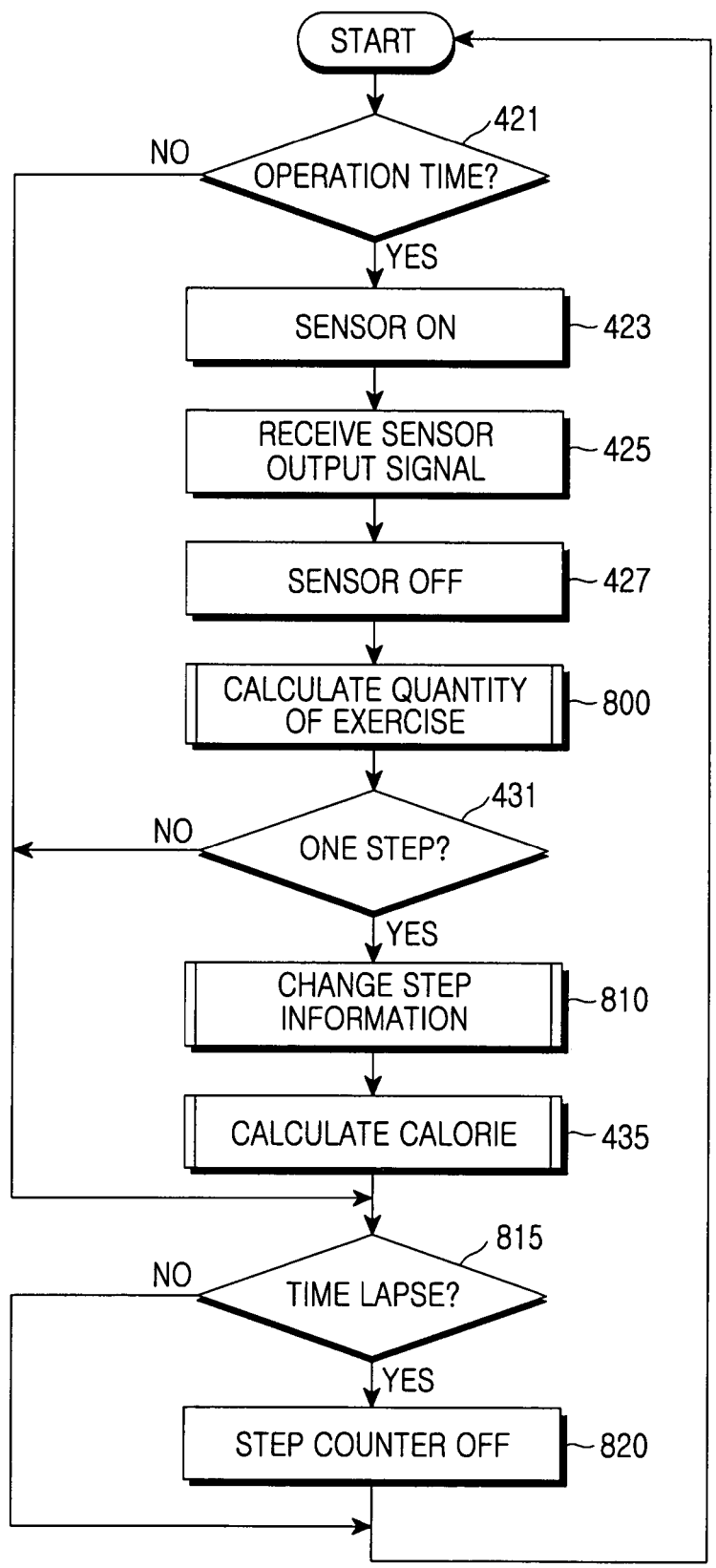
FIG. 36 is a flowchart illustrating an operational procedure for a pedometer capable of measuring the quantity of exercise by distinguishing the user's step from noise caused by external factors according to an embodiment of the present invention.

FIG. 36 is a flowchart illustrating an operational procedure of the pedometer for preventing malfunction of the pedometer according to an embodiment of the present invention. The procedure shown in FIG. 36 is similar to the procedure shown in FIG. 9.

Figure 37:
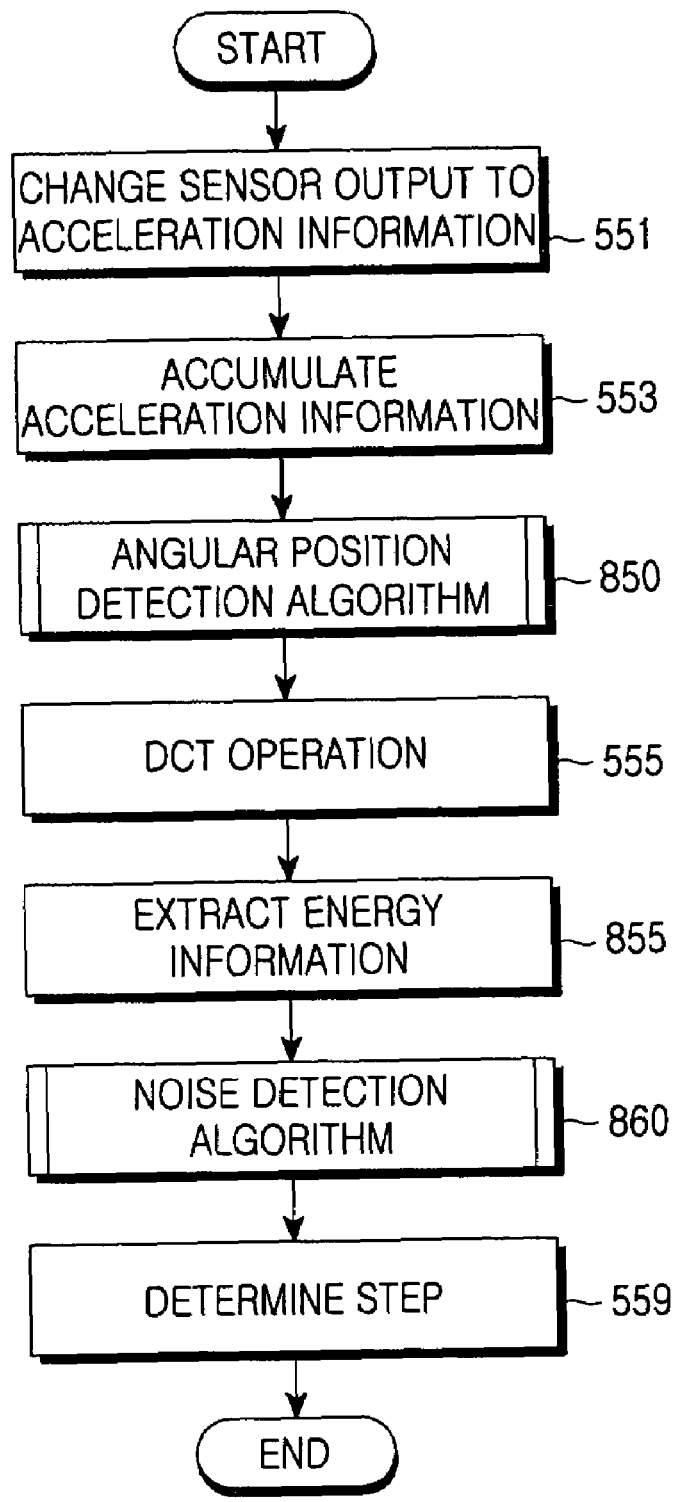
FIG. 37 is a flowchart illustrating a procedure for calculating the quantity of exercise while eliminating noise caused by external sound or variations in the angular position of a portable terminal according to an embodiment of the present invention.

Referring to FIG. 36, when the pedometer is driven, the controller 511 of the pedometer samples the output of the acceleration sensor 153 while intermittently controlling power applied to the acceleration sensor 153 (steps 421 to 427). Then, the controller 151 calculates the quantity of exercise output from the acceleration sensor 153 (step 800). At this time, the controller 151 determines the step of the user by taking the angular position of the pedometer and external noise having high sound pressure into consideration. FIG. 37 is a flowchart illustrating a procedure of the pedometer controller 151 for calculating the quantity of exercise.

Figure 38:
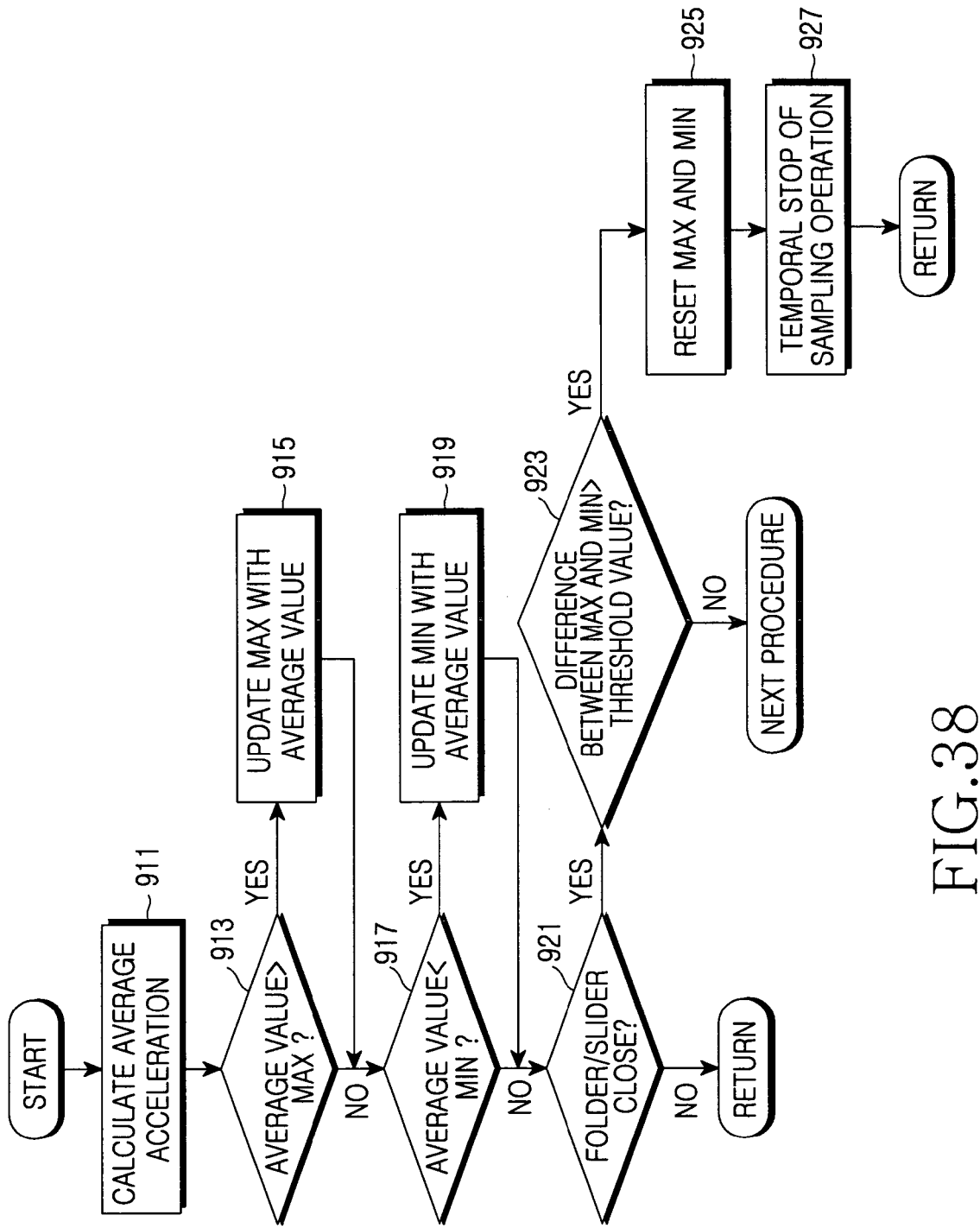
FIG. 38 is a flowchart illustrating a procedure for analyzing variation in angular position of a portable terminal according to an embodiment of the present invention.

Referring to FIG. 37, the pedometer controller 151 converts the signal generated from the acceleration sensor 153 into acceleration information and accumulates the acceleration information (similar to steps 551, 553 and 555) in the same manner as the procedure shown in FIG. 10. Then, the pedometer controller 151 analyzes the accumulated acceleration information in order to check whether the acceleration information is derived from the change of the angular position of the pedometer or exercise of the user. FIG. 38 is a flowchart illustrating a procedure of the pedometer controller 151 for analyzing variation of angular positions of the pedometer.

Referring to FIG. 38, the pedometer controller 151 calculates an average of a predetermined number of the accumulated acceleration values (step 911), in order to detect from the acceleration information if any change occurs in the gradient of the acceleration signal. When the average is obtained from a large number of the acceleration values, the acceleration signal changes with a small gradient and it is necessary for the internal memory to have a large capacity. When the average is obtained from a small number of the acceleration values, the average value has ripple and the change can be detected from the angle change of the pedometer even while the user walks. The number of the acceleration values used for calculating the average value can be obtained through experimentation, although 60 acceleration values is used to calculate the average value in the present embodiment. Thereafter, the pedometer controller 151 determines if the obtained average value is larger than the previous maximum value (step 913) and sets the average value as a maximum value when the average value is larger than the previous maximum value (step 915). Then, in step 917, the controller 151 examines if the obtained average value is smaller than the previous minimum value. When the average value is smaller than the previous minimum value, the controller sets the average value as a minimum value in step 919. In other words, in steps 913 through 919, the maximum value is updated with the current average value when the average value is larger than the previous maximum value and the minimum value is updated with the average value when the average value is smaller than the previous minimum value. When the current average value is between the previous maximum value and the previous minimum value, the controller does not change the maximum and minimum values.

Thereafter, in step 921, the controller 151 checks if the folder or slide cover is closed on the portable terminal or if the portable terminal is in a waiting state without performing communications. When the folder or slide cover is not closed on the portable terminal, the controller 151 stops the process of calculating the movement of the user and returns to the main routine of FIG. 36. When the folder or slide cover is closed on the portable terminal, the controller 151 checks if the difference between the maximum value and the minimum value for the average value is larger than a predetermined threshold value (step 923). When the difference is not larger than the predetermined threshold value, the controller 151 stops the routine shown in FIG. 28 and proceeds to step 555 of FIG. 37. Step 921 is only for a portable terminal equipped with a pedometer and may be omitted for a pedometer. That is, only in the case of the portable terminal, the folder or slide cover can be moved in order to operate the portable terminal and the acceleration sensor 153 can detect such movement and report it to the controller 151. However, in the case of the pedometer having the construction as shown in FIG. 1, it is unnecessary to perform the above process, so the pedometer may omit the operation as in step 921.

However, when the difference is not larger than the predetermined threshold value, the controller 151 detects it in step 923, initializes the maximum value and the minimum value in step 925, suspends the operation of the pedometer by stopping the power supply to the acceleration sensor 153 during a predetermined time interval, and then returns to the main routine of FIG. 36.

Referring to FIGS. 34A and 34B showing the operation in steps 923 through 927, the output of the acceleration sensor 153 by steps is produced as shown in FIG. 34A. Therefore, when acceleration values of the 60 samples of user steps are accumulated and averaged, the average maximum and minimum values of the 60 samples are within a range defined by predetermined threshold values. However, as shown in FIG. 34B, the acceleration information according to the angle change of the pedometer shows a large change in gradients of the sensor signal for two axes. Therefore, the maximum value and minimum value for the average of the accelerations of the 60 samples become larger than the predetermined threshold values. That is, if the interval between t1 and t2 in FIG. 34B includes 60 samples, the maximum value for the average value may be generated at a time point t1 and the minimum value may be generated at the time point t2. In this case, the maximum value and the minimum value between t1 and t2 may be larger than the predetermined threshold values. Then, the controller 153 initializes the maximum value and the minimum value and temporarily stops the operation of the pedometer up to the predetermined time point t3. The time period (from t2 to t3) during which the pedometer is temporarily stopped can be determined through experimentation and will be assumed to be 3 seconds in the present embodiment. Therefore, the controller 151 performs control in such a manner that the output of the acceleration sensor 153 generated by the angle change of the pedometer or portable terminal (such as due to such an action of putting on the pedometer or portable terminal on the waist or putting them into a pocket) should not be detected as being a user step.

Figure 39:
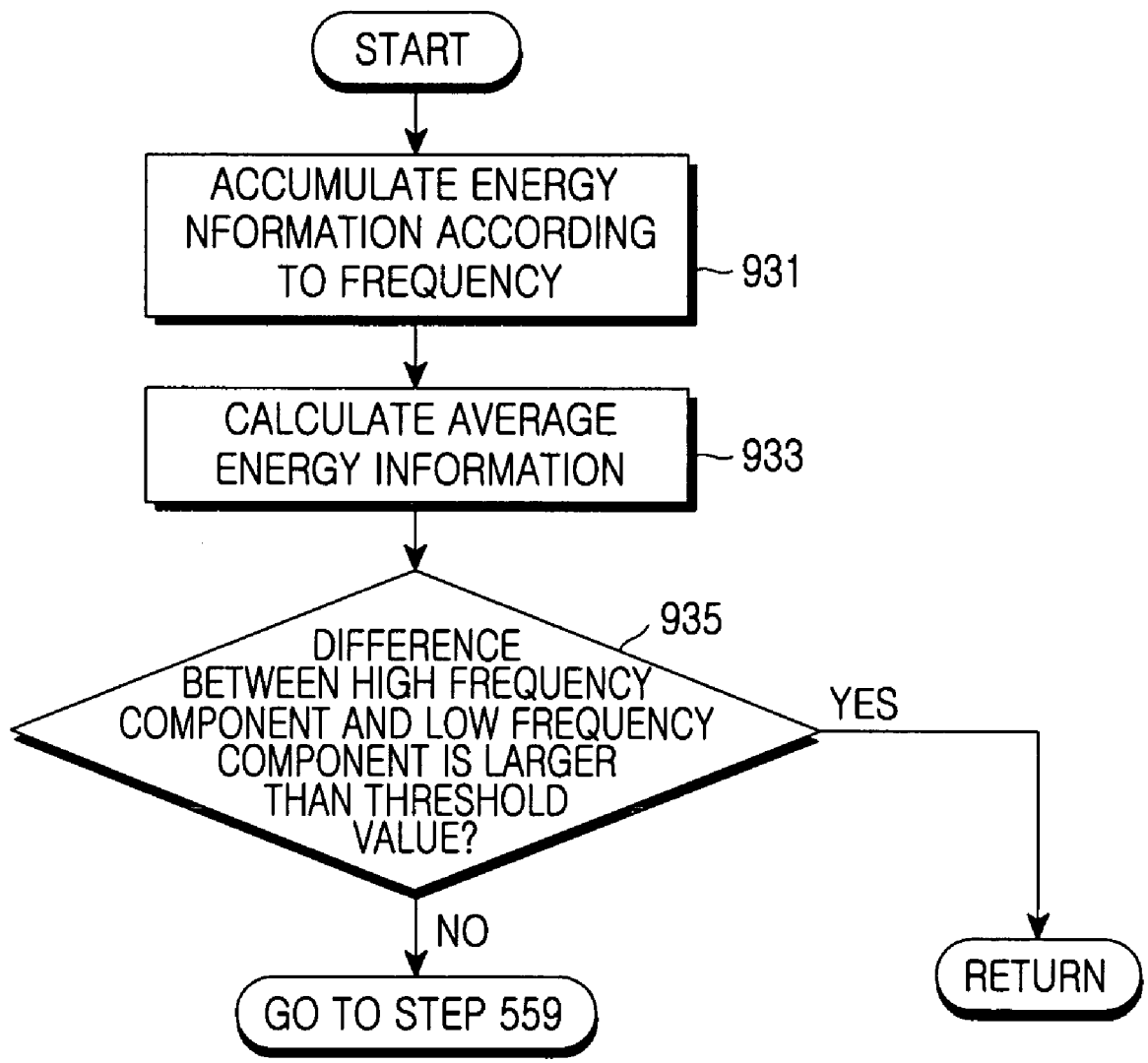
FIG. 39 is a flowchart illustrating a procedure for analyzing noise caused by external sounds according to an embodiment of the present invention.

As a result of the angular position monitoring performed in step 850 of FIG. 37 if a change is detected in the angle of the pedometer, when the controller 151 DCT-converts the accumulated acceleration information by Equation 4 in the same way as in FIG. 10 (step 555) and extracts the energy information of a low frequency and a high frequency as shown in Equation 8 from the DCT information. That is, although only the energy information of the low frequency is extracted in step 557 of FIG. 9 as shown in Equation 5, the energy information of the high frequency is extracted together with the energy information of the low frequency in step 855 in order to determine if the extracted energy information relates to the energy caused by the step or the energy caused by external sound pressure. Then, the pedometer controller 151 determines if the extracted energy information is result of the energy caused by the step or the energy is caused by external sound pressure (step 860). Further, when the extracted energy information relates to the energy caused by a step from the determination in step 860, the pedometer controller 151 determines the movement as steps in step 559 and proceeds to step 431 of FIG. 36. FIG. 39 is a flowchart illustrating a procedure for determining if the energy information relates to the energy caused by external sound pressure.

$$E_{low} = \sum_{k=1}^{5} (|P_x(k)| + |P_x(k)| + |P_x(k)|)$$

Equation 8

$$E_{high} = \sum_{k=6}^{7} (|P_x(k)| + |P_x(k)| + |P_z(k)|)$$

Referring to FIG. 39, the controller 151 accumulates the energy information separately for the high frequency and the lower frequency in step 931, calculates average values of the recent high frequency energy and low frequency energy in step 933, and determines in step 935 if the average value of the high frequency energy is larger by at least a predetermined threshold value than the average value of the low frequency energy. When the average value of the high frequency energy is larger by at least the predetermined threshold value than the average value of the low frequency energy, the controller 151 determines the energy as being caused by external sound pressure and returns to the main routine of FIG. 36. When the average value of the high frequency energy is smaller than the average value of the low frequency energy or larger than the average value of the low frequency energy by an amount smaller than the predetermined threshold value, the pedometer controller 151 determines the energy as being caused by a step and proceeds to step 559.

As shown in FIGS. 35C and 35D, because the acceleration by the step has a lower frequency than the frequency of the acceleration by the sound pressure, the pedometer controller 151 separately extracts the energy information of the frequency band by the step and the energy information of the frequency band by the sound pressure as shown in Equation 8, calculates the average values of the extracted energy information, and then compares the two average values. When the average energy value of the lower frequency band as shown by the dotted line in FIG. 35C is larger than that of the higher frequency band, the controller determines the extracted energy information as the energy by the step. When the average energy value of the higher frequency band as shown by the solid line in FIG. 35D is larger by more than the threshold value than that of the lower frequency band, the controller determines the extracted energy information as the energy by the external sound pressure, thereby preventing the number of the steps from increasing.

Figure 40:
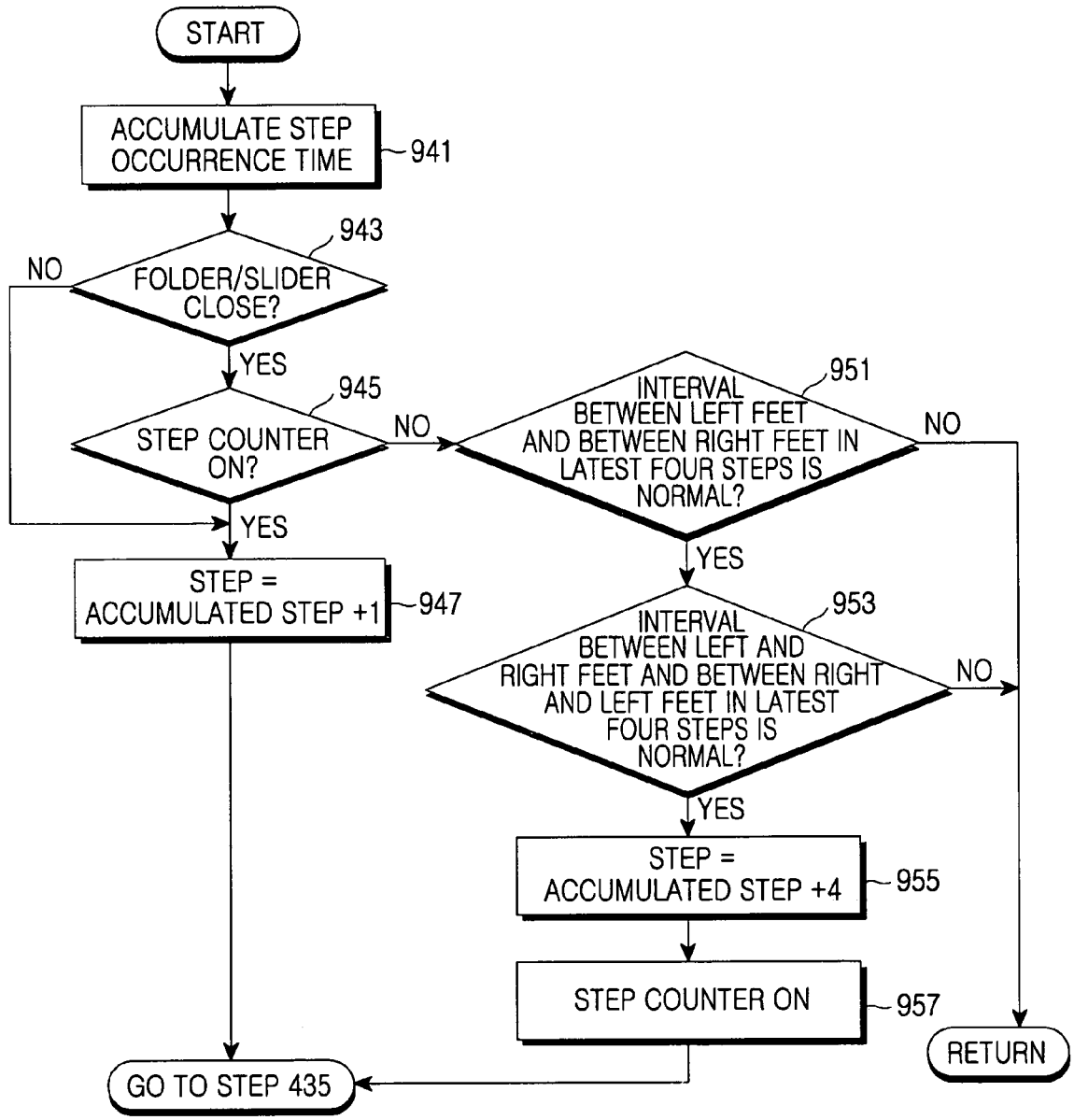
FIG. 40 is a flowchart illustrating a procedure for analyzing noise caused by external impacts according to an embodiment of the present invention.

When it is determined that the quantity of exercise calculated in step 800 of FIG. 36 corresponds to one step, the controller 151 changes the information about the number of steps in step 810. FIG. 40 is a flowchart illustrating a procedure for changing the information about the number of steps in step 810 of FIG. 36.

Referring to FIG. 40, when it is determined that the number of steps is one (1) in step 431 of FIG. 36, the controller 151 stores the current time point of determining the number of steps in step 941. Then, the controller 151 checks if the folder or sliding cover of the portable terminal is closed (step 943). Step 943 is performed only by the portable terminal equipped with the pedometer and can be omitted for a simple pedometer. Next, in step 945, the controller checks if the step counter is on. The step counter is a counter for accumulating and storing the number of steps, which is turned off when it does not receive step information within a predetermined time interval. Therefore, in a state in which the step counter is on, the controller 151 determines that the previous state is a state in which the user is walking, adds one to the value of the step counter, and then proceeds to step 435 of FIG. 36.

However, in step 945, if the step counter is an off-state, the user does not walk in the previous state. Then, when the step counter is an off-state, the controller 151 inspects the latest step occurrence time (steps 951 and 953). That is, in step 951, the controller 151 inspects the time interval between steps of left feet and between steps of right feet and checks whether the time interval (adaptable for three steps) is within a predetermined range. In addition, in step 953, the controller 151 inspects the time interval between left and right feet and between right and left feet and checks whether the time interval (adaptable for two steps) is within a predetermined range. That is, as shown in FIG. 33B, the stride of the right foot may be different from that of the left foot. This is because the right-footed person walks about the left foot thereof and the left-footed person walks about the right foot thereof. Thus, as show in FIG. 33B, the time interval per every two steps (d1 and d2) and every three steps (d3) are inspected. Although the present invention has been described that both of steps 951 and 953 are performed, it is also possible to perform only one of steps 951 and 953. In this case, when the time interval per every two steps is analyzed in step 953, the threshold time is set longer than the time interval (d2) which is longer than the time interval (d1). According to an embodiment of the present invention, the number of steps required for determining the step of the user after a predetermined standstill is "4". Thus, if steps having a predetermined time interval continuously occur for at least four times, the pedometer controller 151 determines that a user step has occurred.

If the step occurrence time of the steps set in steps 951 and 953 does not satisfy with the predetermined threshold time, the pedometer controller 151 disregards the steps and returns to the procedure shown in FIG. 36. The above phenomenon may be derived from undesired external impacts applied to the pedometer as shown in FIG. 23C. That is, if the impact is applied to the table when the pedometer is placed on the table, the acceleration sensor 153 generates output signals corresponding to the impact. At this time, as shown in FIG. 33C, the time interval of the impact is irregularly represented and the number of impacts is less than the predetermined number (that is, 4).

However, if the step occurrence time of the predetermined number of steps (at least four) set in steps 951 and 953 satisfies the predetermined threshold time, the controller 151 of the pedometer detects it and accumulates the number of steps in step 955. In addition, the controller 151 turns on the step counter in step 957 thereby counting the number of the steps. At this time, as shown in FIG. 33C, the step counter does not count the first three-steps (that is, 1, 2, 3 and 11, 12, 13 in FIG. 33C), but counts the fourth step of the user as "4" (that is, 4 and 14 in FIG. 33C).

After changing the information related to the number of steps as shown in FIG. 40, the pedometer controller 151 calculates the calorie consumption corresponding to the step (step 435) in the same manner as the procedure shown in FIG. 9. At this time, if the number of steps is set to "4" in step 955, the controller 151 multiplies the calorie consumption calculated in step 435 by 4, thereby accumulating the calorie consumption.

Referring back to FIG. 36, after calculating the calorie consumption, the pedometer controller 151 checks whether the step information is received within a predetermined period of time (step 815). In general, the person walks with a constant time interval. Thus, if the step information is not received within the predetermined period of time, the pedometer controller 151 detects it in step 815 as shown in FIG. 36 and turns off the step counter (step 820). Then, the pedometer controller 151 returns to step 421. That is, when the person stops walking or exercising, the step counter is turned off in such a manner that the pedometer may not erroneously regard vibration or impact as the step of the user. Accordingly, if the step information is not received within the predetermined period of time, the pedometer controller 151 stops the operation of the step counter and waits for the information including impacts regularly generated with a predetermined number and a predetermined time interval.

Figure 41:
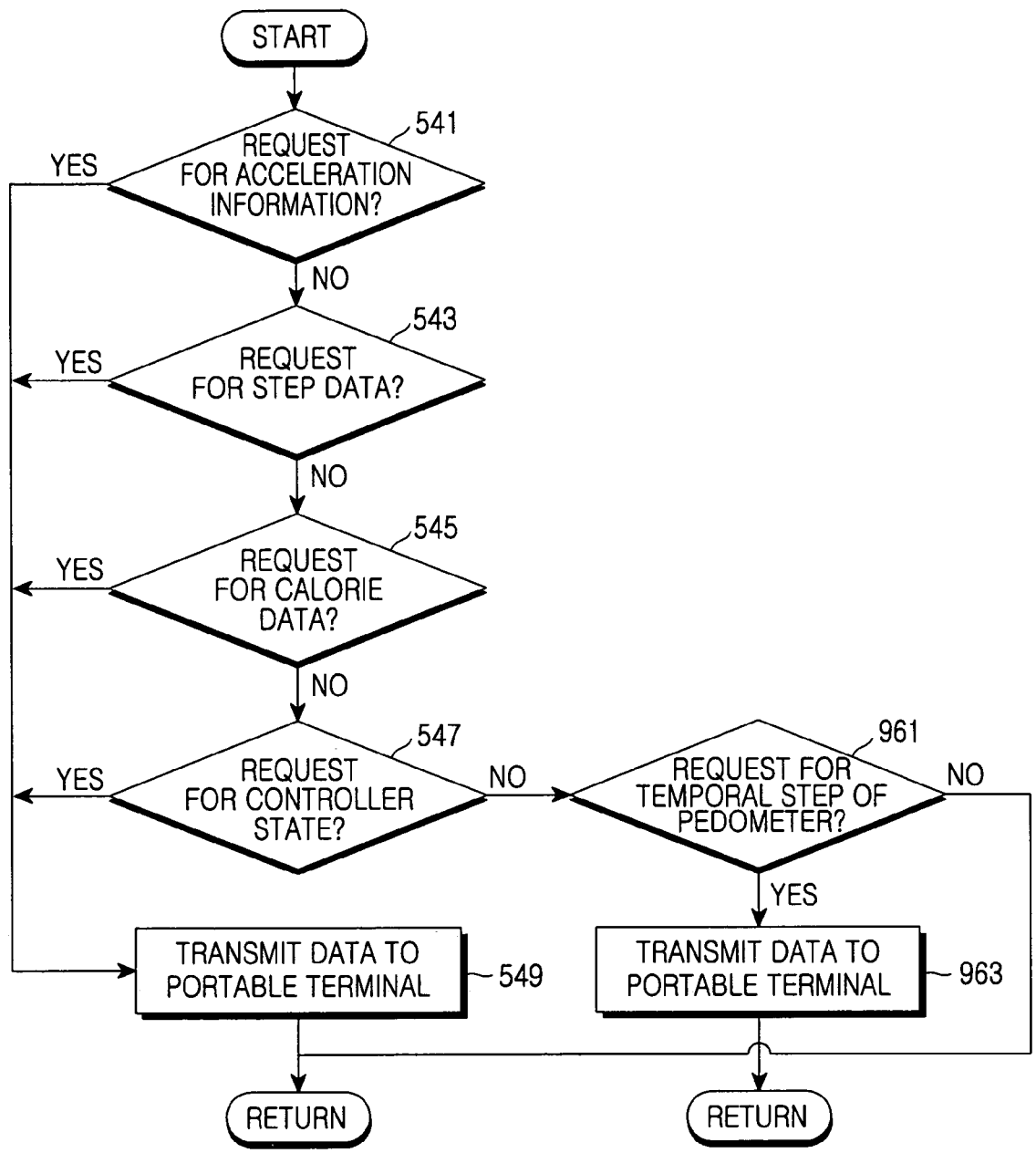
FIG. 41 is a flowchart illustrating a procedure for temporarily stopping an operation of a pedometer when a portable terminal is in an operation mode according to an embodiment of the present invention.

In addition, the portable terminal equipped with the pedometer according to an embodiment of the present invention temporarily stops the operation of the pedometer 150 when the portable terminal operates by controlling the pedometer controller 151 of the pedometer using the controller 110 of the portable terminal. FIG. 41 is a flowchart illustrating a procedure of the pedometer controller 151 for temporarily stopping the operation of the pedometer under the control of the controller of the portable terminal.

Figure 42:
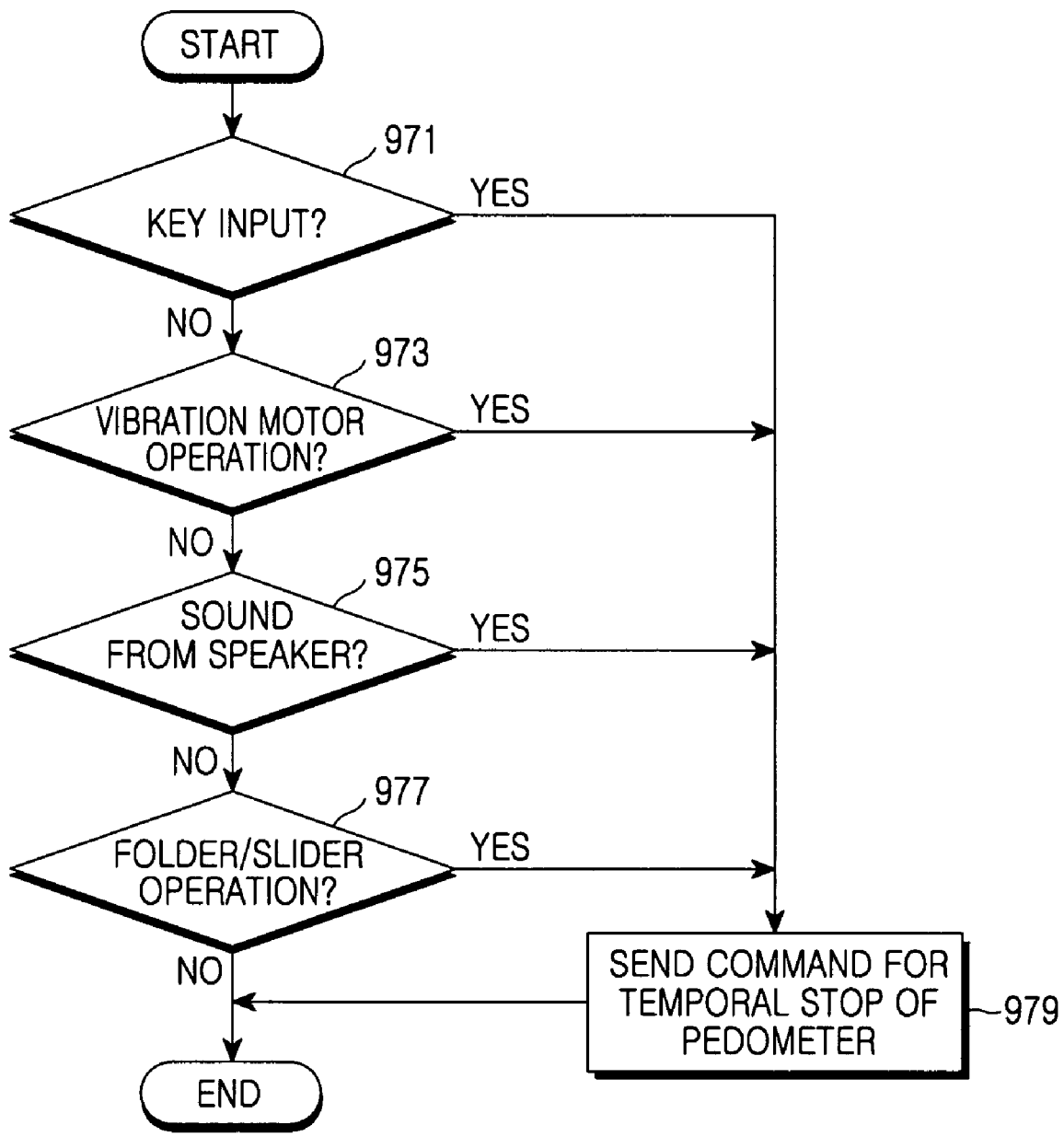
FIG. 42 is a detailed flowchart illustrating a procedure for temporarily stopping an operation of a pedometer shown in FIG. 41.

Referring to FIG. 41, steps 541 to 549 are identical to steps 541 to 549 shown in FIG. 16. Besides the above control data, the controller 110 of the portable terminal can transmit control data for temporarily stopping the operation of the pedometer. The control data are generated upon a key input, a vibration mode of a portable terminal, an output of audio sound through a speaker, or an on/off operation of a folder or a slider in order to temporarily stop the sampling operation of the pedometer. FIG. 42 is a flowchart illustrating a procedure of the controller 110 for transmitting a control signal to the controller 151 in order to temporarily stop the operation of the pedometer.

Referring to FIG. 42, when the user operates the key of the portable terminal, when the motor is vibrated under the vibration mode of the portable terminal, when an audio signal is reproduced through the speaker, or when the folder or the slider is opened or closed, the controller 110 of the portable terminal detects it through steps 971 to 977 and transmits a control signal to the controller 151 to temporarily stop the operation of the pedometer. Thus, as shown in FIG. 41, the pedometer controller 151 of the pedometer detects the control signal of the portable terminal controller 110 and temporarily shuts off power being transferred to the acceleration sensor 153 for a predetermined period of time (step 961). According to an embodiment of the present invention, the predetermined period of time is about 2 to 3 second.

Figure 43:
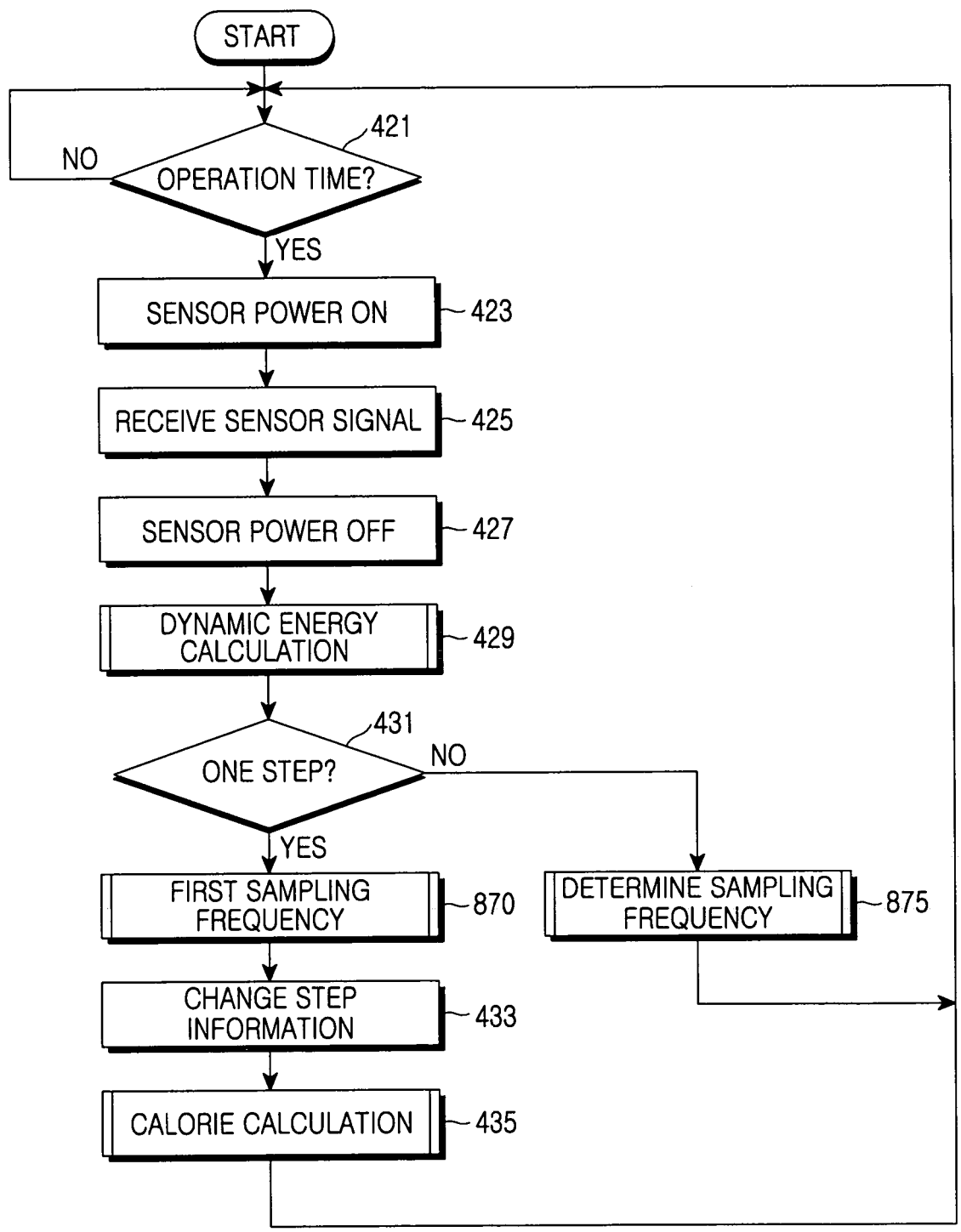
FIG. 43 is a flowchart illustrating a procedure for reducing the power consumption by changing sampling frequencies based on the operational state of a pedometer according to an embodiment of the present invention.

In addition, embodiments of the present invention can variably control the operation of the pedometer according to the operational state of the pedometer. That is, when the user walks, the sampling frequency established by the user can be used. In addition, when the user does not walk, the sampling frequency is changed in order to reduce power consumption of the pedometer. The controller 151 of the pedometer supplies power to the acceleration sensor 153 with the sampling frequency. FIG. 43 is a flowchart illustrating a procedure for reducing the power consumption by changing sampling frequencies according to an embodiment of the present invention.

Referring to FIG. 43, when it is necessary to operate the pedometer, the controller 151 detects it (step 421) and supplies power to the acceleration sensor 153 through steps 423 and 427, which is identical to the procedure shown in FIG. 9, and receives the output of the acceleration sensor 153. Then, the controller 151 of the pedometer calculates the quantity of exercise detected by the acceleration sensor 153 while performing the procedure (step 429) similar to the procedure shown in FIG. 9. After that, the controller 151 checks whether the quantity of exercise detected by the acceleration sensor 153 corresponds to the step of the user.

Figure 44:
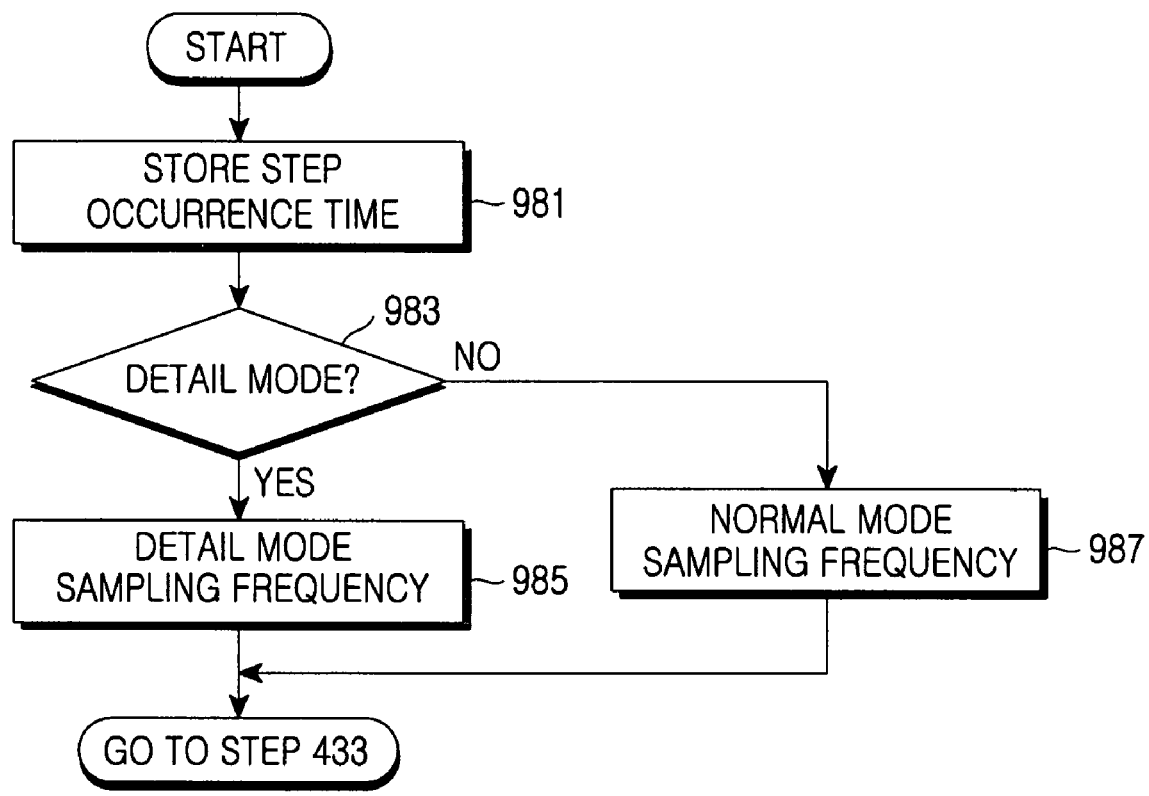
FIG. 44 is a flowchart illustrating a procedure for setting the sampling frequencies when the user's step is detected in the procedure shown in FIG. 43.

If it is determined that the quantity of exercise detected by the acceleration sensor 153 corresponds to the step of the user, the controller 151 determines the sampling frequency corresponding to the step of the user (step 870). FIG. 44 is a flowchart illustrating a procedure for setting sampling frequencies when the step of a user is detected in step 870 shown in FIG. 43. Referring to FIG. 44, the pedometer controller 151 stores the step occurrence time (step 981) and checks whether the present sampling frequency is a detail mode sampling frequency or a normal mode sampling frequency. If the present sampling frequency is the detail mode sampling frequency, the controller 151 sets the detail mode sampling frequency as the sampling frequency (step 985). In addition, if the present sampling frequency is the normal mode sampling frequency, the controller 151 sets the normal mode sampling frequency as the sampling frequency (step 987). As mentioned above, the detail mode sampling frequency of the pedometer is 36 Hz and the normal mode sampling frequency of the pedometer is 18 Hz.

Referring back to FIG. 43, the controller 151 changes the number of steps (step 433) and calculates and accumulates the calorie consumption (step 435) with the same manner as shown in FIG. 9.

Figure 45:
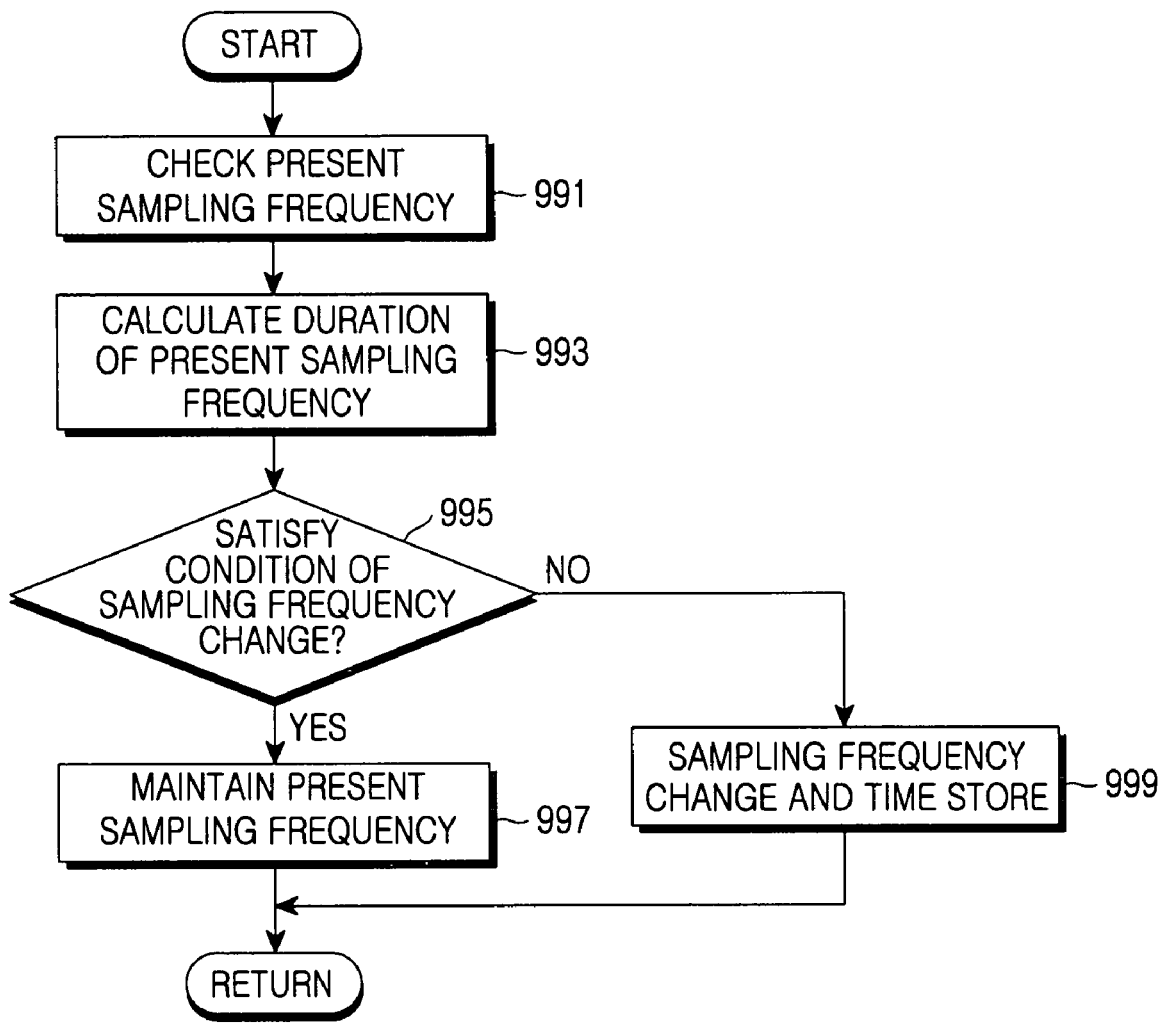
FIG. 45 is a flowchart illustrating a procedure for changing the sampling frequencies when the user's step is not detected for a predetermined period of time in the procedure shown in FIG. 43.
Figure 46:
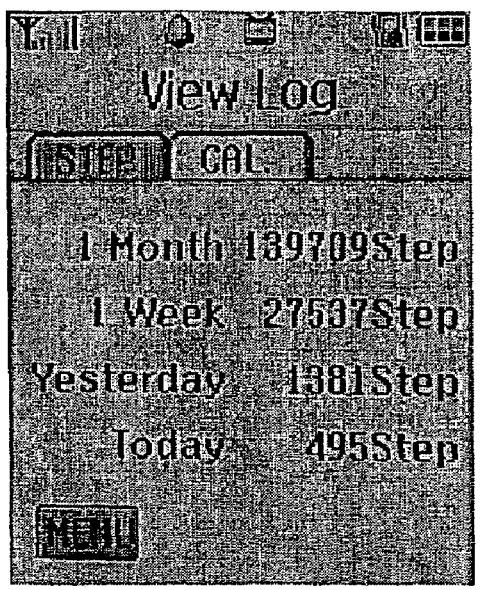
FIGS. 46A to 46J are views illustrating exemplary screen images for displaying information related to the number of steps measured in a pedometer according to an embodiment of the present invention.
Figure 46:
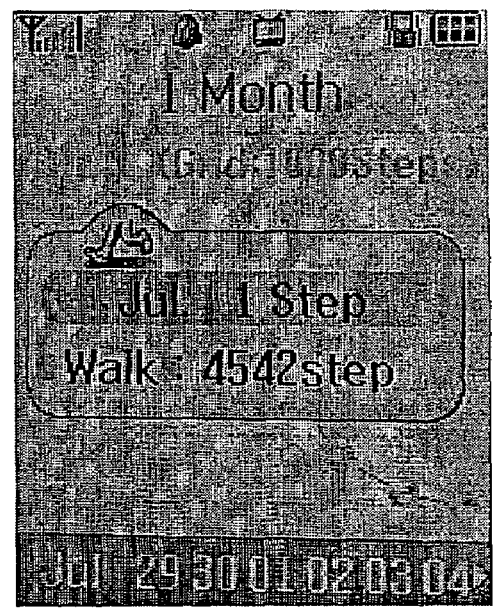
Figure 46:
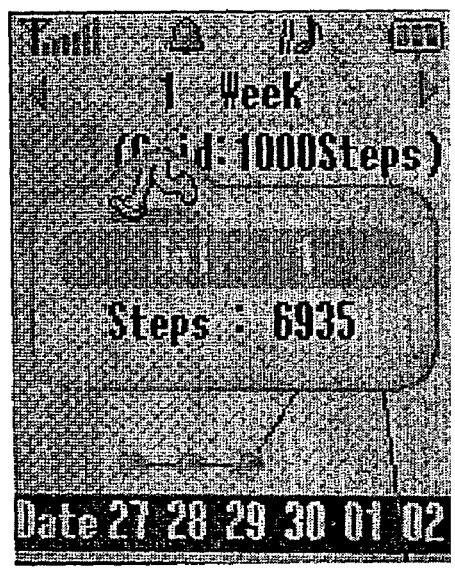
Figure 46:
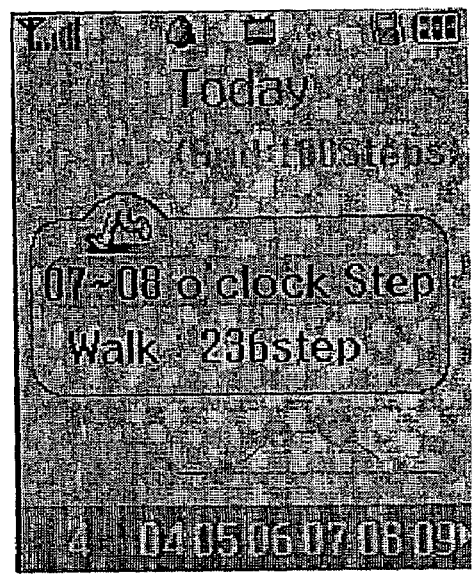
Figure 46:
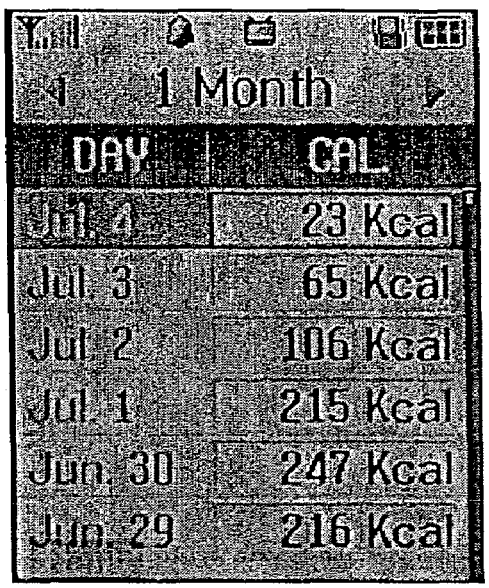
Figure 46F:
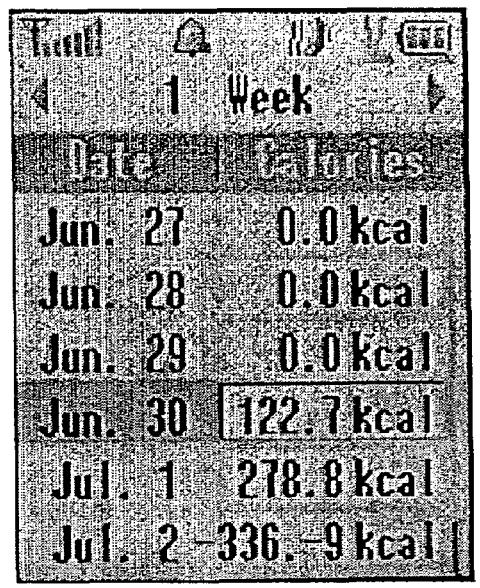
Figure 46:
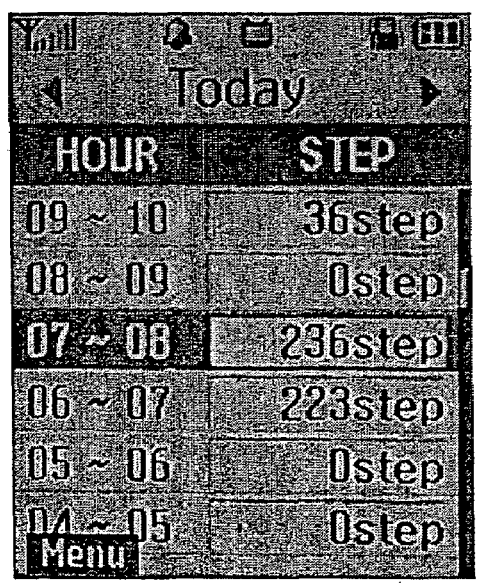
Figure 46H:
Figure 46I:
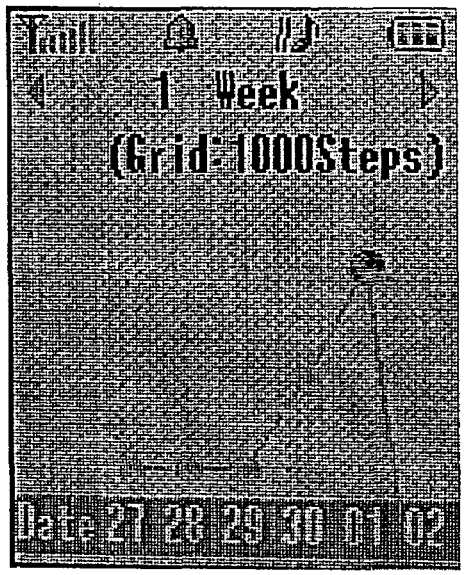
Figure 46J:
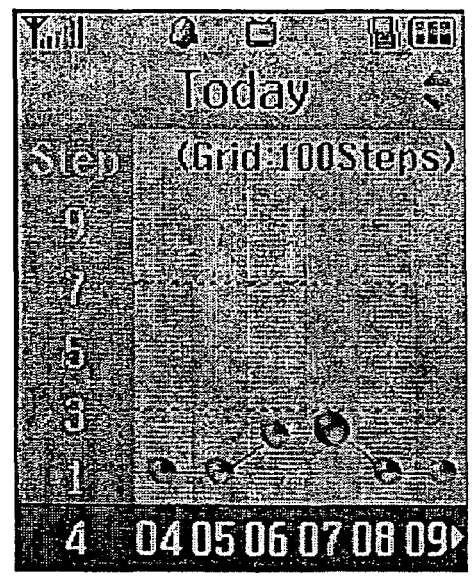

However, if it is determined in step 431 that the quantity of exercise detected by the acceleration sensor 153 does not match with the step of the user, the controller 151 checks a previous step occurrence time (step 875) and determines whether it is necessary to change the sampling frequency. FIG. 45 is a flowchart illustrating a procedure for changing sampling frequencies. Referring to FIG. 45, if it is determined in step 431 that the quantity of exercise detected by the acceleration sensor 153 does not match with the step of the user, the controller checks the present sampling frequency (step 991) and inspects the duration of the present sampling frequency (step 993). If the duration of the present sampling frequency satisfies the condition for changing the sampling frequency, the controller 151 detects it (step 995) and changes the sampling frequency (step 999). In addition, the controller 151 stores the frequency change time and returns to step 421 in FIG. 43. However, if the duration of the present sampling frequency does not satisfy the condition for changing the sampling frequency, the controller 151 sets the present sampling frequency as the sampling frequency.

As described above, according to an embodiment of the present embodiment, when the pedometer has not detected a user's step during a predetermined time interval, the sampling frequency can be lowered to reduce the current consumption. It is assumed that 36 Hz, 18 Hz, 9 Hz and 5 Hz are used as the sampling frequency. Also, the threshold time points for changing the sampling frequency may be set either equally or differently according to necessity. When it is determined that the user has walked one step, the controller 151 stores the time point at which the information is determined as relating to the user's step. Therefore, the controller 151 can confirm the time period from one step to the next step. When it is not determined that the user's walking is one step at each sampling period, the controller 151 confirms the current sampling frequency (step 991) and calculates the time interval during which the sampling frequency continues (step 993). When a signal corresponding to one step is not received during longer than the predetermined threshold time interval of the current sampling frequency, the controller 151 sets a frequency next-lower than the current sampling frequency as a new sampling frequency of the pedometer and stores the time point at which the sampling frequency is changed. Therefore, the output of the acceleration sensor 153 determined as one step is not received during the time interval set in the detail mode, the controller 151 lowers the sampling frequency in an order of 36 Hz, 18 Hz, 9 Hz and 5 Hz. In the case of a normal mode, the controller 151 lowers the sampling frequency in the order of 18 Hz, 9 Hz and, then, 5 Hz. Further, when a signal which can be determined as one step is not received even after the sampling frequency is lowered to 5 Hz, the controller 151 maintains the sampling frequency as 5 Hz. When a signal that can be determined as one step is received after the change of the sampling frequency, the controller 151 detects it in step 431 and changes the sampling frequency to the frequency of the mode set by the user in step 870 in the same process as that shown in FIG. 44, thereby operating the pedometer.

As described above, the apparatus for measuring the quantity of exercise using a pedometer according to an embodiment of the present invention can precisely measure the quantity of exercise by using the acceleration sensor. In addition, the time interval and the threshold value of the dynamic energy can be checked when measuring the quantity of exercise, so the reliability of the apparatus and the measurement value thereof can be improved. Since the quantity of exercise is measured by taking the weight of the user and the position of the pedometer into consideration, the calorie consumption can be precisely measured according to the type of exercise and the weight of the user. In addition, the operation of the acceleration sensor is intermittently controlled so that power consumption thereof can be reduced. According to an embodiment of the present invention, the quantity of exercise measured by the pedometer can be accumulated during a predetermined period of time and the user can display the accumulated data in the form of figures or graphs according to the selection of the user. Accordingly, it is possible to accumulate and manage the quantity of exercise of the user. In addition, the pedometer can be installed in the portable terminal so that the portable terminal has an additional function. The pedometer can also be individually used separately from the portable terminal. In addition, the pedometer can distinguish vibrations caused by noise and external impacts from the step of a user, so the pedometer can be prevented from erroneously counting noise or external impacts as the steps of the user. The portable terminal equipped with the pedometer can temporarily stop the operation of the pedometer when the portable terminal performs its own functions, so the reliability of the pedometer can be improved. In addition, the sampling frequency of the pedometer can be variably selected according to the state of the pedometer, thereby reducing current consumption.

While the present invention has been shown and described with reference to certain preferred embodiments thereof, it will be understood by those skilled in the art that various changes in form and details may be made therein without departing from the spirit and scope of the invention as defined by the appended claims.

What is claimed is:

1. An apparatus for measuring a quantity of exercise performed by a user, the apparatus comprising:
   an acceleration sensor for generating acceleration information by measuring the quantity of exercise according to a movement of the user as the acceleration sensor is powered on;
   a sensor control unit for supplying power to the acceleration sensor at a first predetermined time section during a second predetermined time with a first time interval and sampling the acceleration information generated from the acceleration sensor at a second predetermined time section of the second predetermined time;
   a dynamic energy measurement unit for converting the sampled acceleration information into dynamic energy and determining a step of the user by analyzing the dynamic energy; and
   a display section for displaying information related to a number of steps.

2. The apparatus as claimed in claim 1, wherein the sensor control unit samples the acceleration information of the acceleration sensor when the acceleration sensor stably outputs the acceleration information after the acceleration sensor is driven, and then shuts off power being supplied to the acceleration sensor.

3. The apparatus as claimed in claim 1, wherein the acceleration sensor is a three-axis acceleration sensor capable of generating three-axis acceleration information for detecting a movement in X, Y and Z-axis directions and the dynamic energy measurement unit combines three-axis acceleration information of the acceleration sensor in order to extract an energy component of a predetermined frequency band from the acceleration information.

4. An apparatus for measuring a quantity of exercise performed by a user, the apparatus comprising:
   an acceleration sensor for generating acceleration information by measuring the quantity of exercise according to a movement of the user;
   a sensor control unit for sampling the acceleration information generated from the acceleration sensor at a predetermined time interval;
   a dynamic energy measurement unit for converting the sampled acceleration information into dynamic energy, comparing a local maximum value with a predetermined threshold value if an ascending gradient of the dynamic energy has the local maximum value exceeding a predetermined value, and determining one step of the user if the local maximum value exceeds the predetermined threshold value; and
   a display section for displaying information related to a number of steps.

5. The apparatus as claimed in claim 4, wherein the dynamic energy measurement unit comprises an acceleration information accumulation module for accumulating acceleration information to allow the acceleration information to be subject to discrete cosine transform (DCT), a DCT module for converting the acceleration information into DCT acceleration information, an energy extracting module for combining DCT acceleration information in order to extract an energy component of a predetermined band and a determination module comparing the local maximum value with the predetermined threshold value if the ascending gradient of the dynamic energy has the local maximum value exceeding the predetermined value and determining one step of the user if the local maximum value exceeds the predetermined threshold value.

6. The apparatus as claimed in claim 5, wherein the determination module is switched from a standby state into a first state if the dynamic energy has the ascending gradient having a value exceeding a predetermined value, the determination module is switched from the first state into the standby state while determining one step of the user if the dynamic energy has the local maximum value exceeding the predetermined threshold value and a time interval between a previous local maximum value and a present local maximum value is longer than a predetermined time in the first state, and the determination module is instantly switched into the standby state if at least one of the above two conditions is not satisfied.

7. The apparatus as claimed in claim 5, further comprising a sampling interval determination module for determining a type of exercise performed by a user by comparing a level of a high frequency signal of the DCT information generated from the DCT module and a level trigger signal with a reference level and a reference level trigger signal adaptable for at least two types of exercise and for supplying a sampling frequency to the acceleration sensor by determining the sampling frequency according to the type of exercise.

8. The apparatus as claimed in claim 7, wherein the type of exercise is detected based on a time interval between steps and the sampling frequency in a fast walking mode is higher than the sample frequency in a normal walking mode.

9. The apparatus as claimed in claim 8, wherein the type of exercise includes walking, fast walking, jogging and running at full speed, and a highest sampling frequency is applied to a running at full speed mode.

10. The apparatus as claimed in claim 7, wherein the acceleration sensor is a three-axis acceleration sensor capable of generating three-axis acceleration information for detecting a movement in X, Y and Z-axis directions and the dynamic energy measurement unit combines three-axis acceleration information of the acceleration sensor in order to extract an energy component of a predetermined band from the acceleration information.

11. An apparatus for measuring a quantity of exercise performed by a user, the apparatus comprising:
    an acceleration sensor for generating acceleration information by measuring the quantity of exercise according to a movement by a user;
    a sensor control unit for supplying power to the acceleration sensor at a first predetermined time section during a second predetermined time with a first time interval and sampling the acceleration information generated from the acceleration sensor at a second predetermined time section within the second predetermined time;
    a dynamic energy measurement unit for converting the sampled acceleration information into dynamic energy, comparing a local maximum value with a predetermined threshold value if an ascending gradient of the dynamic energy has the local maximum value exceeding a predetermined value and determining one step of the user if the local maximum value exceeds the predetermined threshold value;
    a calorie consumption measurement unit for calculating calorie consumption by analyzing an energy level of dynamic energy determined as being a step of the user;
    a memory for storing information related to a number of steps generated from the dynamic energy measurement unit and the calorie consumption generated from the calorie consumption measurement unit; and a display section for displaying information related to the number of steps and calorie consumption.

12. The apparatus as claimed in claim 11, wherein the sensor control unit samples the acceleration information of the acceleration sensor when the acceleration sensor stably outputs the acceleration information after the acceleration sensor is driven, and then shuts off power being supplied to the acceleration sensor.

13. The apparatus as claimed in claim 12, wherein the acceleration sensor is a three-axis acceleration sensor capable of generating three-axis acceleration information for detecting a movement in X, Y and Z-axis directions and the dynamic energy measurement unit combines three-axis acceleration information of the acceleration sensor in order to extract an energy component of a predetermined band from the acceleration information.

14. The apparatus as claimed in claim 11, wherein the dynamic energy measurement unit comprises an acceleration information accumulation module for accumulating acceleration information to allow the acceleration information to be subject to discrete cosine transform (DCT), a DCT module for converting the acceleration information into DCT acceleration information, an energy extracting module for combining DCT acceleration information in order to extract an energy component of a predetermined band and a determination module comparing the local maximum value with the predetermined threshold value if the ascending gradient of the dynamic energy has the local maximum value exceeding the predetermined value and determining one step of the user if the local maximum value exceeds the predetermined threshold value.

15. The apparatus as claimed in claim 14, wherein the determination module is switched from a standby state into a first state if the dynamic energy has the ascending gradient having a value exceeding a predetermined value, the determination module is switched from the first state into the standby state while determining one step of the user if the dynamic energy has the local maximum value exceeding the predetermined threshold value and a time interval between a previous local maximum value and a present local maximum value is longer than a predetermined time in the first state, and the determination module is instantly switched into the standby state if at least one the above two conditions is not satisfied.

16. The apparatus as claimed in claim 15, further comprising a sampling interval determination module for determining a type of exercise performed by the user by comparing a level of a high frequency signal of the DCT information generated from the DCT module and a level trigger signal with a reference level and a reference level trigger signal adaptable for at least two types of exercise and for supplying a sampling frequency to the acceleration sensor by determining the sampling frequency according to the type of exercise.

17. The apparatus as claimed in claim 16, wherein the type of exercise is detected based on a time interval between steps and the sampling frequency in a fast walking mode is higher than the sample frequency in a normal walking mode.

18. The apparatus as claimed in claim 11, wherein the calorie consumption measurement unit has reference values of at least two energy level sections determined through an experiment corresponding to a walking speed and a calorie consumption value for each energy level section, and the calorie consumption measurement unit calculates energy level values of the energy level sections and calorie consumption values thereof by comparing measured energy level values of the energy level sections with the reference values of the energy level sections.

19. The apparatus as claimed in claim 11, wherein the calorie consumption measurement unit has reference values of at least two energy level sections according to the type of exercise and a calorie consumption value for each energy level section, and the calorie consumption measurement unit calculates energy level values of the energy level sections and calorie consumption values thereof by comparing present energy level values of the energy level sections with the reference values of the energy level sections.

20. The apparatus as claimed in claim 19, wherein the calculated calorie consumption is updated by taking a weight of the user into consideration.

21. The apparatus as claimed in claim 20, wherein the values of the level sections of the calorie consumption measurement unit are preset by means of the acceleration sensor according to a position of a portable terminal.

22. The apparatus as claimed in claim 11, wherein the memory comprises 24 time memories, 31 day memories and 12 month memories, information related to the number of steps generated from the dynamic energy measurement unit and calorie consumption generated from the calorie consumption measurement unit are stored in the time memories corresponding to measurement time thereof, information related to the number of steps and calorie consumption stored in the time memories are stored in the day memory when a date is changed, and information related to the number of steps and calorie consumption stored in the day memories are stored in the month memory when a month is changed.

23. A portable terminal for performing communication functions and measuring a quantity of exercise performed by a user, portable terminal comprising:
    a RF communication section for up-converting a transmission signal into an RF band signal and down-covering a RF signal into a base band signal;
    a data processing section for coding and modulating the transmission signal and decoding and demodulating the base band signal;
    an acceleration sensor for generating acceleration information by measuring the quantity of exercise according to a motion of a user;
    a pedometer controller for sampling the acceleration information generated from the acceleration sensor at a predetermined time of an operation mode, determining a step of the user by extracting dynamic energy from the sampled acceleration information, and calculating calorie consumption based on energy level of dynamic energy determined as the step of the user;
    a portable terminal controller for transmitting the operation mode and position information to the pedometer controller so as to control an operation of a pedometer and requesting data transmission for a number of measured steps to the pedometer controller;
    a memory for storing information related to the number of measured steps; and
    a display section for displaying information related to the number of steps.

24. The portable terminal as claimed in claim 23, wherein the pedometer controller comprises a sensor control unit for supplying power to the acceleration sensor at a first predetermined time section during a second predetermined time with a first time interval and sampling the acceleration information generated from the acceleration sensor at a second predetermined time section of the second predetermined time and a dynamic energy measurement unit converting the sampled acceleration information into dynamic energy, comparing a local maximum value with a predetermined threshold value if an ascending gradient of the dynamic energy has the local maximum value exceeding a predetermined value and determining that one step is taken by the user if the local maximum value exceeds the predetermined threshold value.

25. The portable terminal as claimed in claim 24, wherein the sensor control unit samples the acceleration information of the acceleration sensor when the acceleration sensor stably outputs the acceleration information after the acceleration sensor is driven, and then shuts off power being supplied to the acceleration sensor.

26. The portable terminal as claimed in claim 25, wherein the acceleration sensor is a three-axis acceleration sensor capable of generating three-axis acceleration information for detecting a movement in X, Y and Z-axis directions and the dynamic energy measurement unit combines the three-axis acceleration information of the acceleration sensor in order to extract an energy component of a predetermined band from the acceleration information.

27. The portable terminal as claimed in claim 23, wherein the dynamic energy measurement unit comprises an acceleration information accumulation module for accumulating acceleration information to allow the acceleration information to be subject to discrete cosine transform (DCT), a DCT module for converting the acceleration information into DCT acceleration information, an energy extracting module for combining DCT acceleration information in order to extract an energy component of a predetermined band and a determination module comparing the local maximum value with the predetermined threshold value if the ascending gradient of the dynamic energy has the local maximum value exceeding the predetermined value and determining that one step is taken by the user if the local maximum value exceeds the predetermined threshold value.

28. The portable terminal as claimed in claim 27, wherein the determination module is switched from a standby state into a first state if the dynamic energy has the ascending gradient having a value exceeding a predetermined value, the determination module is switched from the first state into the standby state while determining one step of the user if the dynamic energy has the local maximum value exceeding the predetermined threshold value and a time interval between a previous local maximum value and a present local maximum value is longer than a predetermined time in the first state, and the determination module is instantly switched into the standby state if at least one of the above two conditions is not satisfied.

29. The portable terminal as claimed in claim 15, further comprising a sampling interval determination module for determining a type of exerciser of the user by comparing a level of a high frequency signal of the DCT information generated from the DCT module and a level trigger signal with a reference level and a reference level trigger signal adaptable for at least two types of exercise and for supplying a sampling frequency to the acceleration sensor by determining the sampling frequency according to the type of exercise.

30. The portable terminal as claimed in claim 29, wherein the type of exercise is detected based on a time interval between steps and the sampling frequency in a fast walking mode is higher than the sample frequency in a normal walking mode.

31. The portable terminal as claimed in claim 23, further comprising a calorie consumption measurement unit, wherein the calorie consumption measurement unit has reference values of at least two energy level sections determined through an experiment corresponding to a walking speed and a calorie consumption value for each energy level section, and the calorie consumption measurement unit calculates energy level values of the energy level sections and calorie consumption values thereof by comparing measured energy level values of the energy level sections with the reference values of the energy level sections.

32. The portable terminal as claimed in claim 31, wherein the calculated calorie consumption is updated by taking a weight of the user into consideration.

33. The portable terminal as claimed in claim 32, wherein the values of the level sections of the calorie consumption measurement unit are preset by means of the acceleration sensor according to a position of the portable terminal.

34. The portable terminal as claimed in claim 23, wherein the memory includes 24 time memories, 31 day memories and 12 month memories, information related to the number of steps generated from the dynamic energy measurement unit and calorie consumption generated from the calorie consumption measurement unit are stored in the time memories corresponding to measurement time thereof, information related to the number of steps and calorie consumption stored in the time memories are stored in the day memory when a date is changed, and information related to the number of steps and calorie consumption stored in the day memories are stored in the month memory when a month is changed.

35. The portable terminal as claimed in claim 34, wherein the display section displays information related to the number of steps and calorie consumption for a predetermined period of time selected by the user.

36. The portable terminal as claimed in claim 34, wherein the display section displays information related to the number of steps and calorie consumption in a form of figures or graphs according to selection of the user.

37. A method for measuring a quantity of exercise using an acceleration sensor for generating acceleration information by measuring the quantity of exercise according to a movement of a user, the method comprising the steps of:
  supplying power to the acceleration sensor at a first predetermined time section during a second predetermined time with a first time interval and sampling the acceleration information generated from the acceleration sensor at a second predetermined time section of the second predetermined time;
  converting the sampled acceleration information into dynamic energy and determining a step of the user by analyzing the dynamic energy; and
  displaying and storing information related to a number of steps.

38. The method as claimed in claim 37, wherein the acceleration information of the acceleration sensor is sampled when the acceleration sensor outputs the acceleration information after the acceleration sensor is driven, and then shuts off power being supplied to the acceleration sensor.

39. The method as claimed in claim 38, wherein a signal generated from the acceleration sensor is three-axis acceleration information for detecting a movement in X, Y and Z-axis directions and the three-axis acceleration information is combined when measuring the quantity of exercise in order to extract an energy component of a predetermined band from the acceleration information.

40. A method for measuring a quantity of exercise using an acceleration sensor generating acceleration information by measuring the quantity of exercise according to a movement of a user, the method comprising the steps of;
sampling the acceleration information generated from the acceleration sensor at a predetermined time interval;
converting the sampled acceleration information into dynamic energy, comparing a local maximum value with a predetermined threshold value if an ascending gradient of the dynamic energy has the local maximum value exceeding a predetermined value, and determining one step of the user if the local maximum value exceeds the predetermined threshold value; and
displaying and storing information related to a number of steps.

41. The method as claimed in claim 40, wherein the step of determining one step of the user comprises the substeps of:
accumulating acceleration information to allow the acceleration information to be subject to discrete cosine transform (DCT), converting the acceleration information into DCT acceleration information, combining DCT acceleration information in order to extract an energy component of a predetermined band, and comparing the local maximum value with the predetermined threshold value if the ascending gradient of the dynamic energy has the local maximum value exceeding the predetermined value and determining that one step is taken by the user if the local maximum value exceeds the predetermined threshold value.

42. The method as claimed in claim 41, wherein the step of determining the step of the user comprises the substeps of shifting from a standby state into a first state if the dynamic energy has the ascending gradient having a value exceeding a predetermined value, shifting from the first state to a second state if the dynamic energy has a local maximum value in the first state, shifting from the second state into the standby state while determining one step of the user if the local maximum value exceeds the predetermined threshold value and a time interval between a previous local maximum value and a present local maximum value is longer than a predetermined time in the second state, and instantly shifting into the standby state if at least one of the above two conditions is not satisfied.

43. The method as claimed in claim 41, further comprising the steps of determining a type of exerciser of the user by comparing a level of a high frequency signal of the DCT information generated from the DCT module and a level trigger signal with a reference level and a reference level trigger signal adaptable for at least two types of exercise, and supplying a sampling frequency to the acceleration sensor by determining the sampling frequency according to the type of exercise.

44. The method as claimed in claim 43, wherein the type of exercise is detected based on a time interval between steps and the sampling frequency in a fast walking mode is higher than the sample frequency in a normal walking mode.

45. The method as claimed in claim 43, wherein a signal generated from the acceleration sensor is three-axis acceleration information for detecting a movement in X, Y and Z-axis directions and the three-axis acceleration information is combined when measuring the quantity of exercise in order to extract an energy component of a predetermined band from the acceleration information.

46. A method for measuring a quantity of exercise using an acceleration sensor generating acceleration information by measuring the quantity of exercise according to a movement of a user, the method comprising the steps of:
supplying power to the acceleration sensor at a first predetermined time section during a second predetermined time with a first time interval and sampling the acceleration information generated from the acceleration sensor at a second predetermined time section of the second predetermined time;
converting the sampled acceleration information into dynamic energy, comparing a local maximum value with a predetermined threshold value if an ascending gradient of the dynamic energy has the local maximum value exceeding a predetermined value and determining one step being taken by a user if the local maximum value exceeds the predetermined threshold value;
calculating energy level values of energy level sections and calorie consumption values thereof by comparing measured energy level values of the energy level sections determined as the step of the user with the energy values of the energy level sections, in which energy level values of at least two energy level sections are determined through an experiment corresponding to a walking speed and calorie consumption thereof; and
storing and displaying information related to a number of steps and the calorie consumption generated from a calorie consumption measurement unit.

47. The method as claimed in claim 46, wherein a present energy level value is compared with the energy level values of the energy level sections, thereby calculating the energy level value of the energy level section and calorie consumption thereof.

48. The method as claimed in claim 42, wherein the calculated calorie consumption is updated by taking a weight of the user into consideration after calculating calorie consumption for a person having an average weight.

49. The method as claimed in claim 48, wherein the values of the level sections of the calorie consumption measurement unit are preset by means of the acceleration sensor according to a position of a portable terminal.

50. A method for measuring a quantity of exercise in a portable terminal equipped with a pedometer having an acceleration sensor generating acceleration information by measuring the quantity of exercise according to a movement of a user, the method comprising the steps of:
sampling the acceleration information generated from the acceleration sensor while controlling the acceleration sensor in every predetermined time of an operation mode;
determining a step of the user by measuring dynamic energy based on the sampled acceleration information and updating and storing data related to a number of steps when the dynamic energy is determined as the step of the user;
transmitting the data related to the number of steps to a controller of the portable terminal when the portable terminal requests transmission of the data; and
accumulating and storing information related to the number of steps and calorie information in the controller of the portable terminal.

51. The method as claimed in claim 50, wherein the step of sampling the acceleration information generated from the acceleration sensor comprises the substeps of supplying power to the acceleration sensor at a first predetermined time section during a second predetermined time with a first time interval thereby driving the acceleration sensor, sampling the acceleration information generated from the acceleration sensor at a predetermined point of the second predetermined time and shutting off the power being supplied to the acceleration sensor.

52. The method as claimed in claim 51, wherein the power-off step comprises the substeps of sampling the acceleration information of the acceleration sensor when the acceleration sensor outputs the acceleration information after the acceleration sensor is driven, and stopping power supply until the first predetermined time has lapsed.

53. The method as claimed in claim 51, wherein the step of determining a step of the user comprises the substeps of accumulating acceleration information to allow the acceleration information to be subject to discrete cosine transform (DCT), converting the acceleration information into DCT acceleration information, combining DCT acceleration information in order to extract an energy component of a predetermined band, and comparing the local maximum value with the predetermined threshold value if the ascending gradient of the dynamic energy has the local maximum value exceeding the predetermined value and determining that one step is taken by the user if the local maximum value exceeds the predetermined threshold value.

54. The method as claimed in claim 53, wherein the step of determining a step of the user comprises the substeps of shifting from a standby state into a first state if the dynamic energy has the ascending gradient having a value exceeding a predetermined value, shifting from the first state to a second state if the dynamic energy has a local maximum value in the first state, shifting from the second state into the standby state while determining one step of the user if the local maximum value exceeds the predetermined threshold value and a time interval between a previous local maximum value and a present local maximum value is longer than a predetermined time in the second state, and instantly shifting into the standby state if at least one of the above two conditions is not satisfied.

55. The method as claimed in claim 51, further comprising the steps of determining a type of exercise performed by the user by comparing a level of a high frequency signal of the DCT information and a level trigger signal with a reference level and a reference level trigger signal adaptable for at least two types of exercise, and supplying a sampling frequency to the acceleration sensor by determining the sampling frequency according to the type of exercise.

56. The method as claimed in claim 55, wherein the type of exercise is detected based on a time interval between steps and the sampling frequency in a fast walking mode is higher than the sample frequency in a normal walking mode.

57. The method as claimed in claim 53, wherein a signal generated from the acceleration sensor is three-axis acceleration information for detecting a movement in X, Y and Z-axis directions and the three-axis acceleration information is combined when measuring the quantity of exercise in order to extract an energy component of a predetermined band from the acceleration information.

58. The method as claimed in claim 50, further comprising the steps of comparing a present energy level value determined as the step of the user with a predetermined energy value of energy level sections and calculating and storing calorie consumption according to a result of the comparison, wherein the energy level values of at least two energy level sections are determined through an experiment corresponding to a walking speed and calorie consumption corresponding to the values of the energy level sections is predetermined.

59. The method as claimed in claim 58, further comprising the steps of determining a type of exercise performed by the user by comparing a level of a high frequency signal of the DCT information and a level trigger signal with a reference level and a reference level trigger signal adaptable for at least two types of exercise, and supplying a sampling frequency to the acceleration sensor by determining the sampling frequency according to the type of exercise.

60. The method as claimed in claim 59, wherein the type of exercise is detected based on a time interval between steps and the sampling frequency in a fast walking mode is higher than the sample frequency in a normal walking mode.

61. A method for displaying quantity of exercise using an acceleration sensor by sampling acceleration information generated from the acceleration sensor with a predetermined interval, the acceleration sensor generating the acceleration information by measuring the quantity of exercise according to a movement of a user, the method comprising the steps of:

accumulating the acceleration information in order to allow the acceleration information to be subject to discrete cosine transform (DCT);

calculating an average value of the accumulated acceleration information, comparing the average value of the accumulated acceleration information with a threshold value, regarding the acceleration information as acceleration information derived from a change of an angular position of an apparatus if the average value of the accumulated acceleration information exceeds the threshold value, and temporarily stopping measurement for dynamic energy during a predetermined period of time;

converting the accumulated acceleration information into DCT information if the average value of the accumulated acceleration information is within a range of the threshold value;

combining the DCT information in order to extract an energy component of a predetermined band from the DCT information; and comparing a local maximum value with a predetermined threshold value if an ascending gradient of extracted energy data has the local maximum value exceeding the predetermined value and determining one step of the user if the local maximum value exceeds the predetermined threshold value.

62. The method as claimed in claim 61, wherein the step of calculating an average value of the accumulated acceleration information comprises the substeps of calculating an average value of a predetermined number of accumulated acceleration information including sampled acceleration information, changing the average value into a maximum value if the average value is larger than a predetermined maximum value, changing the average value into a minimum value if the average value is smaller than a predetermined minimum value, and calculating a difference value between the maximum value and the minimum value, comparing the difference value with a predetermined threshold value, initializing the maximum value and the minimum value and stopping sampling work for the acceleration information for a predetermined period of time if the difference value is larger than the threshold value, and performing DCT if the difference value is smaller than the threshold value.

63. A method for displaying quantity of exercise using an acceleration sensor by sampling acceleration information generated from the acceleration sensor with a predetermined interval, the acceleration sensor generating the acceleration information by measuring the quantity of exercise according to a motion of a user, the method comprising the steps of:

accumulating the acceleration information in order to allow the acceleration information to be subject to discrete cosine transform (DCT);

converting the accumulated acceleration information into DCT information;

combining the DCT information in order to extract an energy component of a predetermined band from the DCT information;

accumulating the extracted energy components by dividing the extracted energy components into high frequency energy components and low frequency energy components, regarding the acceleration information as acceleration information derived from an error of the acceleration sensor if the high frequency components are larger than the low frequency components, and waiting for next sampling of the acceleration information; and inspecting extracted energy data if low frequency components are larger than the high frequency components, comparing a local maximum value with a predetermined threshold value if an ascending gradient of extracted energy data has the local maximum value exceeding the predetermined value and determining one step of the user if the local maximum value exceeds the predetermined threshold value.

64. The method as claimed in claim 63, wherein the low frequency component and high frequency component of the extracted energy are calculated according to the following equation:

$$E_{low} = \sum_{k=1}^{5}(|P_x(k)| + |P_x(k)| + |P_x(k)|)$$

$$E_{high} = \sum_{k=6}^{7}(|P_x(k)| + |P_x(k)| + |P_x(k)|).$$

65. A method for displaying quantity of exercise using an acceleration sensor by sampling acceleration information generated from the acceleration sensor with a predetermined interval, the acceleration sensor generating the acceleration information by measuring the quantity of exercise according to a movement of a user, the method comprising the steps of:

stopping an operation of a step counter if a step is not detected during a predetermined period of time;

accumulating the acceleration information in order to allow the acceleration information to be subject to discrete cosine transform (DCT) when a sampling input occurs;

converting the accumulated acceleration information into DCT information;

combining the DCT information in order to extract an energy component of a predetermined band from the DCT information;

comparing a local maximum value with a predetermined threshold value if an ascending gradient of extracted energy data has the local maximum value exceeding the predetermined value and determining one step of the user if the local maximum value exceeds the predetermined threshold value;

storing a step occurrence time when one step of the user is determined, inspecting the step counter, and changing information related to a number of steps if the step counter is an on-state; and inspecting whether a predetermined number of steps is continuously detected within a predetermined time if the step counter is an off-state, turning on the step counter if the predetermined number of steps is detected within the predetermined time, and maintaining the off-state of the step counter if the predetermined number of steps is not detected within the predetermined time.

66. The method as claimed in claim 65, wherein the step of stopping an operation of a step counter comprises the substeps of turning-on the step counter when a time interval between a predetermined odd sampling input and a predetermined even sampling input is within a predetermined time range, and turning-off the step counter if the time interval is out of the predetermined time range.

67. The method as claimed in claim 65, wherein the step of stopping an operation of a step counter comprises the substeps of turning-on the step counter when a time interval between predetermined sampling inputs is within a predetermined time range, and turning-off the step counter if the time interval is out of the predetermined time range.

68. A method for displaying a quantity of exercise using an acceleration sensor by sampling acceleration information generated from the acceleration sensor with a predetermined interval, the acceleration sensor generating the acceleration information by measuring the quantity of exercise according to a movement of a user, the method comprising the steps of:

stopping an operation of a step counter if a step is not detected during a predetermined period of time;

accumulating the acceleration information in order to allow the acceleration information to be subject to discrete cosine transform (DCT) when a sampling input occurs;

calculating an average value of the accumulated acceleration information, comparing the average value of the accumulated acceleration information with a threshold value, regarding the acceleration information as acceleration information derived from a change of an angular position of an apparatus if the average value of the accumulated acceleration information exceeds the threshold value, and temporarily stopping measurement for dynamic energy during a predetermined period of time;

converting the accumulated acceleration information into DCT information if the average value of the accumulated acceleration information is within the threshold value;

combining the DCT information in order to extract an energy component of a predetermined band from the DCT information;

accumulating the extracted energy components by dividing the extracted energy components into high frequency energy components and low frequency energy components, regarding the acceleration information as acceleration information derived from an error of the acceleration sensor if the high frequency components are larger than the low frequency components, and waiting for next sampling of the acceleration information;

inspecting extracted energy data if low frequency components are larger than the high frequency components, comparing a local maximum value with a predetermined threshold value if an ascending gradient of extracted energy data has the local maximum value exceeding the predetermined value and determining one step of the user if the local maximum value exceeds the predetermined threshold value;

storing a step occurrence time when one step of the user is determined, inspecting the step counter, and changing information related to a number of steps if the step counter is an on-state; and inspecting whether a predetermined number of steps is continuously detected within a predetermined time if the step counter is an off-state, turning on the step counter if the predetermined number of steps is detected within the predetermined time, and maintaining the off-state of the step counter if the predetermined number of steps is not detected within the predetermined time.

69. A method for controlling a pedometer of a portable terminal comprising an acceleration sensor generating acceleration information by measuring a quantity of exercise according to a motion of a user, the pedometer sampling the acceleration information generated from the acceleration sensor while controlling the acceleration sensor in every predetermined time of an operation mode, determining a step of the user by measuring dynamic energy based on the sampled acceleration information and updating and storing data related to a number of steps when the dynamic energy is determined as the step of the user, the method comprising the steps of:

generating a signal for controlling an operation of the pedometer with a predetermined time interval in the operation mode of the pedometer;

requesting data transmission to the pedometer, receiving information related to the number of steps measured by the pedometer, and storing and displaying the information; and transmitting a control signal to the pedometer to temporarily stop an operation of the pedometer when the portable terminal performs its functions.

70. The method as claimed in claim 69, wherein the control signal is generated upon a key input, an operation of a vibration motor, an output of audio sound through a speaker, or an on and or off operation of a folder or a slider.

71. A method for measuring quantity of exercise using an acceleration sensor generating acceleration information by measuring the quantity of exercise according to a motion of a user, the method comprising the steps of;

supplying power to the acceleration sensor for a predetermined period of time at a time section established by a sampling frequency of an operation mode and sampling the acceleration information generated from the acceleration sensor at a predetermined point of the predetermined period of time;

converting the sampled acceleration information into dynamic energy, and determining one step of the user by analyzing the dynamic energy;

storing a step occurrence time and maintaining the sampling frequency of the operation mode if the dynamic energy is determined as the step of the user, changing step information, and storing and displaying the step information;

checking a previous step occurrence time if the dynamic energy is not determined as the step of the user and replacing the sampling frequency with a lower sampling frequency, which is lower than the sampling frequency of the operation mode when a predetermined time has lapsed from the previous step occurrence time.

72. The method as claimed in claim 71, wherein at least two lower sampling frequencies and predetermined times for replacing the sampling frequency with the lower sampling frequencies are prepared, and a predetermined period of time, in which the step is not detected, is compared with the predetermined times in order to sequentially replace the sampling frequency with the lower sampling frequencies in an order of the frequency thereof.

* * * * *